US012133846B2

(12) United States Patent
Qin et al.

(10) Patent No.: US 12,133,846 B2
(45) Date of Patent: Nov. 5, 2024

(54) ELECTROPHILIC ANDROGEN RECEPTOR (AR) ANTAGONISTS FOR AR DOWNREGULATION AND FERROPTOSIS INDUCTION IN CANCER CELLS

(71) Applicant: WAYNE STATE UNIVERSITY, Detroit, MI (US)

(72) Inventors: Zhihui Qin, Mundelein, IL (US); Liping Xu, Detroit, MI (US)

(73) Assignee: Wayne State University, Detroit, MI (US)

(*) Notice: Subject to any disclaimer, the term of this patent is extended or adjusted under 35 U.S.C. 154(b) by 806 days.

(21) Appl. No.: 17/071,896

(22) Filed: Oct. 15, 2020

(65) Prior Publication Data

US 2021/0106571 A1    Apr. 15, 2021

Related U.S. Application Data

(60) Provisional application No. 62/915,500, filed on Oct. 15, 2019.

(51) Int. Cl.
*A61K 31/4439* (2006.01)
*A61K 31/198* (2006.01)
*A61K 47/54* (2017.01)

(52) U.S. Cl.
CPC ........ *A61K 31/4439* (2013.01); *A61K 31/198* (2013.01); *A61K 47/54* (2017.08)

(58) Field of Classification Search
None
See application file for complete search history.

(56) References Cited

U.S. PATENT DOCUMENTS

| 5,994,402 A | 11/1999 | Rotstein et al. |
| 9,289,436 B2 | 3/2016 | Szmulewitz et al. |
| 2015/0259309 A1 | 9/2015 | Chowdhury et al. |
| 2018/0214390 A1 | 8/2018 | Estrela et al. |

FOREIGN PATENT DOCUMENTS

| KR | 20080058663 A | 6/2008 |
| WO | WO2009025145 A1 | 2/2009 |
| WO | WO2015184393 A1 | 12/2015 |
| WO | WO2017192740 A2 | 11/2017 |
| WO | WO2020205919 A1 | 10/2020 |

OTHER PUBLICATIONS

Siyu Ou, "Design and Synthesis of Enzalutamide-Isothiocyanate Hybrid Drug as Anti-Prostate Cancer Agent," Wayne State University Theses available online in 2016. (Year: 2016).*
Ahn, et al., "Electrophilic tuning of the chemoprotective natural product sulforaphane," PNAS USA, vol. 107, No. 21, 2010, pp. 9590-9595.
Alumkal, et al., "A phase II study of sulforaphane-rich broccoli sprout extracts in men with recurrent prostate cancer," Investigational New Drugs, vol. 33, 2015, pp. 480-489.
Beer, et al., "Enzalutamide in Metastatic Prostate Cancer before Chemotherapy," New England Journal of Medicine, vol. 371, No. 5, 2014, pp. 424-433.
Beklemisheva, et al., "Modulating testosterone stimulated prostate growth by phenethyl isothiocyanate via Sp1 and androgen receptor down-regulation," Prostate, vol. 67, No. 8, 2007, pp. 863-870.
Beretta & Zaffaroni, "Androgen Receptor-Directed Molecular Conjugates for Targeting Prostate Cancer," Frontiers in Chemistry, vol. 7, No. 369, 2019, 9 pages.
Bhattacharya, et al., "The principal urinary metabolite of allyl isothiocyanate, N-acetyl-S-( N-allylthiocarbamoyl) cysteine, inhibits the growth and muscle invasion of bladder cancer," Carcinogenesis, vol. 32, No. 2, 2012, pp. 394-398.
Callaway, et al., "Cellular accumulation of dietary anticarcinogenic isothiocyanates is followed by transporter-mediated export as dithiocarbamates," Cancer Letters, vol. 204, No. 1, 2004, pp. 23-31.
Cano, et al., "Mini-review: Foldosome regulation of androgen receptor action in prostate cancer," Molecular and Cellular Endocrinology, vol. 369, No. 1-2, 2013, pp. 52-62.
Chang, et al., "Dihydrotestosterone synthesis bypasses testosterone to drive castration-resistant prostate cancer," PNAS USA, vol. 108, No. 33, 2011, pp. 13728-13733.
Chang, et al., "Heme oxygenase-1 mediates BAY 11-7085 induced ferroptosis," Cancer Letters, vol. 416, 2018, pp. 124-137.
Chen, et al., "Anti-androgens and androgen-depleting therapies in prostate cancer: new agents for an established target," Lancet Oncology, vol. 10, No. 10, 2009, pp. 981-991.
Ciccarese, et al., "Prostate cancer heterogeneity: Discovering novel molecular targets for therapy," Cancer Treatment Reviews, vol. 54, 2017, pp. 68-73.
Civenni, et al., "RNAi-Mediated Silencing of Myc Transcription Inhibits Stem-like Cell Maintenance and Tumorigenicity in Prostate Cancer," Cancer Research, vol. 73, No. 22, 2013, pp. 6816-6827.
Conaway, et al., "Decomposition Rates of Isothiocyanate Conjugates Determine Their Activity as Inhibitors of Cytochrome P450 Enzymes," Chemical Research Toxicology, vol. 14, No. 9, 2001, pp. 1170-1176.
Cramer, et al., "Systemic depletion of L-cyst(e)ine with cyst(e)inase increases reactive oxygen species and suppresses tumor growth," Nature Medicine, vol. 23, No. 1, 2017, pp. 120-127.
Crona, et al., "Androgen receptor targeting drugs in castration-resistant prostate cancer and mechanisms of resistance," Clinical Pharmacology & Therapeutics, vol. 98, No. 6, 2015, pp. 582-589.
Dinkova-Kostova, et al., "Direct evidence that sulfhydryl groups of Keap1 are the sensors regulating induction of phase 2 enzymes that protect against carcinogens and oxidants," PNAS USA, vol. 99, No. 18, 2002, pp. 11908-11913.

(Continued)

*Primary Examiner* — Jeffrey S Lundgren
*Assistant Examiner* — Michael J Schmitt
(74) *Attorney, Agent, or Firm* — Lee & Hayes, P.C.

(57) ABSTRACT

Isothiocyanate (ITC)-androgen receptor (AR) inhibitor conjugates for apoptosis induction in cancer cells are described. The conjugates can have electrophilicity blocked with an agent such as N-acetyl cysteine. When administered in combination with a glutathione (GSH)-depleting agent, the conjugates result in ferroptosis of cancer cells.

10 Claims, 20 Drawing Sheets

(56) References Cited

OTHER PUBLICATIONS

Falchi, et al., "Synthetic Lethality Triggered by Combining Olaparib with BRCA2-Rad51 Disruptors," ACS Chemical Biology, vol. 12, No. 10, 2017, pp. 2491-2497.
Feng & Stockwell, "Unsolved mysteries: How does lipid peroxidation cause ferroptosis?," PLOS Biology, vol. 16, No. 5, 2018, 15 pages.
Garcia-Moreno, et al., "One-step synthesis of non-anomeric sugar isothiocyanates from sugar azides," Carbohydrate Research, vol. 337, No. 21-23, 2002, pp. 2329-2334.
Gibbs, et al., "Sulforaphane destabilizes the androgen receptor in prostate cancer cells by inactivating histone deacetylase 6," PNAS USA, vol. 106, No. 39, 2009, pp. 16663-16668.
Griffith & Meister, "Potent and specific inhibition of glutathione synthesis by buthionine sulfoximine (S-n-butyl homocysteine sulfoximine)," Journal of Biological Chemistry, vol. 254, No. 16, 1979, pp. 7558-7560.
Guo, et al., "Discovery of Aryloxy Tetramethylcyclobutanes as Novel Androgen Receptor Antagonists," Journal of Medicinal Chemistry, vol. 54, No. 21, 2011, pp. 7693-7704.
Haapala, et al., "Androgen receptor amplification is associated with increased cell proliferation in prostate cancer," Human Pathology, vol. 38, No. 3, 2007, pp. 474-478.
Hangauer, et al., "Drug-tolerant persister cancer cells are vulnerable to GPX4 inhibition," Nature, vol. 551, No. 7679, 2017, pp. 247-250.
Harris, et al., "Androgen deprivation therapy: progress in understanding mechanisms of resistance and optimizing androgen depletion," Nature Clinical Practice Urology, vol. 6, No. 2, 2009, pp. 76-85.
Harris, et al., "Glutathione and Thioredoxin Antioxidant Pathways Synergize to Drive Cancer Initiation and Progression," Cancer Cell, vol. 27, No. 2, 2015, pp. 211-222.
Wang & Lee, "Effects of phenylethyl isothiocyanate and its metabolite on cell-cycle arrest and apoptosis in LNCaP human prostate cancer cells," International Journal of Food Sciences and Nutrition, vol. 61, No. 3, 2010, pp. 324-336.
Jiao, et al., "Chemopreventive activity of thiol conjugates of isothiocyanates for lung tumorigenesis," Carcinogenesis, vol. 18, No. 11, 1997, pp. 2143-2147.
Joseph, et al., "A Clinically Relevant Androgen Receptor Mutation Confers Resistance to Second-Generation Antiandrogens Enzalutamide and ARN-509," Cancer Discovery, vol. 3, No. 9, 2013, pp. 1020-1029.
Karantanos, et al., "Understanding the Mechanisms of Androgen Deprivation Resistance in Prostate Cancer at the Molecular Level," European Urology, vol. 67, No. 3, 2015, pp. 470-479.
Kitson, et al., "Synthesis of 19-substituted geldanamycins with altered conformations and their binding to heat shock protein Hsp90," Nature Chemistry, vol. 5, 2013, pp. 307-314.
Kobayashi, et al., "Oxidative and Electrophilic Stresses Activate Nrf2 through Inhibition of Ubiquitination Activity of Keap1," Molecular and Cellular Biology, vol. 26, No. 1, 2006, pp. 221-229.
Korpal, et al., "An F876L Mutation in Androgen Receptor Confers Genetic and Phenotypic Resistance to MDV3100 (Enzalutamide)," Cancer Discovery, vol. 3, No. 9, 2013, pp. 1030-1043.
Lai, et al., "New Therapeutic Approach to Suppress Castration-Resistant Prostate Cancer Using ASC-J9 via Targeting Androgen Receptor in Selective Prostate Cells, " The American Journal of Pathology, vol. 182, No. 2, 2013, pp. 460-473.
Lee & Grossmann, "Reversible covalent inhibition of a protein target," Angewandte Chemie International Edition, vol. 51, No. 35, 2012, pp. 8699-8700.
Li, et al., "Androgen Receptor Splice Variants Mediate Enzalutamide Resistance in Castration-Resistant Prostate Cancer Cell Lines," Cancer Research, vol. 73, No. 2, 2013, pp. 483-489.
Li, et al., "Sulforaphane inhibits pancreatic cancer through disrupting Hsp90-p50Cdc37 complex and direct interactions with amino acids residues of Hsp90," Journal of Nutritional Biochemistry, vol. 23, No. 12, 2012, pp. 1617-1626.
Lien, et al., "Glutathione biosynthesis is a metabolic vulnerability in PI(3)K/Akt-driven breast cancer," Nature Cell Biology, vol. 18, No. 5, 2016, pp. 572-578.
Liu, et al., "Crosstalk between IGF-1R and other Tumor Promoting Pathways," Current Pharmaceutical Design, vol. 20, No. 17, 2014, pp. 2912-2921.
McKenzie & Kyprianou, "Apoptosis evasion: The role of survival pathways in prostate cancer progression and therapeutic resistance," Journal of Cellular Biochemistry, vol. 97, No. 1, 2006, pp. 18-32.
Mi, et al., "Proteins as binding targets of isothiocyanates in cancer prevention," Carcinogenesis, vol. 32, No. 10, 2011, pp. 1405-1413.
Mi, et al., "The Role of Protein Binding in Induction of Apoptosis by Phenethyl Isothiocyanate and Sulforaphane in Human Non-Small Lung Cancer Cells," Cancer Research, vol. 63, No. 13, 2007, pp. 6409-6416.
Minotti & Aust, "Redox cycling of iron and lipid peroxidation," Lipids, vol. 27, No. 3, 1992, pp. 219-226.
Mitsiades, "A Road Map to Comprehensive Androgen Receptor Axis Targeting for Castration-Resistant Prostate Cancer," Cancer Research, vol. 73, No. 15, 2013, pp. 4599-4605.
Moses, et al., "Targeting the Hsp40/Hsp70 Chaperone Axis as a Novel Strategy to Treat Castration-Resistant Prostate Cancer," Cancer Research, vol. 78, No. 14, 2018, pp. 4022-4035.
Myzak, et al., "A Novel Mechanism of Chemoprotection by Sulforaphane: Inhibition of Histone Deacetylase," Cancer Research, vol. 64, No. 5, 2004, pp. 5767-5774.
Myzak, et al., "Sulforaphane inhibits histone deacetylase activity in BPH-1, LnCaP and PC-3 prostate epithelial cells," Carcinogenesis, vol. 27, No. 4, 2006, pp. 811-819.
Nadiminty, et al., "NF-KAPPAB2/p52:c-Myc:hnRNPA1 Pathway Regulates Expression of Androgen Receptor Splice Variants and Enzalutamide Sensitivity in Prostate Cancer," Molecular Cancer Therapeutics, vol. 14, No. 8, 2015, pp. 1884-1895.
Nakamura, et al., "In situ androgen producing enzymes in human prostate cancer," Endocrine-Related Cancer, vol. 12. No. 1, 2005, pp. 101-107.
Njar, "Androgen receptor antagonism and impact on inhibitors of androgen synthesis in prostate cancer therapy," Translational Cancer Research, vol. 6, No. 7, 2017, pp. S1128-S1131.
O'Dwyer, et al., "Phase I trial of buthionine sulfoximine in combination with melphalan in patients with cancer," Journal of Clinical Oncology, vol. 14, No. 1, 1996, pp. 249-256.
Ou, et al., "Abstract A197: Synthesis and in vitro anti-prostate cancer activities of androgen receptor ligand-sothiocyanate hybrid drug," Molecular Cancer Therapeutics, vol. 17, No. 1, 2018.
Pepe, et al., "Synthesis and Structure-Activity Relationship Studies of Novel Dihydropyridones as Androgen Receptor Modulators," Journal of Medicinal Chemistry, vol. 56, No. 21, 2013, pp. 8280-8297.
Perdrix, et al., "PRIMA-1 and PRIMA-1Met (APR-246): From Mutant/Wild Type p53 Reactivation to Unexpected Mechanisms Underlying Their Potent Anti-Tumor Effect in Combinatorial Therapies," Cancers, vol. 9, No. 12, 2017, 17 pages.
Pippione, et al., "Androgen-AR axis in primary and metastatic prostate cancer: chasing steroidogenic enzymes for therapeutic intervention," Journal of Cancer Metastasis and Treatment, vol. 3, 2017, pp. 328-361.
Rapozzi, et al., "Androgen Receptor Targeted Conjugate for Bimodal Photodynamic Therapy of Prostate Cancer in Vitro," Bioconjugate Chemistry, vol. 26, No. 8, 2015, pp. 1662-1671.
Sakao, et al., "CXCR4 Is a Novel Target of Cancer Chemopreventative Isothiocyanates in Prostate Cancer Cells," Cancer Prevention Research, vol. 8, No. 5, 2015, pp. 365-374.
Sankpal, et al., "Targeting SP1 Transcription Factor in Prostate Cancer Therapy," Medicinal Chemistry, vol. 7, No. 5, 2011, pp. 518-525.
Scher, et al., "Increased Survival with Enzalutamide in Prostate Cancer after Chemotherapy," New England Journal of Medicine, vol. 367, No. 13, 2012, pp. 1187-1197.
Shibata, et al., "Transthiocarbamoylation of Proteins by Thiolated Isothiocyanates," Journal of Biological Chemistry, vol. 286, No. 49, 2011, pp. 42150-42161.

(56) References Cited

OTHER PUBLICATIONS

Siegel, et al., "Cancer statistics for Hispanics/Latinos, 2015," CA: A Cancer Journal for Clinicians, vol. No. 6, 2015, pp. 457-480.
Skouta, et al., "Ferrostatins Inhibit Oxidative Lipid Damage and Cell Death in Diverse Disease Models," J. Am. Chem. Soc., vol. 136, No. 12, 2014, pp. 4551-4556.
Stockwell, et al., "Ferroptosis: A Regulated Cell Death Nexus Linking Metabolism, Redox Biology, and Disease," Cell, vol. 171, No. 2, 2017, pp. 273-285.
Trachootham, et al., "Selective killing of oncogenically transformed cells through a ROS-mediated mechanism by BETA-phenylethyl isothiocyanate," Cancer Cell, vol. 10, No. 3, 2006, pp. 241-252.
Traka, et al., "Sulforaphane and prostate cancer interception," Drug Discovery Today, vol. 19, No. 9, 2014, pp. 1488-1492.
Tran, et al., "Development of a Second-Generation Antiandrogen for Treatment of Advanced Prostate Cancer," Science, vol. 324, No. 5928, 2009, pp. 787-790.
Viswanathan, et al., "Dependency of a therapy-resistant state of cancer cells on a lipid peroxidase pathway," Nature, vol. 547, 2017, pp. 453-457.
Vyas, et al., "Sulforaphane Inhibits c-Myc-Mediated Prostate Cancer Stem-Like Traits," Journal of Cellular Biochemistry, vol. 117, No. 11, 2016, pp. 2482-2495.
Wang, et al., "De-repression of the p21 promoter in prostate cancer cells by an isothiocyanate via inhibition of HDACs and c-Myc," Journal of Oncology, vol. 33, No. 2, 2008, pp. 375-380.
Wang, et al., "Repression of androgen receptor in prostate cancer cells by phenethyl isothiocyanate," Carcinogenesis, vol. 27, No. 10, 2006, pp. 2124-2132.
Watson, et al., "Emerging mechanisms of resistance to androgen receptor inhibitors in prostate cancer," Nature Reviews Cancer, vol. 15, No. 12, 2015, pp. 701-711.
Wilson, et al., "A Novel Cell Line, MDA-kb2, That Stably Expresses an Androgen- and Glucocorticoid-Responsive Reporter for the Detection of Hormone Receptor Agonists and Antagonists," Toxicological Sciences, vol. 66, No. 1, 2002, pp. 69-81.
Yang, et al., "Regulation of Ferroptotic Cancer Cell Death by GPX4," Cell, vol. 156, No. 1-2, 2014, pp. 317-331.
Yoshino, et al., "Design and synthesis of an androgen receptor pure antagonist (CH5137291) for the treatment of castration-resistant prostate cancer," Bioorganic & Medicinal Chemistry, vol. 18, No. 23, 2010, pp. 8150-8157.
Yu, et al., "Phenethyl isothiocyanate inhibits androgen receptor-regulated transcriptional activity in prostate cancer cells through suppressing PCAF," Mol. Nutr. Food Res., vol. 57, No. 10, 2013, pp. 1825-1833.
Zhang, et al., "HSF1-Dependent Upregulation of Hsp70 by Sulfhydryl-Reactive Inducers of the KEAP1/NRF2/ARE Pathway," Chemistry & Biology, vol. 18, No. 11, 2011, pp. 1355-1361.
Zhang, et al., "Imidazole Ketone Erastin Induces Ferroptosis and Slows Tumor Growth in a Mouse Lymphoma Model," Cell Chemical Biology, vol. 26, No. 5, 2019, pp. 623-633.
Zhang, et al., "The molecular basis that unifies the metabolism, cellular uptake and chemopreventive activities of dietary isothiocyanates," Carcinogenesis, vol. 33, No. 1, 2012, pp. 2-9.
Zilka, et al., "On the Mechanism of Cytoprotection by Ferrostatin-1 and Liproxstatin-1 and the Role of Lipid Peroxidation in Ferroptotic Cell Death," ACS Central Science, vol. 3, No. 3, 2017, pp. 232-243.

* cited by examiner

FIG. 14

Interaction Index (VCaP)

| 2-63 (µM) | BSO (µM) | | |
|---|---|---|---|
| | 2.5 | 5 | 10 |
| 1 | 0.83 | 0.81 | 0.70 |
| 2.5 | 0.62 | 0.46 | 0.42 |
| 5 | 0.43 | 0.34 | 0.33 |

Interaction Index (22Rv-1)

| 2-63 (µM) | BSO (µM) | | |
|---|---|---|---|
| | 2.5 | 5.0 | 10 |
| 2.5 | 0.81 | 0.70 | 0.67 |
| 5.0 | 0.63 | 0.60 | 0.60 |
| 10 | 0.70 | 0.68 | 0.66 |

X=H, CN

X=H, CN; Y=CH$_2$, O, NH, NCH$_3$.

ELECTROPHILIC ANDROGEN RECEPTOR (AR) ANTAGONISTS FOR AR DOWNREGULATION AND FERROPTOSIS INDUCTION IN CANCER CELLS

CROSS-REFERENCE TO RELATED APPLICATION

This application claims priority to U.S. Provisional Patent Application No. 62/915,500 filed Oct. 15, 2019, the entire contents of which are incorporated by reference in their entirety.

STATEMENT REGARDING FEDERALLY SPONSORED RESEARCH OR DEVELOPMENT

This invention was made with government support under grant W81XWH-12-1-0340, awarded by the Department of Defense Prostate Cancer Research Program Idea Development Award. The government has certain rights in the invention.

FIELD OF THE DISCLOSURE

Isothiocyanate (ITC)-androgen receptor (AR) inhibitor conjugates for apoptosis induction in cancer cells are described. The conjugates can have electrophilicity reduced with an agent such as N-acetyl cysteine. When administered in combination with a glutathione (GSH)-depleting agent, the conjugates result in the ferroptosis of cancer cells.

BACKGROUND OF THE DISCLOSURE

Cancer (neoplasia) is characterized by deregulated cell growth and cell division. There are numerous types of cancers. Examples of cancers include prostate cancer and breast cancer. Prostate cancer (PCa), as its name indicates, is cancer that develops in the prostate gland of the male reproductive system. Prostate cancer can be aggressive, in which cancer cells metastasize and move from the prostate gland to other parts of the body, such as the lymph nodes and the bones. It is the second leading cause of cancer-related death in men in the U.S., and its prevalence is increasing in developing countries.

Prostate cancer growth is often driven by male sex hormones called androgens, which include testosterone. Because of this, a common treatment option for those individuals that cannot be treated with surgery, radiation, cryotherapy, or watchful waiting is to lower the levels of androgens in the man's body. Androgen levels can be lowered by surgically removing the testicles or with drugs that stop the testicles and, to a lesser extent, adrenal glands, from making androgens or block how they affect the body. This type of treatment is called hormonal therapy or androgen-deprivation therapy. Unfortunately, many patients begin to fail hormonal therapy or become hormone-refractory. That is, they develop castration-resistant prostate cancer (CRPC) or hormone-refractory prostate cancer (HRPC). Nevertheless, CRPC tumors typically continue to produce androgen. CRPC tumors may continue to depend on androgen receptor (AR) signaling for growth by producing greatly elevated AR levels or producing variant forms of AR that are constitutively active in addition to the normal full-length AR (FL AR). Treatment options for prostate cancer are very limited once the disease becomes resistant to hormonal therapy through these or any other mechanisms.

Because sustained AR signaling remains one of the central driving forces of CRPC (Mitsiades, N, Cancer Res 2013; 73(15): 4599-605), new generation non-steroid AR antagonists, such as enzalutamide (Enz), have been developed and approved for CRPC treatment (Beer, et al. N Engl J Med 2014; 371(5): 424-33). However, drug resistance often develops, and the survival benefits of Enz and related compounds in CRPC can be short-lived.

Isothiocyanates (ITCs), such as phenethyl ITC (PEITC) and sulforaphane (SFN), are bioactive metabolites of naturally occurring glucosinolates existing in cruciferous vegetables (e.g., broccoli, cabbage, watercress, etc.). Epidemiological studies demonstrate a positive correlation between cruciferous vegetable consumption and decreased incidence of PCa, and ITCs are among the major dietary components contributing to this health benefit. In recurrent PCa patients, SFN-enriched broccoli sprout extracts prolonged prostate-specific antigen (PSA) doubling time without severe adverse events, indicating a potential for further dose escalation.

SUMMARY OF THE DISCLOSURE

The current disclosure provides a novel class of hybrid drugs that is designed by incorporating an isothiocyanate moiety into the chemical scaffold of an AR inhibitor with, in certain examples, full (FL) AR binding affinity. The hybrid drugs can have electrophilicity transiently reduced with an agent such as N-acetyl cysteine (NAC) to yield NAC conjugates. These hybrid drugs or NAC conjugates can be administered in combination with one or more glutathione (GSH)-depleting agents creating synergistic anti-cancer effects. Importantly, the hybrid drugs or drug conjugates and combination treatments described herein can result in cancer cell destruction through ferroptosis rather than apoptosis, providing a treatment modality against apoptosis-resistant cancer cells. The current disclosure also provides compositions, including the novel drugs and methods of using the compositions to treat AR positive cancers such as prostate cancer.

BRIEF DESCRIPTION OF THE SEVERAL VIEWS OF THE DRAWINGS

Some of the drawings submitted herein may better be understood in color. Applicant considers the color versions of the drawings as part of the original submission and reserves the right to present color images of the drawings in later proceedings.

C. Aliquots (10 µL) were taken at indicated time points and analyzed using High-Performance Liquid Chromatography (HPLC).

Figure 4:
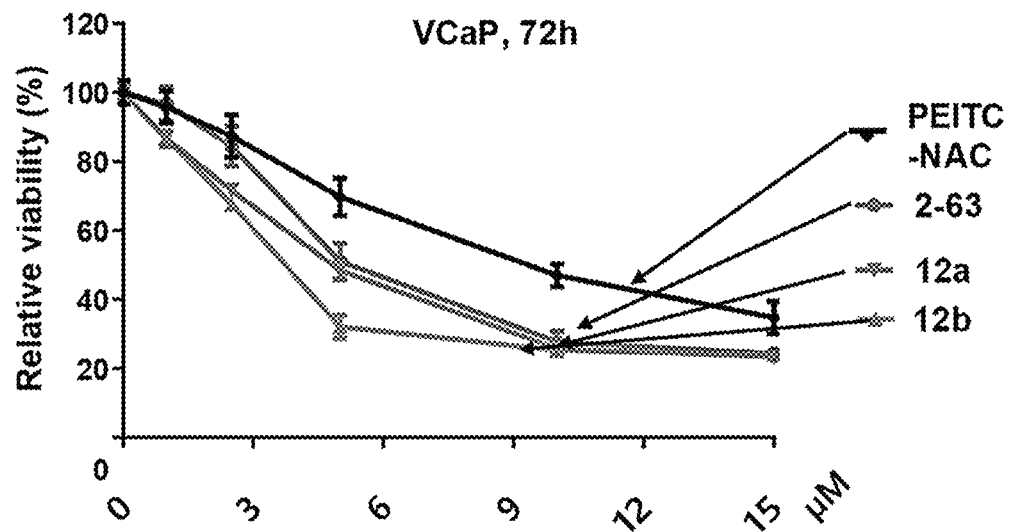

FIG. 4: ITC-ARi hybrid drugs effectively reduce the viability of PCa cells. Vertebral-Cancer of the Prostate (VCaP) cells were treated with the indicated compounds at various concentrations for 72 h. Cell viability was measured using an MTT assay (n=6-8). All data are means±SEM.

Figure 5:
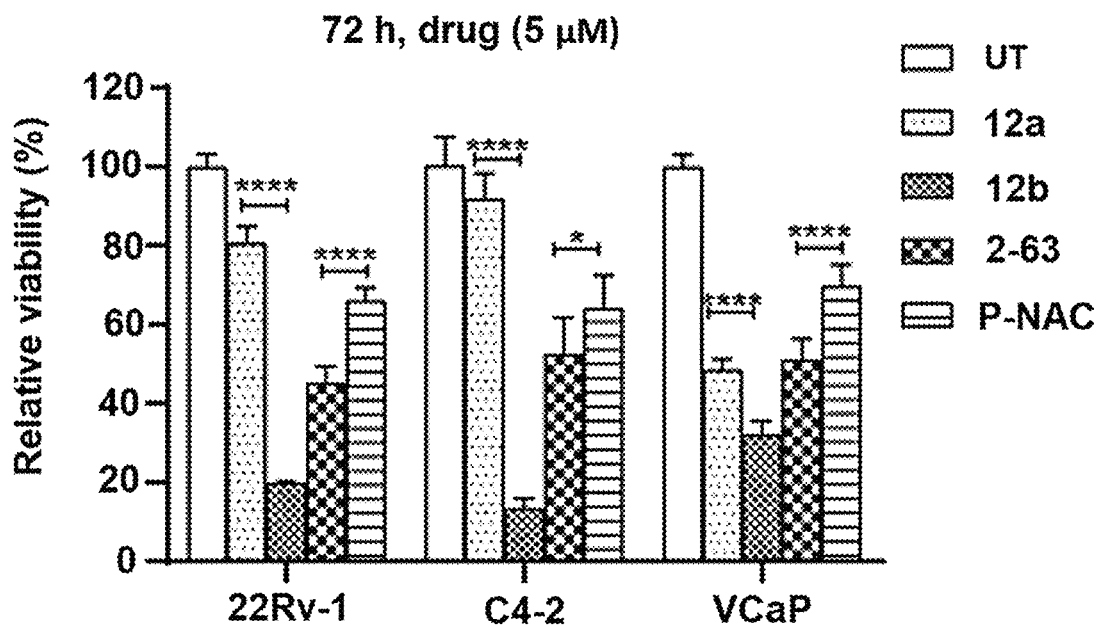

FIG. 5: ITC-ARi hybrid drugs effectively reduce the viability of PCa cells. VCaP, 22Rv1, and C4-2 cells were treated with the indicated compounds at 5 µM for 72 h. Cell viability was measured using an MTT assay.

Figure 6:
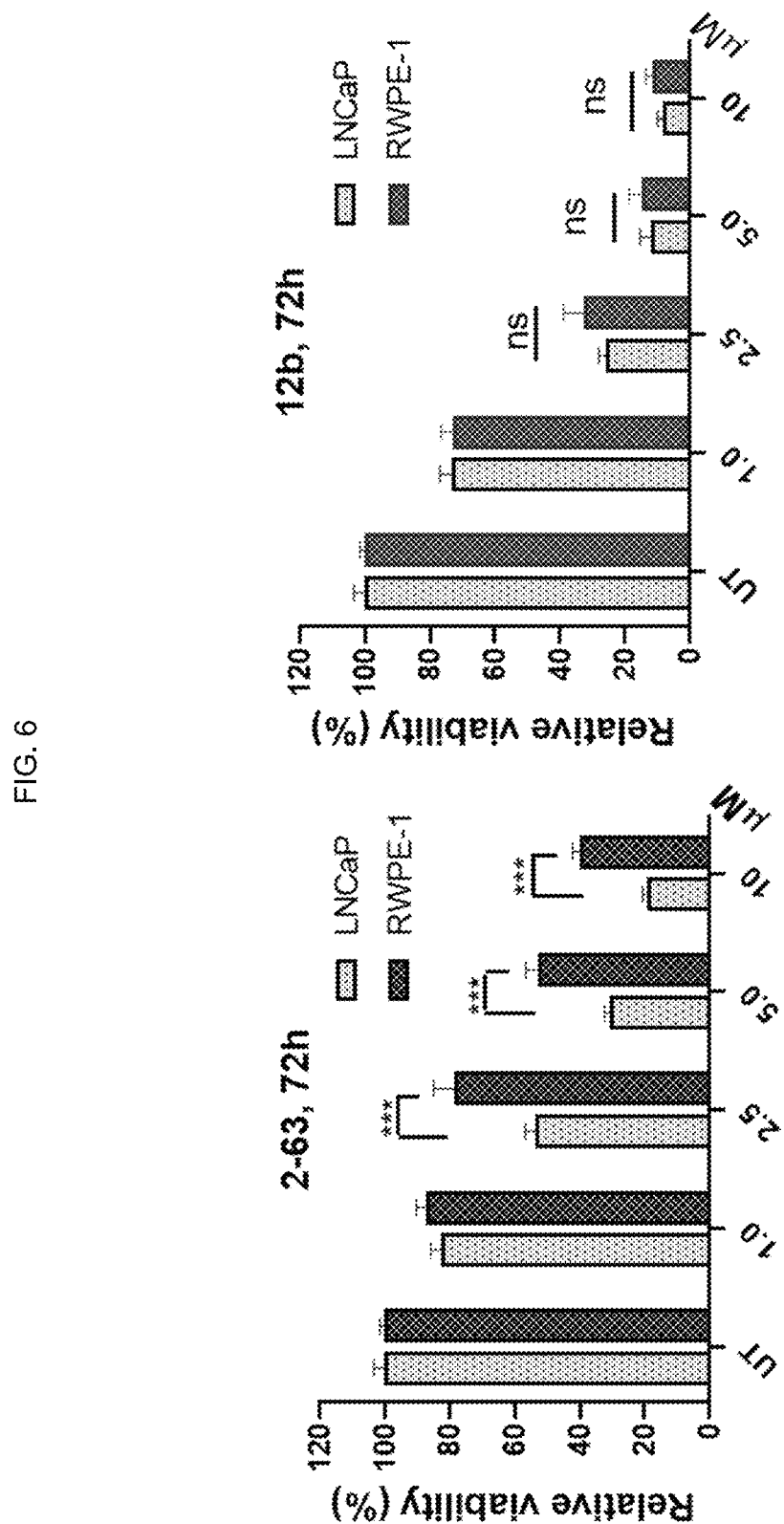

FIG. 6: ITC-ARi hybrid drugs effectively reduce the viability of PCa cells. Cell viability was measured using an MTT assay. Data represent mean±SD (n=6-8). *, P<0.05; **, P<0.0001. LNCaP and RWPE-1 cells were treated with the indicated compounds for 72 h, respectively. Cell viability was measured using an MTT assay (n=6-8). Data represent mean±SD (n=6-8). ns, not significant; *, P<0.001.

Figure 7:
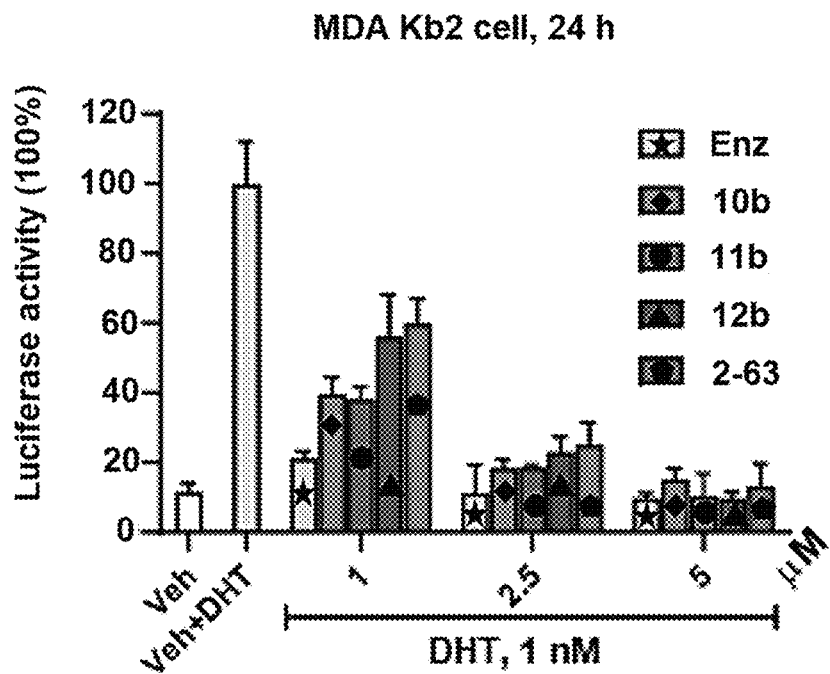

FIG. 7: 2-63 induces AR antagonism. 2-63 inhibits dihydrotestosterone (DHT) (1 nM)-stimulated AR transcriptional activity in MDA-kb2 cells. Data reflect mean±SD (n=4).

Figure 8:
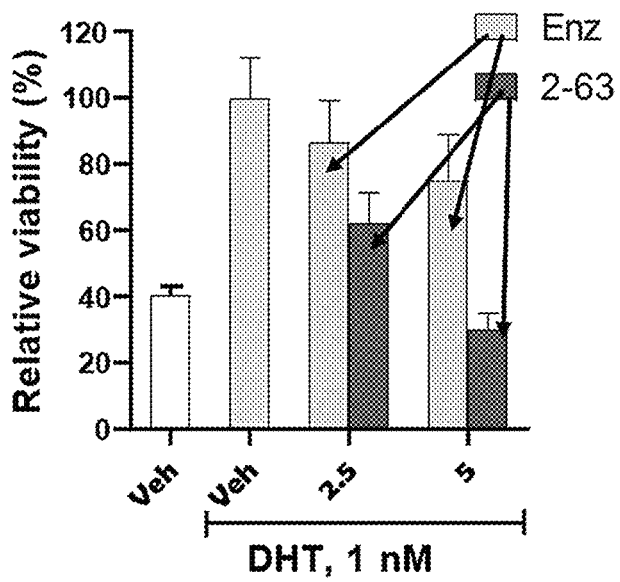

FIG. 8: 2-63 induces AR antagonism. C4-2 cells were cultured in medium supplemented with charcoal stripped FBS (10%) and were treated with Enz and 2-63 at 2.5 and 5 µM in the presence of DHT (1 nM) for 6 days. The medium and drug were refreshed every two days.

Figure 9:
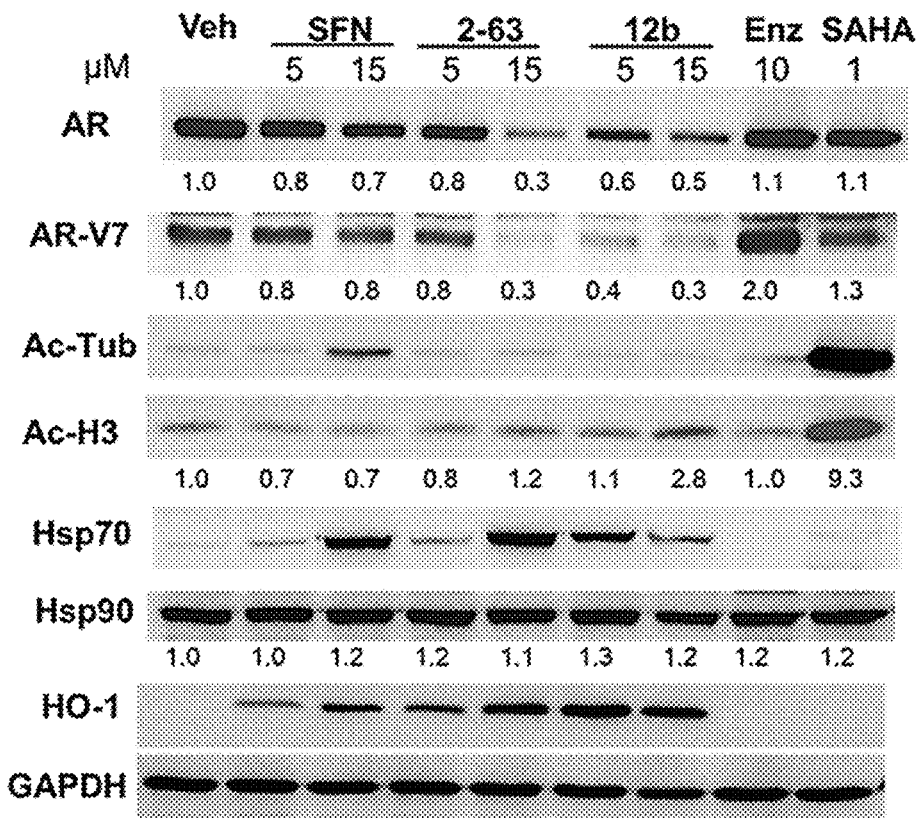

FIG. 9: 2-63 induces AR antagonism. 2-63 downregulates the expression of FL AR and AR splice variant 7 (AR-V7). VCaP cells were treated with 2-63, 12b, SFN, Enz, and suberoylanilide hydroxamic acid (SAHA) at the indicated concentration for 16 h. Whole cell lysates were subjected to Western blotting and probed with the indicated antibodies. Relative expression levels normalized against glyceraldehyde 3-phosphate dehydrogenase (GAPDH) are indicated under blots. Veh, Vehicle.

Figure 10:
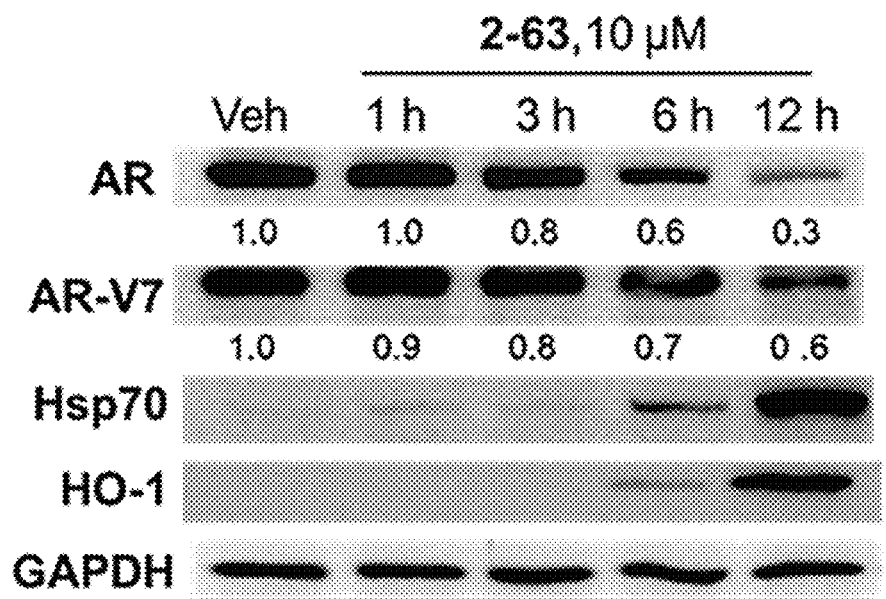

FIG. 10: 2-63 induces AR antagonism. VCaP cells were treated with 2-63 (10 µM) for the indicated time. AR, AR-V7, heat shock protein 70 (Hsp70), and hemo-oxygenase-1 (HO-1) proteins were analyzed using Western blotting and densitometry. Relative expression levels normalized against GAPDH are indicated under blots. Veh, Vehicle.

Figure 11:
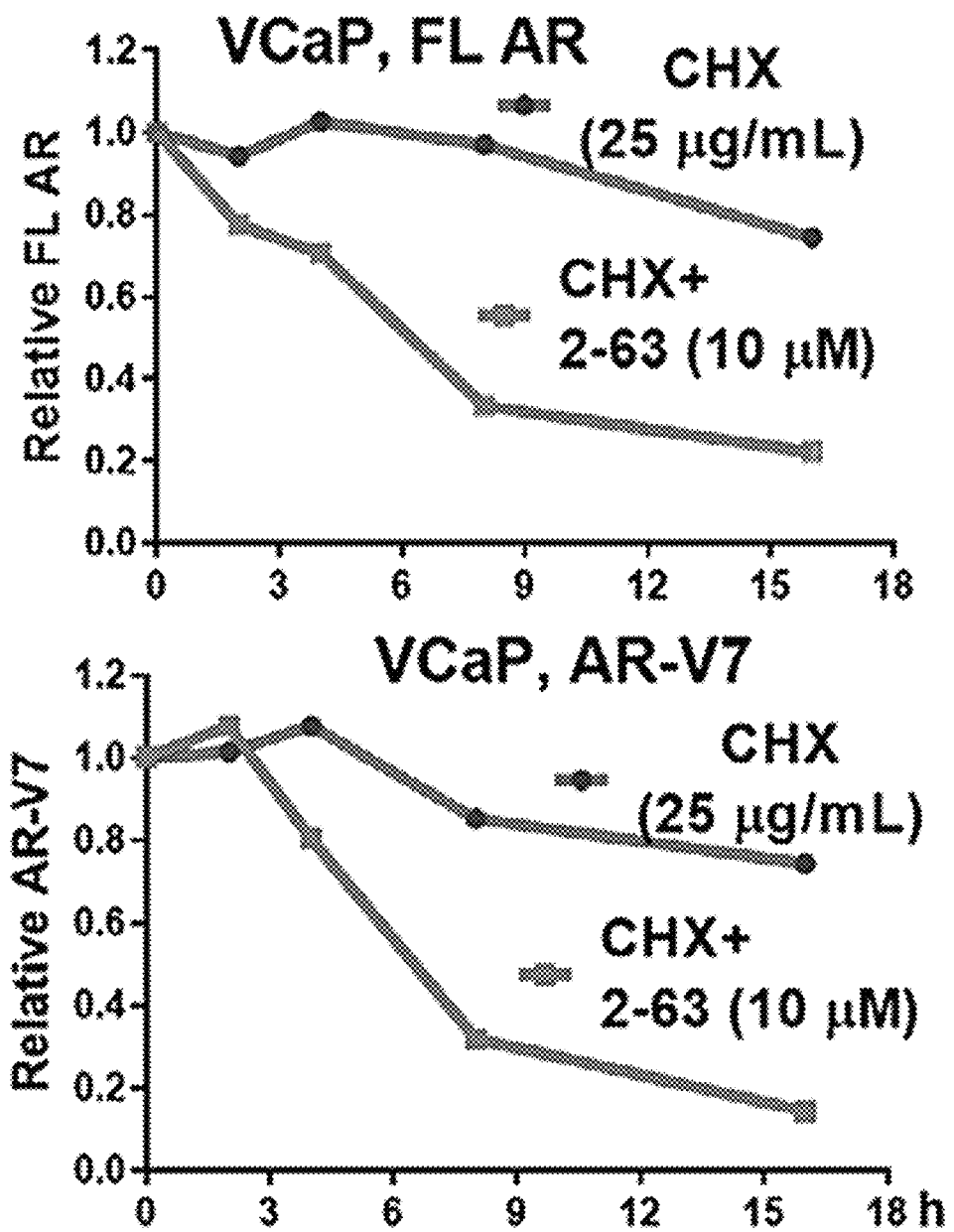

FIG. 11: 2-63 induces AR antagonism. 2-63 reduces the stability of FL AR and AR-V7. VCaP cells were treated with cycloheximide (CHX, 25 µg/mL) in the absence or presence of 2-63 (10 µM). AR and AR-V7 proteins were analyzed using Western blotting and densitometry at the indicated time points (2, 4, 8, 16 h).

Figure 12:
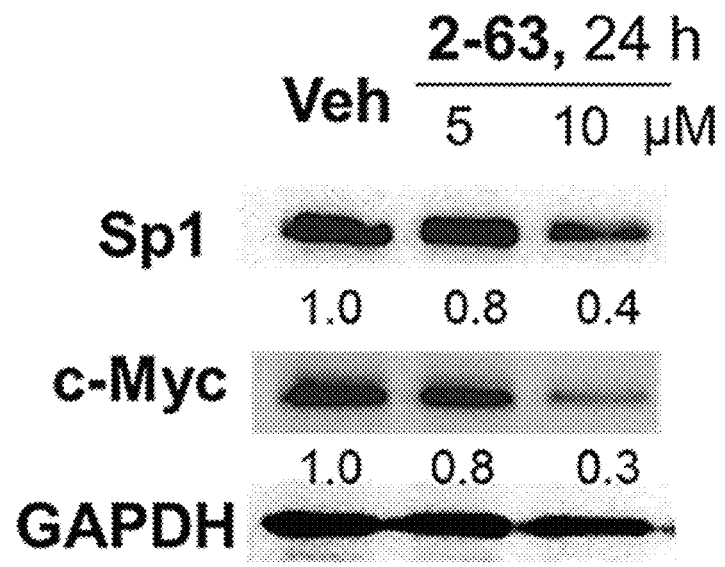

FIG. 12: 2-63 induces AR antagonism. 2-63 downregulates transcription factors Sp1 and c-Myc. VCaP cells were treated with 2-63 at 5 or 10 µM for 24 h. Sp1 and c-Myc proteins were analyzed using Western blotting. Representative images of Western blotting analysis are shown. Relative expression levels normalized against GAPDH are indicated under blots. Veh, Vehicle.

Figure 13:
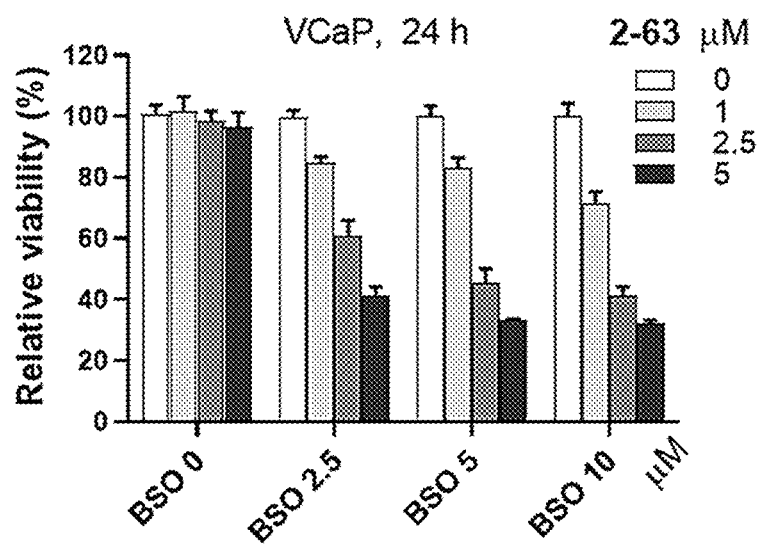

FIG. 13: Buthionine sulphoximine (BSO) significantly improves anti-PCa activities of 2-63. Combinatorial treatments were conducted by pretreating cells with BSO for 16 h, followed by drugs (2-63, 11b, or PEITC-NAC) for 24 h at the indicated concentrations. Viability was measured using an MTT assay (n=6-8) in FIGS. 16, 19, and 22, the data reflect mean±SD. 2-63 (1-5 µM) plus BSO (2.5-10 µM) synergistically reduced the viability of VCaP cells.

FIG. 14: The calculated interaction index of 2-63 and BSO in treating VCaP and 22Rv1 cells. The interaction index is defined as (% viable cells treated with drug combination)/[(% viable cells treated with drug 1)×(% viable cells treated with drug 2)].

Figure 15:
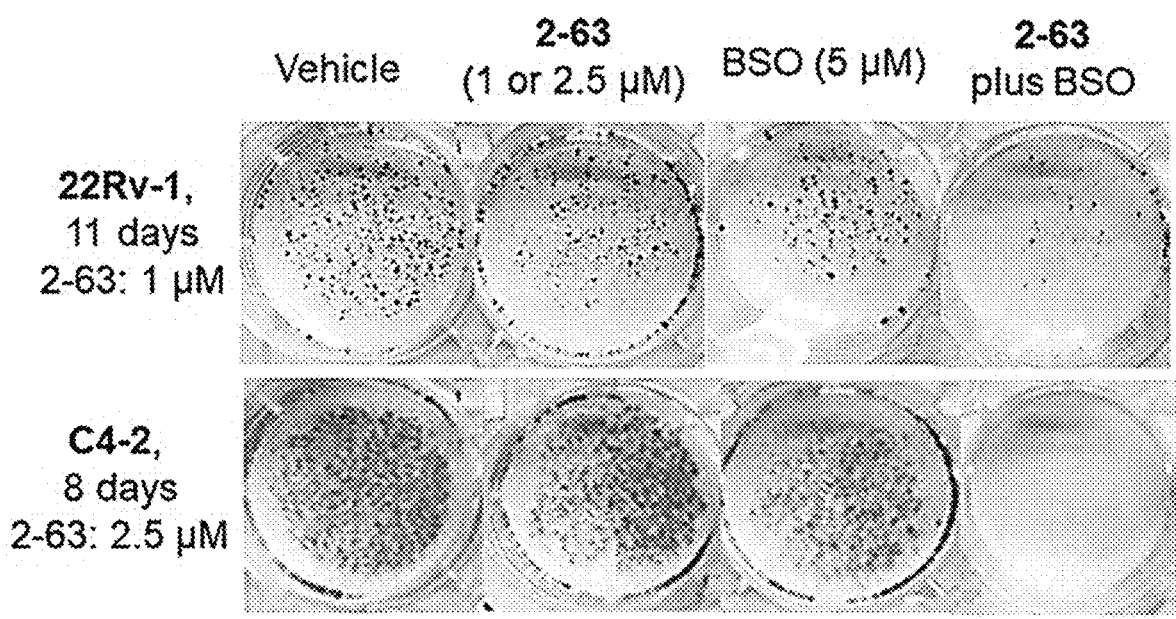

FIG. 15: BSO significantly improves anti-PCa activities of 2-63. 2-63 (1 µM in 22Rv1; 2.5 µM in C4-2) plus BSO (5 µM) combination effectively inhibits colony formation of C4-2 and 22Rv1 cells (1000 cell/well). Cells were treated for 24 h and then grown in drug-free media.

Figure 16:
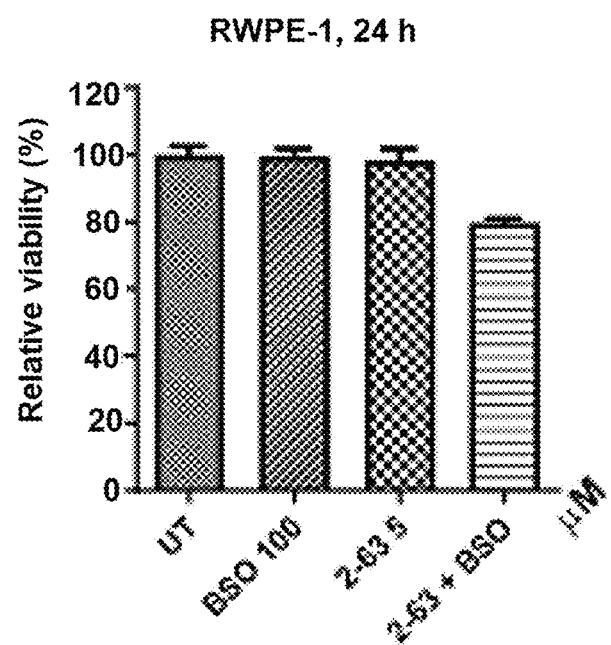

FIG. 16: BSO significantly improves anti-PCa activities of 2-63. Combinatorial treatments were conducted by pretreating cells with BSO for 16 h, followed by drugs (2-63, 11b, or PEITC-NAC) for 24 h at indicated concentrations. Viability was measured using an MTT assay (n=6-8) in FIGS. 13, 16 and 19, data reflect mean±SD. Noncancerous RWPE-1 cells are much less affected by the drug combination.

Figure 17:
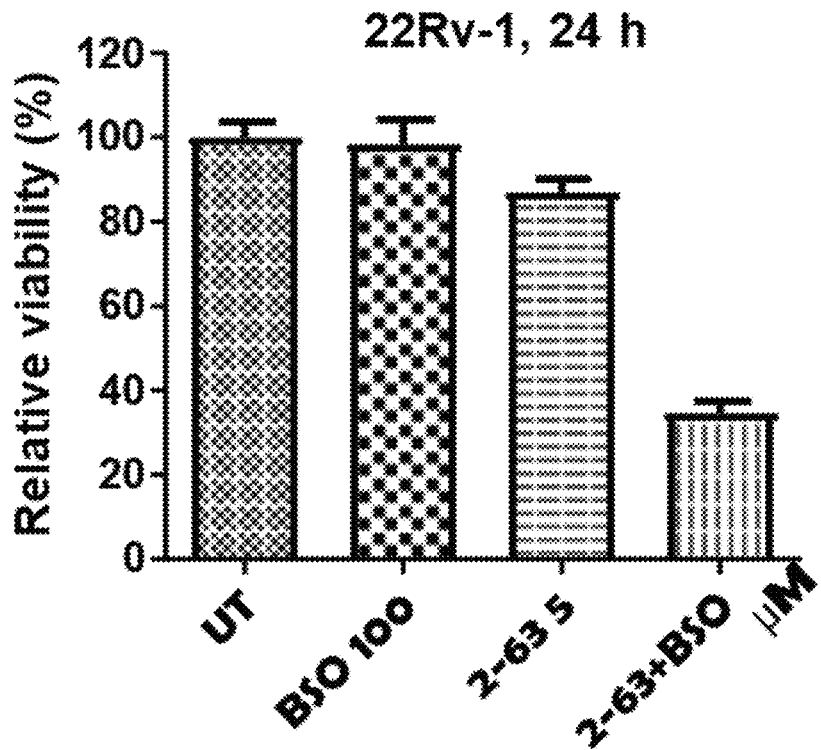

FIG. 17: BSO improves anti-PCa potency of 2-63 in 22Rv1 and C4-2 cells. Combinatorial treatments were conducted by pretreating cells with BSO for 16 h, followed by drugs (2-63, 11 b, or PEITC-NAC) for 24 h at the indicated concentrations. Viability was measured using an MTT assay (n=6-8) in FIGS. 17, 18, and 20. Data reflect mean±SD.

Figure 18:
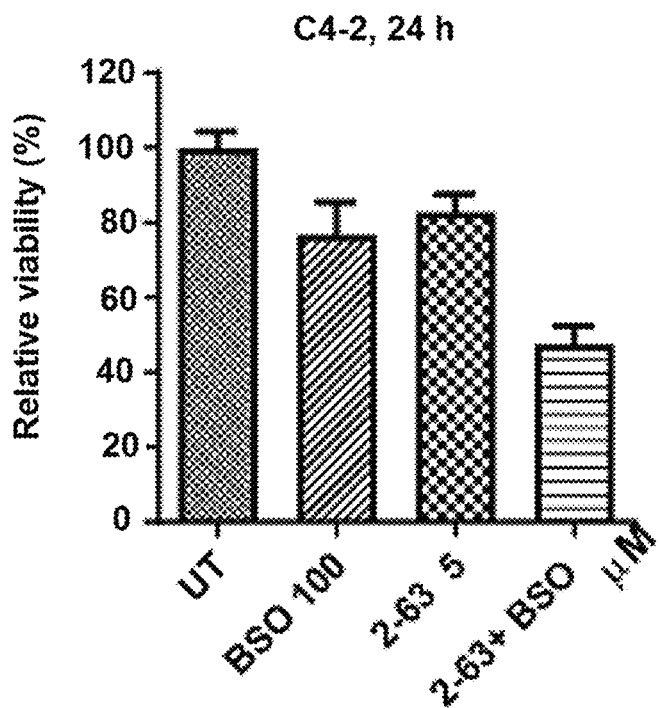

FIG. 18: BSO improves anti-PCa potency of 2-63 in 22Rv1 and C4-2 cells. Combinatorial treatments were conducted by pretreating cells with BSO for 16 h, followed by drugs (2-63, 11 b, or PEITC-NAC) for 24 h at the indicated concentrations. Viability was measured using an MTT assay (n=6-8) in FIGS. 17, 18, and 20. Data reflect mean±SD.

Figure 19:
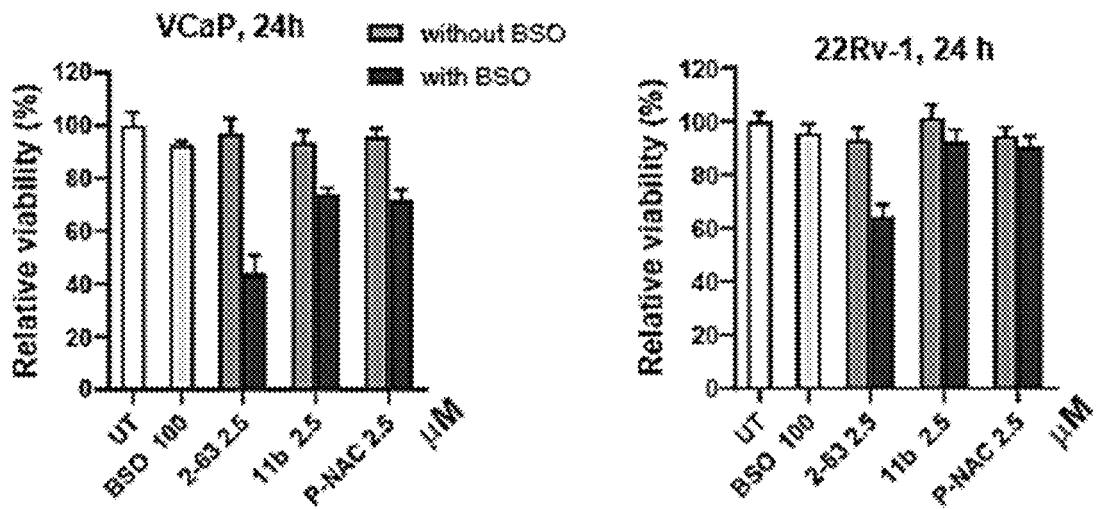

FIG. 19: BSO significantly improves anti-PCa activities of 2-63. Combinatorial treatments were conducted by pretreating cells with BSO for 16 h, followed by drugs (2-63, 11b, or PEITCNAC) for 24 h at the indicated concentrations. Viability was measured using an MTT assay (n=6-8) in FIGS. 13, 16, and 19, data reflect mean±SD. 2-63 scaffold is a better "carrier" of ITC.

Figure 20:
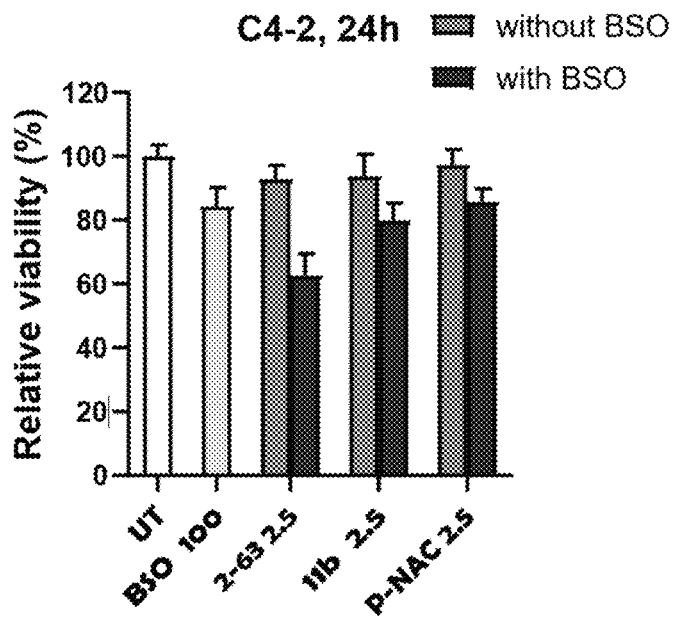

FIG. 20. BSO improves anti-PCa potency of 2-63 in 22Rv1 and C4-2 cells. Combinatorial treatments were conducted by pretreating cells with BSO for 16 h, followed by drugs (2-63, 11 b, or PEITC-NAC) for 24 h at the indicated concentrations. Viability was measured using an MTT assay (n=6-8) in FIGS. 17, 18, and 20. Data reflect mean±SD.

Figure 21:
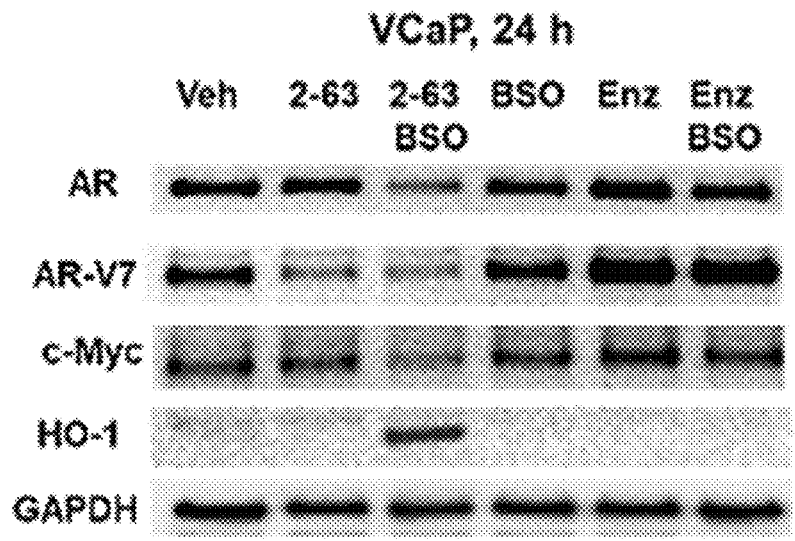

FIG. 21: BSO significantly improves anti-PCa activities of 2-63. Combinatorial treatments were conducted by pretreating cells with BSO for 16 h, followed by drugs (2-63, 11b, or PEITCNAC) for 24 h at the indicated concentrations. Viability was measured using an MTT assay (n=6-8) in FIGS. 13, 16, and 19, data reflect mean±SD. 2-63 plus BSO effectively downregulates AR, c-Myc, and upregulates HO-1. AR, AR-V7, c-Myc, HO-1, and GAPDH (loading control) proteins were analyzed using Western blotting. Representative images of the Western blotting analysis are shown. P-NAC, PEITC-NAC.

Figure 22:
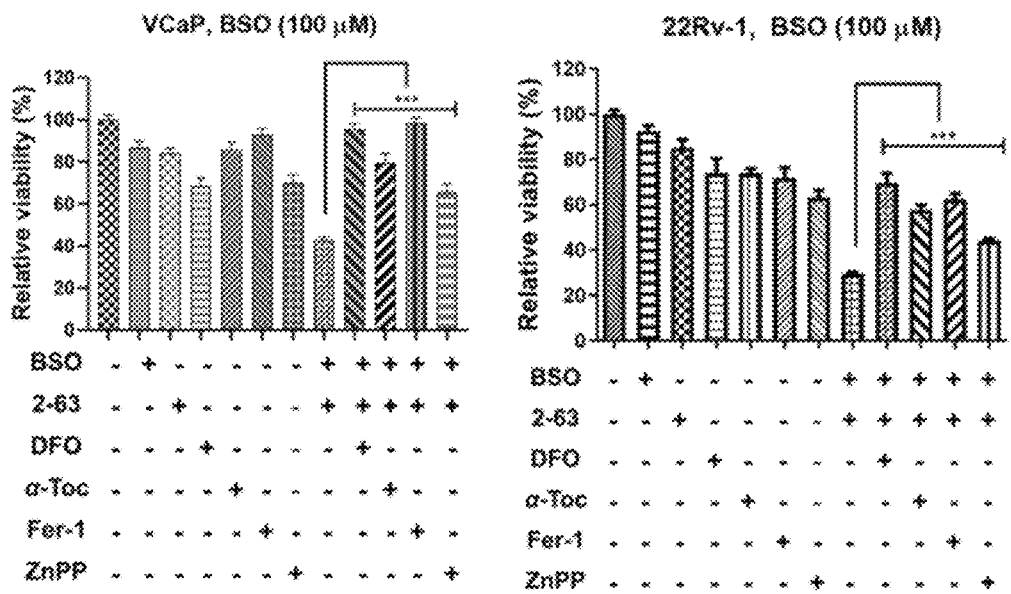

FIG. 22: 2-63 induces ferroptosis in GSH-deficient PCa cells. 2-63 plus BSO-caused viability loss is rescued by antioxidants, an iron chelator, and HO-1 inhibitor. VCaP or 22Rv1 cells were treated with 2-63 (VCaP, 2.5 µM; 22Rv1, 5 µM), deferoxamine (DFO) (100 µM), α-Tocopherol (α-Toc, 100 µM), ferrostatin-1 (Fer-1, 0.5 µM) or ZnPP (3 µM) individually or in combination for 24 h. BSO (100 µM) was added 16 h prior to other agents. Values stand for mean±SD (n=6-8).

Figure 23:
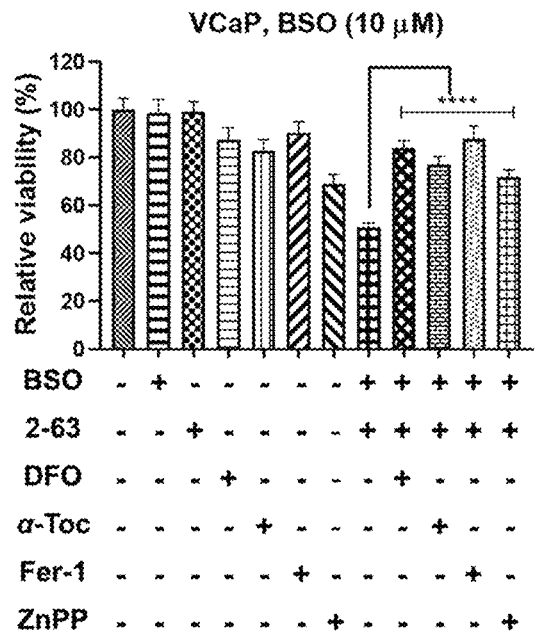

FIG. 23: 2-63 and BSO combination induces ferroptosis in PCa cells. 2-63 plus BSO-caused viability loss is rescued by antioxidants, an iron chelator, and HO-1 inhibitor. VCaP or 22Rv1.

Figure 24:
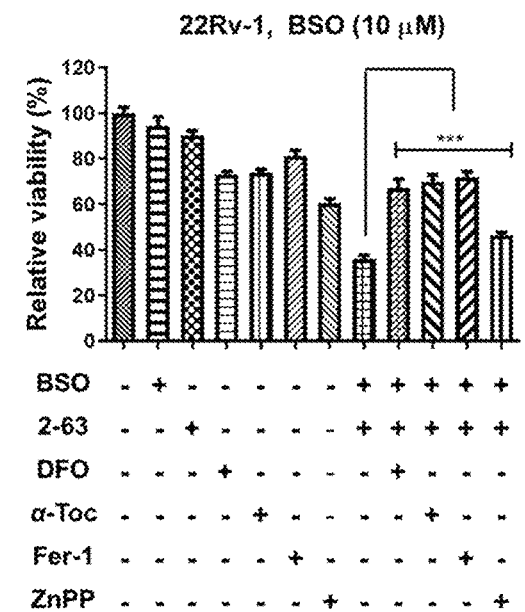

FIG. 24: 2-63 and BSO combination induces ferroptosis in PCa cells. 2-63 plus BSO-caused viability loss is rescued by antioxidants, an iron chelator, and HO-1 inhibitor. Cells were treated with 2-63 (VCaP, 2.5 µM; 22Rv1, 5 µM), DFO (10 µM), α-Tocopherol (αToc, 100 µM), ferrostatin-1 (Fer-1, 0.5 µM) or ZnPP (3 µM) individually or in combination for 24 h. BSO (10 µM) was added 16 h prior to other agents. Values stand for mean±SD (n=6-8).

Figure 25:
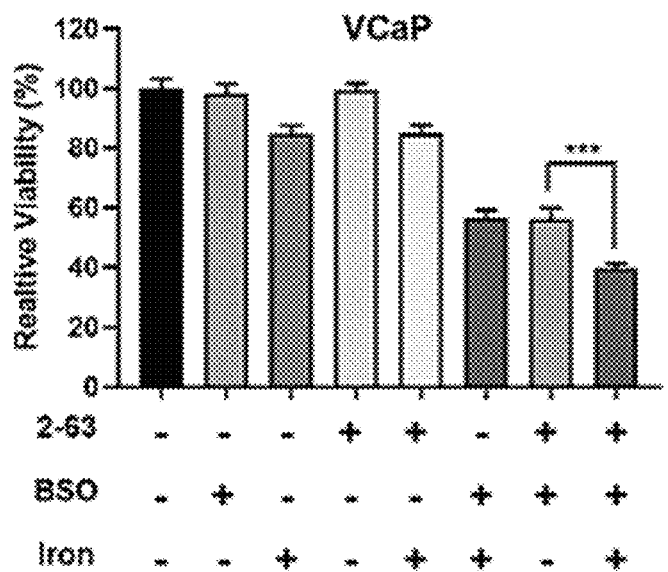

FIG. 25: 2-63 induces ferroptosis in GSH-deficient PCa cells. Exogenous iron further enhances the potency of 2-63 plus BSO combination in PCa cells. VCaP cells were treated with 2-63 (1 µM), BSO (100 µM), and ferric ammonium citrate (iron, 25 µM) individually or in combination for 24 h. BSO was added 16 h prior to other agents. Values stand for mean±SD (n=6-8).

Figure 26:
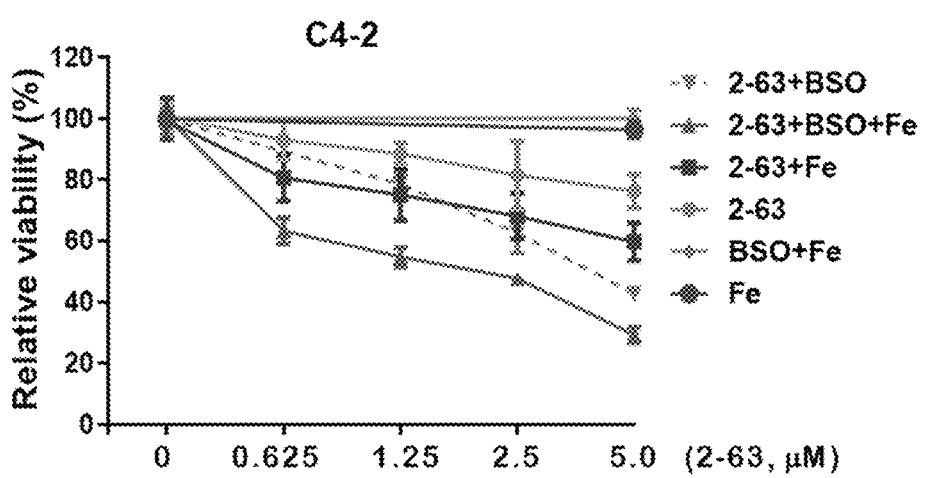

FIG. 26: 2-63 and BSO combination induces ferroptosis in PCa cells. 2-63 plus BSO-caused viability loss is rescued by antioxidants, an iron chelator, and HO-1 inhibitor. Exogenous iron (ferric ammonium citrate, 25 µM) enhances the potency of 2-63 plus BSO combination in C4-2 cells.

Figure 27:
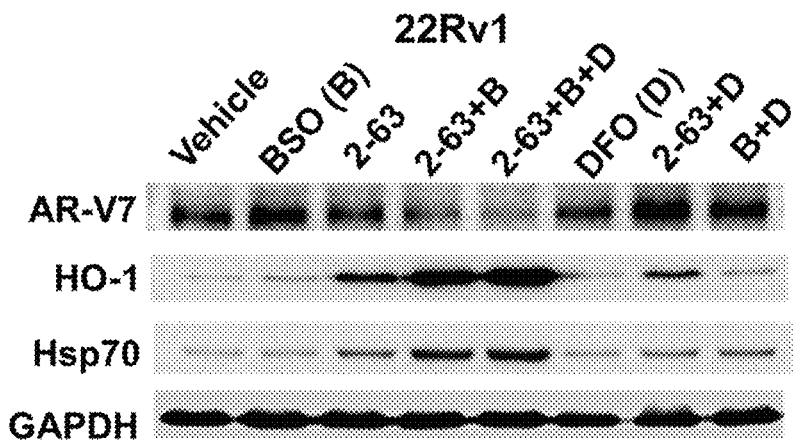

FIG. 27: 2-63 and BSO combination effectively downregulates AR-V7, upregulates Hsp70, and HO-1. The ferroptosis-preventing agent DFO neither recovers AR-V7 nor prevents the increased expression of Hsp70 and HO-1. 22Rv1 cells were pre-treated with BSO (B, 100 µM) for 6 h followed by 2-63 (2.5 µM), DFO (D, 100 µM) individually or in combination for 24 h. AR, ARV7, HO-1, Hsp70, and GAPDH (loading control) proteins were analyzed using Western blotting. Representative images of Western blotting analysis are shown.

Figure 28:
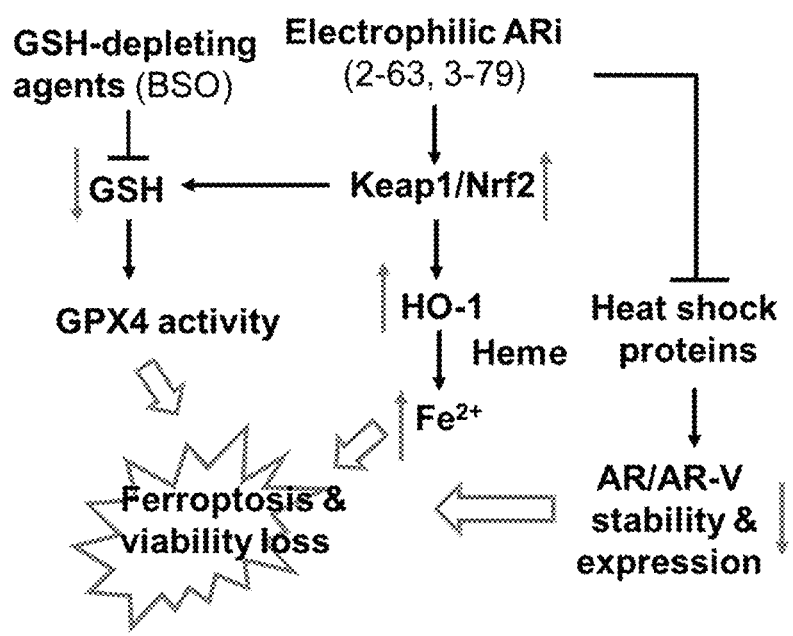

FIG. 28: ITC-ARi (2-63) and BSO combination induces ferroptosis and downregulates AR/ARV in PCa cells. GSH deficiency enhances drug accessibility to cellular targets (AR, Keap-1, heat shock proteins, etc.), increases the potency of electrophilic AR inhibitor in HO-1 upregulation that expands the intracellular Fe2+ pool, and removes the reducing equivalent of GPX4 enzyme.

Figure 29:
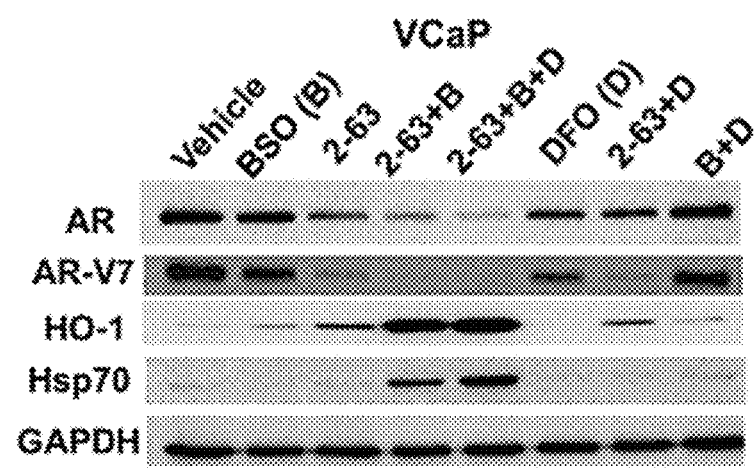

FIG. 29: 2-63 induces ferroptosis in GSH-deficient PCa cells. AR depletion is not affected by ferroptosis-rescuing agents DFO or Fer-1.

Figure 30:
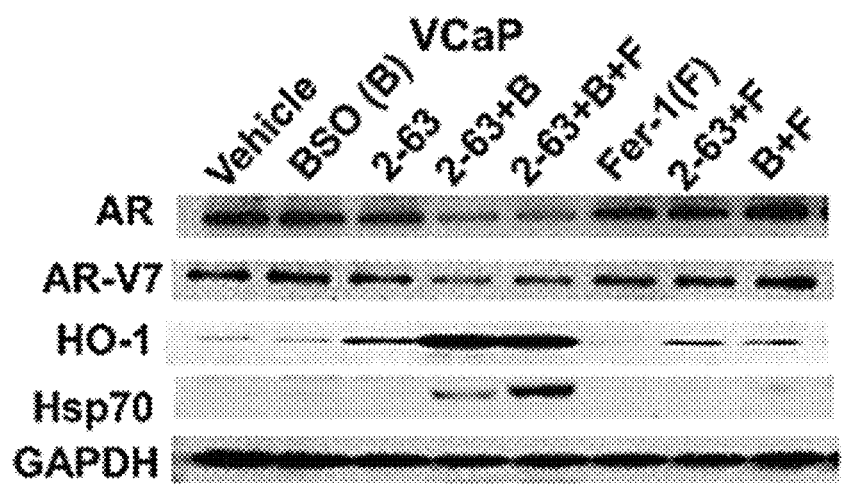

FIG. 30: 2-63 induces ferroptosis in GSH-deficient PCa cells. AR depletion is not affected by ferroptosis-rescuing agents DFO. VCaP cells were pre-treated with BSO (B, 100 µM) for 6 h followed by 2-63 (2.5 µM), DFO (D, 100 µM), and Fer-1 (F, 1 µM) individually or in combination for 24 h. AR, AR-V7, HO-1, Hsp70, and GAPDH (loading control) proteins were analyzed using Western blotting. Representative images of the Western blotting analysis are shown.

Figure 31:
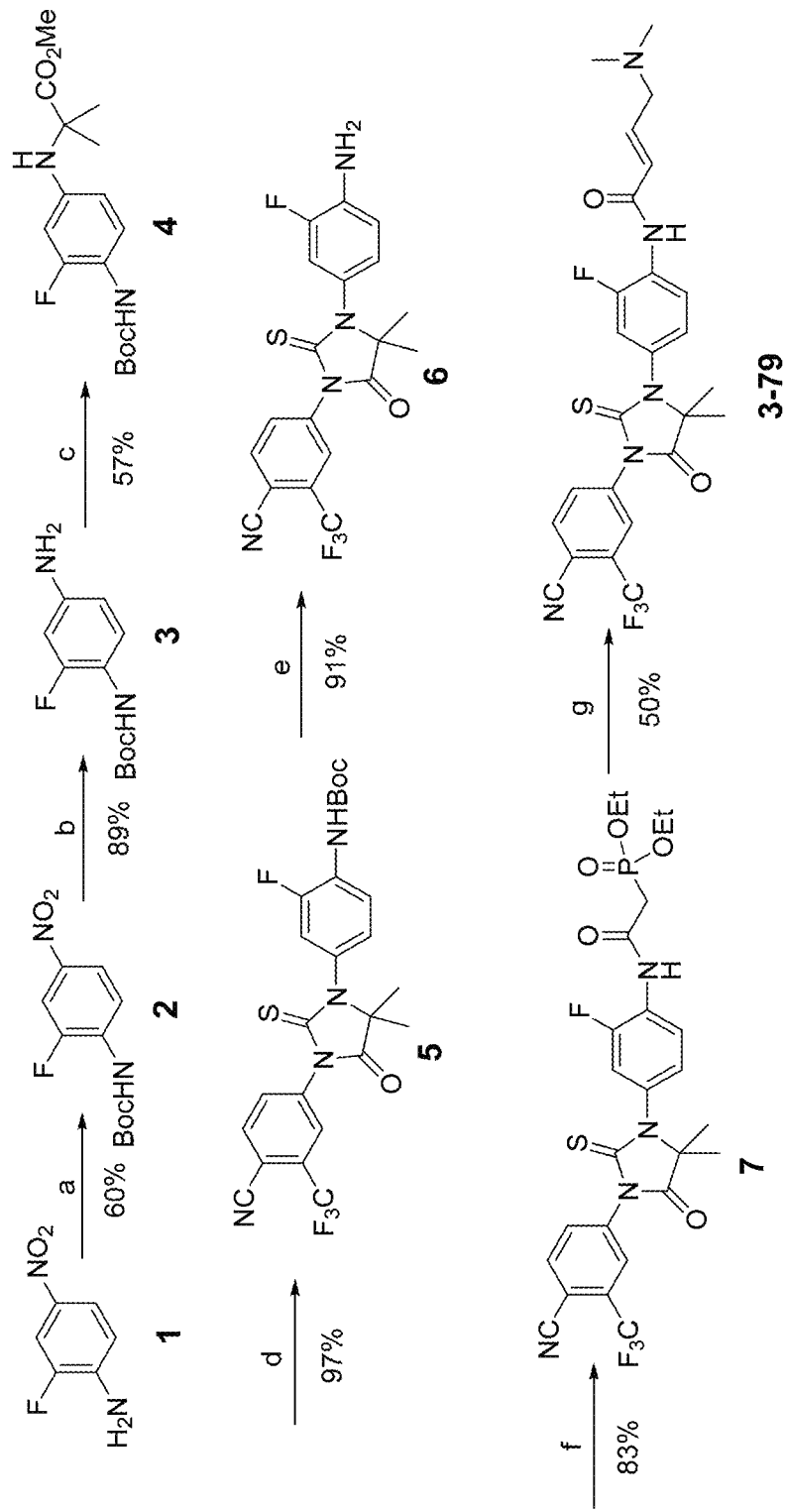

FIG. 31: The design and synthesis of 3-79, an electrophilic analogue of enzalutamide (FDA-approved AR inhibitor). The reagents and conditions are: a) (Boc)$_2$O, TEA, DMAP, DCM; b) ammonium formate, Pd/C (10%), isopropanol/H$_2$O; c) methyl 2-bromoisobutyrate, NaOAc, MeOH, reflux; d) ITC, DMSO, 80° C.; e) TFA, DCM; f) 2-(diethoxyphosphoryl)acetic acid, EDCI, DMAP, DCM; g) 2-(dimethylamino)acetaldehyde hydrochloride, DBU, THF, 50%. 1) 2-fluoro-4-nitroaniline; 2) Tert-butyl (2-fluoro-4-nitrophenyl)carbamate; 3) Tert-butyl (4-amino-2-fluorophenyl)carbamate; 4) Methyl 2-((4-((tert-butoxycarbonyl)amino)-3-fluorophenyl)amino)-2-methylpropanoate; 5) tert-Butyl (4-(3-(4-cyano-3-(trifluoromethyl)phenyl)-5,5-dimethyl-4-oxo-2-thioxoimidazolidin-1-yl)-2-fluorophenyl)carbamate; 6) 4-(3-(4-amino-3-fluorophenyl)-4,4-dimethyl-5-oxo-2-thioxoimidazolidin-1-yl)-2-(trifluoromethyl)benzonitrile; 7) Diethyl (2-((4-(3-(4-cyano-3-(trifluoromethyl)phenyl)-5,5-dimethyl-4-oxo-2-thioxoimidazolidin-1-yl)-2-fluorophenyl)amino)-2-oxoethyl)phosphonate; and 3-79) (E)-N-(4-(3-(4-cyano-3-(trifluoromethyl)phenyl)-5,5-dimethyl-4-oxo-2-thioxoimidazolidin-1-yl)-2-fluorophenyl)-4-(dimethylamino)but-2-enamide.

Figure 32:
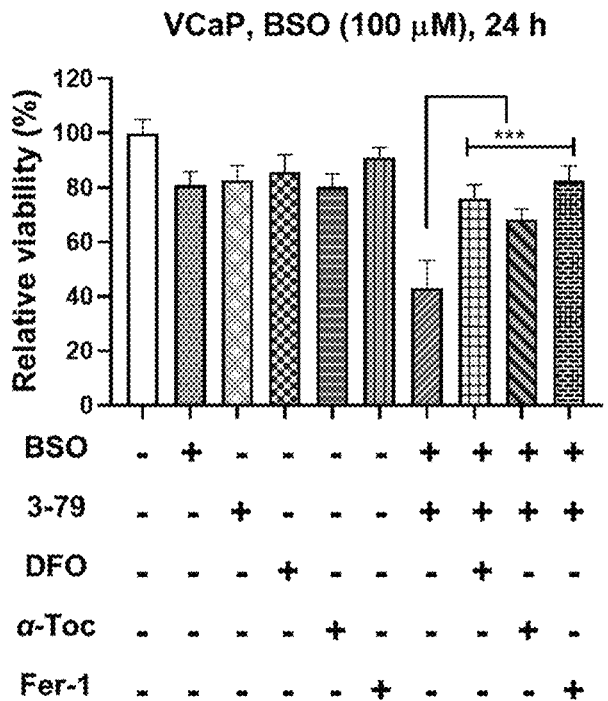

FIG. 32: 3-79 and BSO effectively reduce the viability of VCaP cells. Very similar to the combination of 2-63 and BSO, the potency of 3-79 in viability suppression is also increased under GSH deficient condition. The viability loss of VCaP cells is rescued by antioxidants and iron chelators. 3-79 (10 µM) plus BSO (100 µM)-induced viability loss was rescued by DFO (100 µM), α-Tocopherol (α-Toc, 100 µM), and Ferrostatin-1 (Fer-1, 0.5 µM). Data (n=6-8) represent mean±SD obtained from MTT assay. Statistical significance was assessed by using two-tailed Student's t-tests, and ***indicates a P<0.001.

Figure 33:
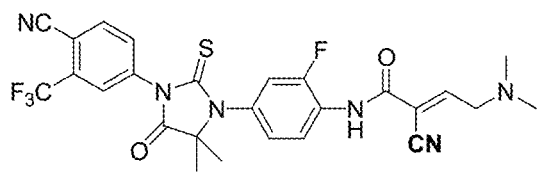
Figure 33:
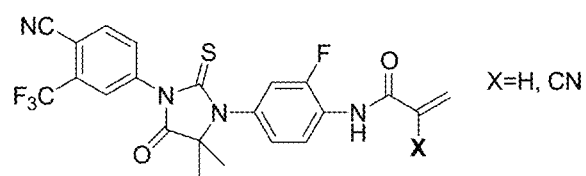
Figure 33:
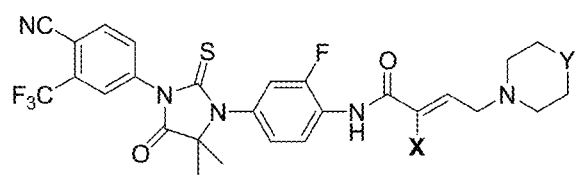

FIG. 33: Analogues of 3-79.

DETAILED DESCRIPTION

Prostate cancer (PCa) is the second leading cause of cancer-related deaths in men in the United States (Siegel, et al., (2015). Cancer statistics, 2015. CA: a cancer journal for clinicians 65, 5-29). PCa is initially managed with surgery, radiation, androgen antagonists (e.g., bicalutamide), and surgical or chemical castration. However, the relapsed or metastatic disease post-castration (castration-resistant prostate cancer or CRPC) has a poor prognosis with most patients dying within 2 years (Karantanos, et al., (2015). European urology 67, 470-479). Innovative treatment approaches are urgently needed to treat CRPC patients.

AR signaling is a major driving force in all stages of PCa (Chen, et al., (2009). The lancet oncology 10, 981-991). CRPC cells evolve mechanisms to re-activate AR signaling under androgen deprivation conditions (Mitsiades, N, Cancer Res 2013; 73(15): 4599-605). These mechanisms include overexpression and gain-of-function mutations of AR (Joseph, et al., (2013). Cancer discovery 3, 1020-1029; Korpal, et al., Cancer Discov. 2013, 3, 1030-1043), expression of AR splice variants (AR-Vs) (Li, et al., (2013). Cancer research 73, 483-489), compensatory cross-talk between AR and other signaling pathways (Liu, et al., (2014). Current pharmaceutical design 20, 2912-2921) and enhanced intratumoral androgen biosynthesis (Nakamura, et al., (2005). Endocrine-related cancer 12, 101-107). Enzalutamide (Enz, FIG. 1A) is a newly FDA-approved AR inhibitor that prolongs the survival of CRPC patients (Beer, et al., (2014). The New England journal of medicine 371, 424-433; Scher et al., 2012). Enz competitively binds to AR with 5-8 fold higher affinity than bicalutamide and, in contrast to bicalutamide, does not promote AR nuclear translocation (Tran, et al., (2009). Science 324, 787-790). Nevertheless, acquired resistance to Enz typically develops within months and is associated with a relatively short-lived patient survival benefit. Indeed, well-established CRPC cell line models that either vastly overexpress AR (e.g., VCaP, C4-2 cells) or over-express AR splice variants (e.g., 22Rv1 cells), presumably in combination with changes in other cellular signaling pathways, are resistant to Enz while remaining addicted to AR. Therefore, drugs that can more effectively antagonize AR signaling in CRPC cells are desirable.

Isothiocyanates (ITCs), such as phenethyl ITC (PEITC) and sulforaphane (SFN), are bioactive metabolites of naturally occurring glucosinolates existing in cruciferous vegetables (e.g., broccoli, cabbage, watercress, etc.). Epidemiological studies demonstrate a positive correlation between cruciferous vegetable consumption and decreased incidence of PCa, and ITCs are one of the major dietary components contributing to this health benefit. In recurrent PCa patients, SFN-enriched broccoli sprout extracts prolonged PSA (i.e., prostate-specific antigen) doubling time without severe adverse events, indicating a potential for further dose escalation.

The current disclosure provides a novel class of drugs designed by incorporating an ITC moiety into the chemical scaffolds of an AR inhibitor with, in certain examples, full length (FL) AR binding affinity as multifunctional hybrid anti-prostate cancer agents. The hybrid drugs can have electrophilicity blocked or reduced with an agent such as N-acetyl cysteine and can be administered in combination with a glutathione (GSH)-depleting agent. Administration, in combination with a GSH-depleting agent, creates synergistic anti-cancer effects. Importantly, the drug conjugates and combination treatments described herein can result in cancer cell destruction through ferroptosis rather than apoptosis, providing a treatment modality against apoptosis-resistant cancer cells. The current disclosure also provides compositions, including the novel drugs and methods of using the compositions to treat AR positive cancers such as prostate cancer.

Aspects of the current disclosure are now described with additional detail and options as follows: (i) Exemplary AR Inhibitors, ITC, Electrophilicity Reducing Agents and GSH-Depleting Agents; (ii) Compositions for Administration; (iii) Methods of Use; (iv) Kits; (v) Exemplary Embodiments; (vi) Experimental Examples; and (vii) Closing Paragraphs.

(i) Exemplary AR Inhibitors, ITC, Electrophilicity-Reducing Agents and GSH-Depleting Agents. AR inhibitors can include AR antagonists or AR degraders. AR antagonists reduce or block the activity of AR by inhibiting AR binding and/or otherwise functionally disrupting AR signaling. AR degraders result in the physical breakdown of the AR receptor.

Examples of AR inhibitors include abiraterone (or CB-76 30; (3S,8R,9S, 1 OR, 13S, 14S)-10,13-dimethyl-17-(pyridin-3-yl) 2,3,4,7,8,9,10,11,12,13,14,15-dodecahydro-1H-cyclopenta [a]phenanthren-3-ol); apalutamide (ERLEADA, Janssen Biotech, Inc); ARN-509; ASC-J9; bevacizumab (Avastin; a monoclonal antibody that recognizes and blocks vascular endothelial growth factor A (VEGF-A)); bexlosteride (LY-191,704; (4aS,10bR)-8-chloro-4-methyl-1,2,4a, 5,6,10b-hexahydrobenzo[f]quinolin-3-one); bicalutamide (N-[4-cyano-3-(trifluoromethyl)phenyl]-3-[(4-fluorophenyl)sulfonyl]-2-hydroxy-2-methylpropanamide); cabazitaxel (XRP-6258); cyproterone acetate (6-chloro-ip,2p-dihydro-17-hydroxy-3'H-cyclopropa[1,2]pregna-4,6-diene-3, 20-dione); darolutamide (NUBEQA; also, Keto-darolutamide which is a metabolite of Darolutamid); docetaxel (Taxotere; 1,7β,10β-trihydroxy-9-oxo-5β,20-epoxytax-11-cnc-2a,4,13a-triyl 4-acetate 2-benzoate 13-{(2R, 3S)-3-[(tert-butoxycarbonyl)amino]-2-hydroxy-3-phenylpropanoate}); dutasteride (Avodart; N-[2,5-Bis(trifluoromethyl)phenyl]-3-oxo-4-aza-5α-androst-1-ene-17β-carboxamide); enzalutamide (MDV3100; (4-(3-(4-cyano-3-(trifluoromethyl)phenyl)-5,5-dimethyl-4-oxo-2-thioxoimidazolidin-1-yl)-2-fluoro-N-methyl benza mide)); FCE 28260; finasteride (Proscar, Propecia; N-tert-Butyl-3-oxo-4-aza-5α-androst-1-ene-1713-carboxamide or N-(1,1-dimethylethyl)-3-oxo-(5a, 17P)-4-azaandrost-1-ene-17-carboxamide); flutamide (2-methyl-N-[4-nitro-3-(trifluoromethyl)phenyl]-propanamide); galeterone; hydroxyflutamide; izonsteride (LY-320,236; (4aR, 10bR)-8-[(4-ethyl-1,3-benzothiazol-2-yl)sulfanyl]-4,1 Ob-dimethyl-1,4,4a,5,6,10b-hexahydrobenzo[f]quinolin-3(2H)-one); MDX-010 (Ipilimumab, a fully human monoclonal antibody that binds to and blocks the activity of CTLA-4); nilutamide (5,5-dimethyl-3-[4-nitro-3-(trifluoromethyl)phenyl] imidazolidine-2,4-dione); ODM-201; OSU-HDAC42 ((S)-(-r)-N-hydroxy-4-(3-methyl-2-phenylbutyrylamino)-benzamide); SKF105, 111; sunitumib (N-(2-diethylaminoethyl)-5-[(Z)-(5-fluoro-2-oxo-1H-indol-3-ylidene)methy 1]-2,4-dimethyl-1H-pyrrole-3-carboxamide); turosteride ((4aR,4bS,6aS,7S, 9aS,9bS,11aR)-1,4a,6a-trimethyl-2-oxo-N-(propan-2-yl)-N-(propan-2ylcarbamoyl)hexadecahydro-1H-indeno[5,4-f] quinoline-7-carboxamide); vitaxin (a monoclonal antibody against the vascular integrin αvβ3); and ZD-4054 (N-(3-methoxy-5-methyl-2-pyrazinyl)-2-[4-(1,3,4-oxadiazol-2-yl) phenyl]-3-pyridinesulfonamide. For additional information regarding AR inhibitors, see Crona, et al., *Clin Pharmacol Ther.* 2015; 98(6):582-589; Njar, et al., *Translational Cancer Research.* 2017; 6, S7; Beretta, et al., *Frontiers in chemistry* vol. 7 369. 28 May 2019; Agnese, et al., *J Cancer Metastasis Treat* 2017; 3:328-61; U.S. Pat. No. 9,289, 436B2; and AU2015266654A1.

Particular examples of AR degraders include proteolysis targeting chimera-like molecules (PROTAC) that recruit an E3 ligase for AR degradation. 2-63, disclosed herein, can act as one such AR degrader under GSH-deficient conditions described herein. 2-63 has a molecular weight of 694.2, well below the molecular weight of other PROTAC published thus far.

Examples of ITC include phenethyl-ITC, sulforaphane, erysolin, erucin, iberin, alyssin, berteroin, iberverin, cheirolin, 5-methylsulfinylpentyl-ITC, 6-methylsulfinylhexyl-ITC, 7-methylsulfinylheptyl-ITC, 8-methylsulfinyloctyl-ITC (hirsutin), 9-methylsulfinylnonyl-ITC, 10-methylsulfinyldecyl-ITC, phenylethyl-ITC, 4-(α.-L-rhamnopyranosyloxy)benzyl-ITC, 3-(α-L-rhamnopyranosyloxy)benzyl-ITC, 2-(α-L-rhamnopyranosyloxy)benzyl-ITC, and 4-(4'-O-acetyl-α-L-rhamnopyranosyloxy)benzyl-ITC.

In certain examples, ITC-AR inhibitor conjugates described herein bind the FL AR with the same or substantially the same affinity as its natural androgen ligand. The affinity of a molecule X for its partner Y can generally be represented by the dissociation constant ($K_D$) or the association constant ($K_A$). Affinity can be measured by common methods known in the art. In particular embodiments, "substantially the same" means within 10%, within 5%, or within 2%.

Particular embodiments include an ITC-AR inhibitor conjugate with reduced or blocked electrophilicity. Electrophilicity is a property of an atom or compound that results from an area of the molecule, which is electrophilic (an electron-poor region of a molecule accepting a pair of electrons to form a bond). To reduce the electrophilicity of isothiocyanate and prevent bond formation, substituents can be introduced at the α-position, β-position, and γ-position of the isothiocyanate group, which will create a steric hindrance. Additionally, an electron-donating substituent can be added to the isothiocyanate compound. A compound in which the electrophilicity of the isothiocyanate group is reduced is preferable. A compound having an electron-donating substituent having a large steric hindrance at the α-position, β-position, and γ-position of the isothiocyanate group is also preferable. For information regarding compounds that can be used to block the electrophilicity of ITCs, see JP5493856B2.

In particular embodiments, NAC is used to block or reduce the electrophilicity of ITCs. In particular embodiments, electrophilicity blocking agents include a compound with a free thiol.

Examples of ITC compounds with reduced or blocked electrophilicity include 4,4'-diphenylmethane di-ITC, 4,4'- methylenebis (2,6-diethylphenyl-ITC), 4,4'-methylenebis (2,6-di-t-butylphenyl-ITC) 1,3-bis (isothiocyanatomethyl) cyclohexane, 1,3-propanedi-ITC, 1,5-pentanedi-ITC, 1,7-heptanedi-ITC, 1,9-nonane ITC, and 1,11-undecanedi-ITC. For additional information regarding compounds that can be used to block the electrophilicity of ITCs, see JP5493856B2.

In particular embodiments, the GSH-depleting agent is BSO. Additional examples of GSH-depleting agents include: Imidazole Ketone Erastin, diethylmaleate, phorone, 2-acetylamino-3-[4-(2-acetylamino-2-carboxyethylsulfa-nylthiocarboniamino) phenyl thiocarbamolyl, Sulfanyl] propionic acid (2-AAPA), sulfasalazine, piperonmin, N-ethyl maleimide, N-pyrenyl maleimide, 2-AAPA, elastin, sorafenib, 1S, 3R-RSL3, DPI19, DPI18, DPI17, DPI13, DPI12, DPI10 (ML210), DPI7 (ML162), altoretamine, and/or their pharmaceutically acceptable salts may be included, N-[2-(allyloxy) benzyl]-N-1,3-benzodioxol-5-yl-2-chloro-acetamide, 6-(chloromethyl)-N-(2-naphthyl)-1,3,5-triazine-2,4-diamine, 6-(chloromethyl)-N-(4-ethoxyphenyl)-1,3,5-triazine-2,4-diamine, 2-chloro-N-heptyl-N-m-tolyl-acetamide, Bcl-2 antisense oligodeoxynucleotide, an inhibitor of multidrug resistance protein 1, an inhibitor of the gamma-glutamyl transpeptidase, an inhibitor of cystine uptake, disodium glutathione disulfide, phenethyl ITC, glucocorticoid receptor antagonist, an anti-IL-6 agent, NPD926, parthenolide, piperlongumine, an inhibitor of a protein from the bromodomain and extraterminal domain family, in particular GSK525762A or I-BET762.

In particular embodiments, a GSH-depleting agent is one that induces ferroptosis and slows tumor growth. In particular compounds, a GSH-depleting agent is one that induces cellular oxidative stress. In particular embodiments, a GSH-depleting agent is one that reduces or inhibits neutrophil sequestration at the inflammation site of a mammal. In particular embodiments, a GSH-depleting agent is one that reduces the level of glutathione in cancer cells. In particular compounds, a GSH-depleting agent, is one that treats and prevents cancer. For more information regarding GSH-depleting agents, see Zhang, et al. Cell Chem. Biol. 2019, 26, 623-633, US20150259309, U.S. Pat. No. 5,994,402, JP2019514962, and US20180214390.

Particular embodiments described herein include novel ferroptosis-inducing drug combinations. Without being bound by theory, in these embodiments, AR degraders also activate the Nrf2 pathway, which is pivotal for the subsequent ferroptosis induction when combined with GSH-depleting agent. AR degradation sensitizes prostate cancer cells to ferroptosis.

In particular embodiments, sulfur atoms within ITC-ARi conjugates can be replaced with selenium. In particular embodiments, the sulfur atom replaced with selenium is a double-bonded sulfur atom (see, for example, star in FIG. 1).

(ii) Compositions for Administration. The current disclosure provides compositions, including a drug and/or drug combination disclosed herein. In particular embodiments, the composition is a pharmaceutical composition including a drug and/or drug combination disclosed herein and a pharmaceutically acceptable carrier. For example, a composition disclosed herein could include a hybrid ARi (e.g., 2-63 and/or 3-79) and/or a GSH-depleting agent (e.g., BSO).

Each drug can be formulated into its own composition for administration, or the drug can be formulated with an additional active ingredient for administration as a composition. The drugs described herein, and the additional active ingredient can be formulated for use in a combination therapy.

For injection, compositions can be formulated as aqueous solutions, such as in buffers, including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the compositions.

Alternatively, the composition can be in lyophilized form and/or provided in powder form for constitution with a suitable vehicle, e.g., sterile pyrogen-free water, before use. Lyophilized compositions can include less than 5% water content, less than 4.0% water content, or less than 3.5% water content.

In particular embodiments, the composition can be in a unit dosage form, such as in a suitable diluent in sterile, hermetically sealed ampoules or sterile syringes.

In particular embodiments, in order to prolong the effect of a composition, it is desirable to slow the absorption of the active ingredient(s) following injection. Compositions can be formulated as sustained-release systems utilizing semipermeable matrices of solid polymers containing at least one administration form. Various sustained-release materials have been established and are well known by those of ordinary skill in the art. Sustained-release systems may, depending on their chemical nature, release active ingredients following administration for a few weeks up to over 100 days.

Compositions can also be formulated for oral administration. For ingestion, compositions can take the form of tablets, pills, lozenges, sprays, liquids, and capsules formulated in conventional manners. Ingestible compositions can be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable supplements with the improved mouthfeel. U.S. Pat. No. 5,965,162, relates to compositions and methods for preparing comestible units which disintegrate quickly in the mouth.

For administration by inhalation (e.g., nasal or pulmonary), the compositions can be formulated as aerosol sprays for pressurized packs or a nebulizer, with the use of suitable propellants, e.g. dichlorodifluoromethane, trichlorofluoromethane, or dichlorotetra-fluoroethane.

Nanoparticle formulations for a variety of administration routes can also be used.

Any composition described herein can advantageously include any other pharmaceutically acceptable carriers, which include those that do not produce significant adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards required by the U.S. FDA Office of Biological Standards and/or other relevant foreign regulatory agencies.

In particular embodiments, the compositions can include, for example, 25 µg/mL or mg-5 mg/mL or mg, 50 µg/mL or mg-5 mg/mL or mg, 100 µg/mL or mg-5 mg/mL or mg, 150 µg/mL or mg-5 mg/mL or mg, 200 µg/mL or mg-5 mg/mL or mg, 250 µg/mL or mg-5 mg/mL or mg, 300 µg/mL or mg-5 mg/mL or mg, 350 µg/mL or mg-5 mg/mL or mg, 400 µg/mL or mg-5 mg/mL or mg, 450 µg/mL or mg-5 mg/mL or mg, 500 µg/mL or mg-5 mg/mL or mg, 550 µg/mL or mg-5 mg/mL or mg, 600 µg/mL or mg-5 mg/mL or mg, 650 µg/mL or mg-5 mg/mL or mg, 700 µg/mL or mg-5 mg/mL or mg, 750 µg/mL or mg-5 mg/mL or mg, 800 µg/mL or mg-5 mg/mL or mg, 850 µg/mL or mg-5 mg/mL or mg, 900 µg/mL or mg-5 mg/mL or mg, 950 µg/mL or mg-5 mg/mL or mg, 1 mg/mL or mg-5 mg/mL or mg, 1.5 mg/mL or mg-5 mg/mL or mg of one or more of the active ingredients.

When formulated in a single composition for administration, an ITC-AR inhibitor conjugate (e.g., 2-63, 12a, 12b) and a GSH-depleting agent (e.g., BSO) can be included at a ratio. The ratio can be, for example, ITC-AR inhibitor conjugate to GSH-depleting agent at 1:1; 1:2; 2:1; 1:3: 3:1; 1:4; 4:1; 1:10; 10:1; 1:50; 50:1; 1:100; or 100:1.

(iii) Methods of Use. The current disclosure utilizes the compositions disclosed herein to treat a subject diagnosed with cancer. In particular embodiments, the cancer is prostate cancer. In particular embodiments, the prostate cancer is CRPC. In particular embodiments, the prostate cancer has become resistant to apoptosis-inducing agents.

As used herein, subjects include humans, veterinary animals (dogs, cats, reptiles, birds, etc.), livestock (horses, cattle, goats, pigs, chickens, etc.), and research animals (monkeys, rats, mice, fish, etc.).

Treating subjects includes delivering therapeutically effective amounts of the compositions disclosed herein. Therapeutically effective amounts can include effective amounts and therapeutic amounts.

An "effective amount" is the amount of active agent(s) or composition(s) necessary to result in a desired physiological change in a subject in vivo or in vitro. Effective amounts are often administered for research purposes. Effective amounts disclosed herein can have an effect on cell growth, for example, as determined by an MTT assay and/or colony formation assay. Cell counting as a golden standard can be performed routinely to determine cell doubling times and growth rates. Cell viability can be determined by trypan blue exclusion and LDH release assays.

Therapeutic amounts of the compositions disclosed herein can have an anti-cancer effect, particularly on AR positive cancer, including prostate cancer. Cancer (medical term: malignant neoplasm) refers to a class of diseases in which a group of cells displays uncontrolled growth (division beyond the normal limits), invasion (intrusion on and destruction of adjacent tissues), and sometimes metastasis. "Metastasis" refers to the spread of cancer cells from their original site of proliferation to another part of the body. For solid tumors, the formation of metastasis is a very complex process. It depends on the detachment of malignant cells from the primary tumor, invasion of the extracellular matrix, penetration of the endothelial basement membranes to enter the body cavity and vessels, and then, after being transported by the blood or lymph, infiltration of target organs. Finally, the growth of a new tumor, i.e., a secondary tumor or metastatic tumor, at the target site depends on angiogenesis. Tumor metastasis often occurs even after removing the primary tumor because tumor cells or components may remain and develop metastatic potential.

A "tumor" is swelling or lesion formed by an abnormal growth of cells (called neoplastic cells or tumor cells). A "tumor cell" is an abnormal cell divided by a rapid, uncontrolled cellular proliferation and continues to divide after the stimuli that initiated the new division ceases. Tumors show partial or complete lack of structural organization and functional coordination with the normal tissue. Usually, they form a distinct mass of tissue, either benign, pre-malignant, or malignant.

As used herein, an anti-cancer effect refers to a biological effect, which can be manifested by a decrease in tumor volume, a decrease in the number of cancer cells, a decrease in the number of metastases, an increase in life expectancy, or a decrease of various physiological symptoms associated with the cancerous condition. An anti-cancer effect can also be manifested by a decrease in recurrence or an increase in the time before recurrence.

For administration, therapeutically effective amounts (also referred to herein as doses) can be initially estimated based on results from in vitro assays, animal model studies, and/or preclinical studies. Such information can be used to determine useful doses in subjects of interest more accurately. Particularly useful pre-clinical tests include a measure of cell growth, cell death, and/or cell viability.

The actual dose amount administered to a particular subject can be determined by a physician, veterinarian, or researcher taking into account parameters such as physical, physiological, and psychological factors including target, body weight, stage of cancer, the type of cancer, previous or concurrent therapeutic interventions, idiopathy of the subject, and route of administration.

Exemplary doses can include 0.05 mg/kg to 10.0 mg/kg of one or more drugs disclosed herein. The total daily dose can be 0.05 mg/kg to 30.0 mg/kg of one or more drugs disclosed herein to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of administration forms of a drug using 60-minute oral, intravenous or other dosing. In one particular example, doses can be administered QD or BID to a subject with, e.g., total daily doses of 1.5 mg/kg, 3.0 mg/kg, or 4.0 mg/kg of a composition with up to 92-98% wt/v of the compounds disclosed herein.

Additional useful doses can often range from 0.1 to 5 µg/kg or from 0.5 to 1 µg/kg. In other examples, a dose can include 1 µg/kg, 5 µg/kg, 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 150 µg/kg, 200 µg/kg, 250 µg/kg, 350 µg/kg, 400 µg/kg, 450 µg/kg, 500 µg/kg, 600 µg/kg, 700 µg/kg, 800 µg/kg, 900 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, or more.

When administered as a combination therapy, an ITC-AR inhibitor conjugate (e.g., 2-63, 12a, 12b) and a GSH-depleting agent (e.g., BSO) can be administered at a ratio. The ratio can be, for example, ITC-AR inhibitor conjugate to GSH-depleting agent at 1:1; 1:2; 2:1; 1:3: 3:1; 1:4; 4:1; 1:10; 10:1; 1:50; 50:1; 1:100; or 100:1.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

The compositions described herein can be administered simultaneously or sequentially within a selected time window, such as within 10 minutes, 1 hour, 3 hours, 10 hours, 15 hours, 24 hours, or 48 hours time windows or when the complementary active ingredient is administered within a clinically-relevant therapeutic window.

Compositions can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

In particular embodiments, the compositions disclosed herein can be used in conjunction with other cancer treatments. For example, the composition disclosed herein can be administered in combination with other active ingredients, for example, an AR inhibitor (e.g., Enz, darolutamide, proxalutamide, apalutamide, biulatamide) a gonadotropin-releasing hormone agonist or antagonist (e.g., Lupron, Zoladex (Goserelin), Degarelix, Ozarelix, ABT-620 (Elagolix), TAK-385 (Relugolix), EP-100 or KLH-2109); a phosphoinositide 3-kinase (PI3K) inhibitor, a TORC inhibitor, or a dual PI3K/TORC inhibitor (e.g., BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Ca1101, PWT33597, LY-317615 (enzastaurin hydrochloride), CU-906, or CUDC-907); a CYP17 inhibitor in addition to Galeterone (e.g., abiraterone acetate (Zytiga), TAK-700 (orteronel), or VT-464); prednisone; an osteoprotective agent; a radiation therapy; a kinase inhibitor (e.g. MET, VEGFR, EGFR, MEK, SRC, AKT, RAF, FGFR, CDK4/6); Provenge, Prostvac, Ipilimumab, a PD-1 inhibitor; a taxane or tubulin inhibitor; an anti-STEAP-1 antibody; a heat shock protein 90 (HSP90) or heat shock protein 27 (HSP27) pathway modulator; and/or immunotherapy.

In particular embodiments, treatments disclosed herein result in cancer cell apoptosis. Apoptosis refers to a type of programmed cell death that occurs in eukaryotic cells. Such apoptosis causes the cells to shrink and separate from the surrounding cells folded and change to blebbing of the cell membrane. Furthermore, the nucleus is condensed, and the DNA in the nucleus becomes a small oligonucleotide. It is cut into sections to form an apoptotic body. The apoptosis formed in this way undergoes a series of processes such as phagocytosis by macrophages, resulting in apoptosis.

In particular embodiments, treatments disclosed herein result in cancer cell ferroptosis. Ferroptosis refers to an iron-dependent form of regulated cell death caused by lipid peroxides' accumulation. The glutathione-dependent lipid hydroperoxidase glutathione peroxidase 4 (GPX4) functions in a protective pathway that prevents ferroptosis by converting lipid hydroperoxides into non-toxic lipid alcohols. Ferroptosis has been implicated in cell death underlying several degenerative conditions, and the induction of ferroptosis by inhibition of GPX4 has emerged as a therapeutic strategy to trigger cancer cell death. For additional information regarding apoptosis and ferroptosis, see KR1020080058663 and WO2020205919, respectively.

In particular embodiments, the electrophilic nature of ITC activates the adaptive Nrf2-dependent pathway. In particular embodiments, ITC-ARi conjugates (e.g., 12a, 12b, 2-63) recruit an E3 ligase for AR degradation. In particular embodiments, a GSH-depleting agent (e.g., BSO) is utilized to potentiate the anti-PCa effects of ITC-ARi conjugates (e.g., 12a, 12b, 2-63).

(iv) Kits. Kits, including ITC-containing hybrid AR inhibitors are also provided. Such kits can include ITC-containing hybrid AR inhibitor compounds (such as 12a, 12b, or 2-63), AR inhibitors, such as Enzalutamide or 3-79 and its analogues, electrophilicity-reduced or blocked ITC-AR inhibitor conjugates (e.g., NAC conjugated ITC AR inhibitor conjugates), Buthionine sulphoximine, GSH-depleting agents, diluents to reconstitute for injection, and appropriate buffers and enzymes for digestion. Kits can further include one or more Enz-ITC hybrids and electrophilic analogues of enzalutamide. In particular embodiments, kits can also include some or all of the necessary laboratory and/or medical supplies needed to use the kit effectively, such as gauze, sterile adhesive strips, gloves, tubes, and the like. Variations in contents of any of the kits described herein can be made.

Components of the kit can be prepared for storage and later use. Associated with such container(s) can be noticed in the form prescribed by a governmental agency regulating the manufacture, use, or sale of the kit, which notice reflects approval by the agency of manufacture, use, or sale when required.

Optionally, the kits further include instructions for using the kit in the methods. In various embodiments, the instructions can include appropriate instructions to interpret results associated with using the kit, proper disposal of the related waste, and the like. The instructions can be in the form of printed instructions provided within the kit, or the instructions can be printed on a portion of the kit itself. Instructions may be in the form of a sheet, pamphlet, brochure, CD-ROM, or computer-readable device, or can provide directions to instructions at a remote location, such as a website.

Exemplary Embodiments

1. An isothiocyanate (ITC)-androgen receptor (AR) inhibitor conjugate.
2. The ITC-AR conjugate of embodiment 1, wherein the AR inhibitor is selected from abiraterone, apalutamide, bexlosteride, bicalutamide, cabazitaxel, cyproterone acetate, darolutamide, docetaxel, dutasteride, enzalutamide, finasteride, flutamide, izonsteride, nilutamide, OSU-HDAC42, sunitumib, turosteride, ZD-4054, or 3-79.
3. The ITC-AR conjugate of embodiment 1, wherein the AR inhibitor includes enzalutamide.
4. The ITC-AR conjugate of any of embodiments 1-3, wherein the ITC is selected from sulforaphane, sulforaphene, erysolin, erucin, iberin, alyssin, berteroin, iberverin, cheirolin, 5-methylsulfinylpentyl-ITC, 6-methylsulfinylhexyl-ITC, 7-methylsulfinylheptyl-ITC, 8-methylsulfinyloctyl-ITC, 9-methylsulfinylnonyl-ITC, 10-methylsulfinyldecyl-ITC, phenethyl-ITC, 4-(α.-L-rhamnopyranosyloxy)benzyl-ITC, 3-(α-L-rhamnopyranosyloxy)benzyl-ITC, 2-(α-L-rhamnopyranosyloxy)benzyl-ITC, and 4-(4'-O-acetyl-α-L-rhamnopyranosyloxy)benzyl-ITC.
5. The ITC-AR conjugate of any of embodiments 1-3, wherein the ITC includes PEITC.
6. The ITC-AR conjugate of any of embodiments 1-3, wherein the ITC includes 4,4'-diphenylmethane di-ITC, 4,4'-methylenebis (2,6-diethylphenyl-ITC), 4,4'-methylenebis (2,6-di-t-butylphenyl-ITC) 1,3-bis (isothiocyanatomethyl) cyclohexane, 1,3-propanedi-ITC, 1,5-pentanedi-ITC, 1,7-heptanedi-ITC, 1,9-nonane-ITC, or 1,11-undecanedi-ITC.

7. The ITC-AR conjugate of any of embodiments 1-3, wherein ITC electrophilicity is masked with N-acetyl cysteine.

8. The ITC-AR conjugate of embodiment 1, including 2-63, 12a, 12b, or 3-79. 9. The ITC-AR conjugate of embodiment 1, including 2-63, 12a, 12b, or 3-79 with a sulfur to selenium substitution.

10. A combination treatment including an ITC-AR conjugate of any of embodiments 1-9 and a glutathione (GSH)-depleting agent.

11. The combination treatment of embodiment 10, wherein the GSH-depleting agent is selected from buthionine sulphoximine (BSO); Imidazole Ketone Erastin; Diethylmaleate; Phorone; 2-acetylamino-3-[4-(2-acetylamino-carboxyethylsulfanylthiocarboniamino) phenyl thiocarbamolyl; Sulfasalazine; piperonmin; N-ethyl maleimide; N-pyrenyl maleimide; elastin; sorafenib; 3R-RSL3; DPI19; DPI18; DPI17; DPI13; DPI12; DPI10; DPI7; altoretamine; N-[2-(allyloxy) benzyl]-N-1,3-benzodioxol-5-yl-2-chloroacetamide; 6-(chloromethyl)-N-(2-naphthyl)-1,3,5-triazine-2,4-diamine; 6-(chloromethyl)-N-(4-ethoxyphenyl)-1,3,5-triazine-2,4-diamine; and 2-chloro-N-heptyl-N-m-tolyl-acetamide.

12. The combination treatment of embodiment 10, wherein the GSH-depleting agent includes BSO.

13. A method of destroying cancer cells including administering an ITC-AR conjugate of any of embodiments 1-9 or a combination treatment of any of embodiments 10-12 to the cancer cells, thereby destroying the cancer cells.

14. The method of embodiment 13 wherein the destroying includes inducing apoptosis in the cancer cells and the administering includes administering a therapeutically effective amount of an ITC-AR conjugate of any of embodiments 1-9 to the cancer cells.

15. The method of embodiment 13 wherein the destroying includes inducing ferroptosis in the cancer cells and the administering includes administering a therapeutically effective amount a combination treatment of any of embodiments 10-12 to the cancer cells.

16. The method of any of embodiments 13-15 wherein the cancer cells are in vitro or within a subject.

17. The method of embodiment 16, wherein the subject has prostate cancer.

18. The method of embodiment 17, wherein the prostate cancer is castration-resistant prostate cancer.

19. The method of embodiment 17 or 18, wherein the prostate cancer is resistant to an apoptosis-inducing anticancer agent.

20. A composition including an ITC-AR conjugate of any of embodiments 1-9 and a pharmaceutically acceptable carrier.

21. A kit including an ITC-AR conjugate of any of embodiments 1-9 and a GSH-depleting agent.

22. The kit of embodiment 21, wherein the GSH-depleting agent is selected from buthionine sulphoximine (BSO); Imidazole Ketone Erastin; Diethylmaleate; Phorone; 2-acetylamino-3-[4-(2-acetylamino-carboxyethylsulfanylthiocarboniamino) phenyl thiocarbamolyl; Sulfasalazine; piperonmin; N-ethyl maleimide; N-pyrenyl maleimide; elastin; sorafenib; 3R-RSL3; DPI19; DPI18; DPI17; DPI13; DPI12; DPI10; DPI7; altoretamine; N-[2-(allyloxy) benzyl]-N-1,3-benzodioxol-5-yl-2-chloroacetamide; 6-(chloromethyl)-N-(2-naphthyl)-1,3,5-triazine-2,4-diamine; 6-(chloromethyl)-N-(4-ethoxyphenyl)-1,3,5-triazine-2,4-diamine; and 2-chloro-N-heptyl-N-m-tolyl-acetamide.

23. The kit of embodiment 21, wherein the GSH-depleting agent includes BSO.

(vi) Experimental Examples. Example 1. sothiocyanate (ITC)-Containing Hybrid Androgen Receptor (AR) Inhibitor Downregulates AR and Induces Ferroptosis In Glutathione (GSH)-Deficient Prostate Cancer Cells.

Introduction. Prostate cancer (PCa) is the most commonly diagnosed male malignancy with 170,000 new cases and 30,000 deaths in the US in 2019 projected by the American Cancer Society. Since AR signaling is one of the main driving forces at every stage of PCa, androgen deprivation therapy (ADT) has been a standard treatment for decades. Despite the initial effectiveness, PCa could still progress to a fatal phenotype termed castration-resistant prostate cancer (CRPC) within 2-3 years of ADT (Harris, et al., Nat. Clin. Pract. Urol. 2009, 6, 76-85). The novel androgen biosynthesis inhibitor abiraterone acetate and the AR inhibitor (ARi) enzalutamide (Enz) (FIG. 1) were developed. However, intrinsic and acquired resistance inevitably emerge, leading to variable response and short-lived survival benefit (Watson, et al., Nat. Rev. Cancer 2015, 15, 701-711).

Numerous mechanisms contribute to AR re-activation during ADT and Enz/abiraterone treatments in CRPC, such as: 1) AR gene amplification and AR protein overexpression (Haapala, et al., Hum. Pathol. 2007, 38, 474-478), enabling CRPC to respond to low levels of androgen; 2) upregulation of intratumoral androgen synthesis (Chang K H, et al., Natl. Acad. Sci. U.S.A 2011, 108, 13728-13733); 3) AR mutations allowing the receptor to be promiscuously activated by alternative ligands, even by Enz (Korpal, et al., Cancer Discov. 2013, 3, 1030-1043); and 4) expression of AR splice variants (AR-Vs) without the ligand binding domain (LBD) (Li, et al., Cancer Res. 2013, 73, 483-489): AR-Vs are constitutively active and cannot be inhibited by conventional ARis (e.g., Enz) targeting LBD or by agents targeting androgen biosynthesis (e.g., abiraterone). Aiming to address these challenges, the disclosure provides a design of ITC-containing AR inhibitors (ITC-ARis) by incorporating an ITC moiety into the chemical scaffold of an AR ligand as multifunctional hybrid anti-PCa agents (FIG. 1) (Ou, et al., Mol Cancer Ther 2018; 17(1 Suppl): 2017, Abstract nr A197). ITC is a pleiotropic anti-PCa pharmacophore, and its simple chemical structure allows hybrid drug design via structural modification of an existing ARi without significantly disrupting AR affinity. The single-molecule hybrid drug approach efficiently co-localizes ARi and ITC activities in PCa cells and generates new anti-PCa properties not possessed by Enz.

ITCs, such as phenethyl ITC (PEITC) and sulforaphane (SFN) (FIG. 1), are bioactive metabolites of naturally occurring glucosinolates existing in cruciferous vegetables (e.g., broccoli, cabbage, watercress, etc.) (Zhang, Y., *Carcinogenesis* 2012, 33, 2-9). Epidemiological studies demonstrate a positive correlation between cruciferous vegetable consumption and decreased incidence of PCa, and ITCs are one of the major dietary components contributing to this health benefit (Traka, et al., *Drug Discov.* Today 2014, 19, 1488-1492). In recurrent PCa patients, the SFN-enriched broccoli sprout extracts prolonged PSA (i.e., prostate specific antigen) doubling time without severe adverse events, indicating a potential for further dose escalation (Alumkal, et al., *Invest. New Drugs* 2015, 33, 480-489). Mechanistically, ITCs are inhibitory to multiple PCa growth/survival mechanisms, including AR signaling. For instance, PEITC accelerates AR degradation and reduces AR mRNA (Wang, et al., Carcinogenesis 2006, 27, 2124-2132; Beklemisheva, et al., *Prostate* 2007, 67, 863-870), SFN disrupts the interaction of AR and heat shock protein (Hsp) 90 via inhibiting histone deacetylase (HDAC) 6 (Gibbs, et al., *Proc. Natl. Acad. Sci. U.S.A* 2009, 106, 16663-16668). ITCs also downregulate anti-apoptotic proteins (Hwang, et al., *Int. J. Food Sci. Nutr.* 2010, 61, 324-336), modulate microRNA expression (Yu, et al., *Mol. Nutr. Food Res.* 2013, 57, 1825-1833), decrease chemokine receptor CXCR4 level (Sakao, et al., *Cancer Prev. Res.* (Phila) 2015, 8, 365-374) in PCa cells and suppress the PCa stem-like cells (Vyas, et al., *J. Cell Biochem.* 2016, 117, 2482-2495).

Figure 1:
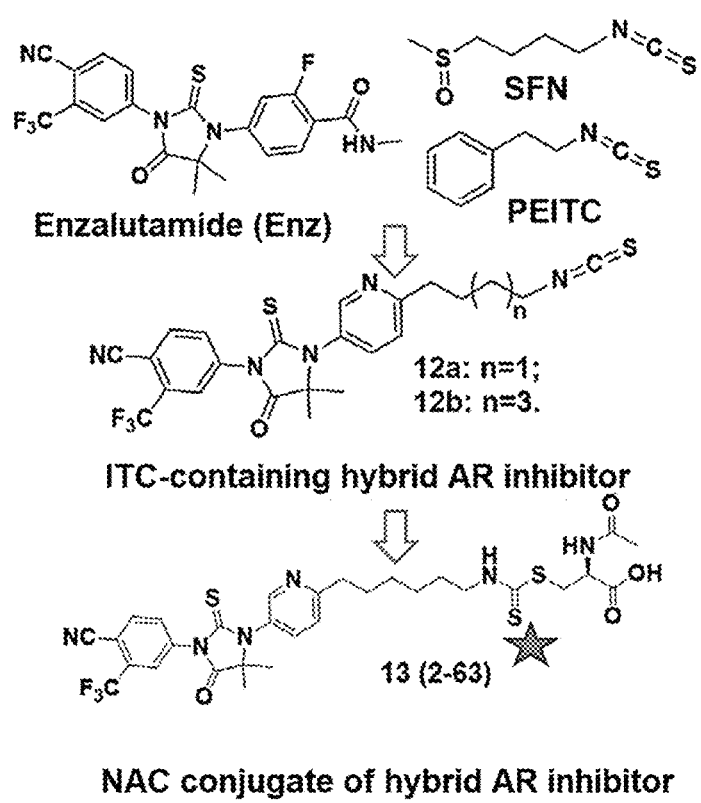
FIG. 1: Design of Isothiocyanate (ITC)-containing AR inhibitor. Chemical structures of enzalutamide (Enz), sulforaphane (SFN), phenethyl ITC (PEITC), and ITC-containing AR inhibitors 12a, 12b, and 2-63.

ITCs are electrophiles and, therefore, can conjugate with cellular GSH and protein sulfhydryl to form dithiocarbamate (Mi, et al., *Carcinogenesis* 2011, 32, 1405-1413). This chemical property is fundamental for the interactions of ITC-containing compounds with cellular targets, such as Hsp90 and HDACs. ITCs were shown to covalently modify the Hsp90 on surface-exposed nucleophilic amino acid residues, resulting in disrupted chaperone function (Li, et al., *J. Nutr. Biochem.* 2012, 23, 1617-1626; Shibata, et al., *J Biol. Chem.* 2011, 286, 42150-42161) and the subsequent proteasome degradation of Hsp90 client proteins. As to HDAC inhibition, N-acetyl cysteine (NAC) or cysteine conjugation to ITC is required, as only the cysteine or NAC conjugates of SFN, but not SFN or its GSH conjugate, acts as HDAC inhibitor (HDACi) to increase acetylation markers in cell culture and in animal models (Myzak, et al., *Cancer Res.* 2004, 64, 5767-5774; Myzak, et al., *Carcinogenesis* 2006, 27, 811-819). The NAC conjugates are the ultimate in vivo metabolites of many dietary ITCs. Once formed from glucosinolate via myrosinase or gastrointestinal microflora-mediated hydrolytic reactions, ITC is conjugated with GSH, followed by conversion via the mercapturic acid pathway to afford NAC conjugate that enters the systemic circulation and is eventually excreted in the urine (Zhang, Y., *Carcinogenesis* 2012, 33, 2-9). Different from common phase II drug metabolites, ITC-NAC conjugates are still biologically active (Hwang, et al., *Int. J. Food Sci. Nutr.* 2010, 61, 324-336; Bhattacharya, et al., *Carcinogenesis* 2012, 33, 394-398; Jiao, et al., *Carcinogenesis* 1997, 18, 2143-2147), explained by: 1) ITC-NAC and parental ITC form an equilibrium in biological matrices (Conaway C C, et al., *Chem. Res. Toxicol.* 2001, 14, 1170-1176), the NAC conjugates gradually release free ITCs; 2) Similar to ITC, ITC-NAC directly modifies protein thiols via trans-thiocarbamoylation reaction (Shibata, et al., *J Biol. Chem.* 2011, 286, 42150-42161); and 3) the NAC conjugate could act as an HDACi (Myzak, et al., *Cancer Res.* 2004, 64, 5767-5774), in contrast to the parental ITC. Since NAC conjugates can be viewed as a carrier or a prodrug of free ITCs in the systemic circulation, the disclosure provides for a converted design of ITC-ARi to the NAC conjugate, exemplified using the compound 2-63 (FIG. 1).

Ferroptosis represents regulated non-apoptotic cell death caused by reactive oxygen species (ROS) and iron-dependent lipid peroxidation (Stockwell, et al., *Cell* 2017, 171, 273-285). Growing evidence supports the exploitation of ferroptosis as a new anticancer approach. Certain cancer types, such as diffuse large B cell lymphoma (DLBCL), is particularly sensitive to ferroptosis induction due to the liability of generating GSH-related antioxidant defense (Zhang, et al., *Cell Chem. Biol.* 2019, 26, 623-633). Across diverse cancer types, treatment resistant cancer cell populations (Viswanathan, et al., *Nature* 2017, 547, 453-457), e.g., persister cells (Hangauer, et al., *Nature* 2017, 551, 247-250), also display susceptibility to ferroptosis. Since apoptosis evasion is a hurdle for treating hormone refractory PCa (McKenzie, et al., *J. Cell Biochem.* 2006, 97, 18-32), therapies selectively activating distinct cell death mechanisms, such as ferroptosis, could be of high value for CRPC patients. The disclosure reports the design and synthesis of ITC-ARi 2-63 and its versatile anti-PCa activities, such as antagonizing AR transactivation and downregulating AR/AR-V7 expression. By combining 2-63 with the GSH synthesis inhibitor buthionine sulphoximine (BSO), the drug combination is not only more effective than 2-63 in depleting AR/AR-V7, but also uniquely causes ferroptosis in Enz-resistant PCa cells. These results demonstrate the great therapeutic benefit of ITC-ARi in combination with GSH-depleting agents as a novel modality against CRPC.

Results. Chemistry (Design of ITC-containing AR inhibitor). Several factors, such as the critical roles of AR signaling in CRPC, ITC's pleiotropic anti-PCa effects as well as the heterogeneous nature of PCa tumor (Ciccarese, et al., *Cancer Treat. Rev.* 2017, 54, 68-73), inspired the design of a class of ITC-ARi hybrid drugs that not only competitively bind to full length AR (FL AR) as a classical antagonist but also downregulate AR/AR-V and suppress additional PCa growth/survival pathways. This single-molecule multifunctional hybrid drug approach increases response rate and cancer cell killing compared to single-target drugs and limits the emergence of resistance mechanisms.

The present disclosure utilized the thiohydantoin scaffold of Enz as the starting point of the hybrid drug design. Enz (FIG. 1) is the latest FDA-approved AR antagonist competing with androgen for AR binding. Its affinity to AR is 5-8 fold higher than that of bicalutamide (Tran, et al., *Science* 2009, 324, 787-790), a clinically used previous-generation AR antagonist. To effectively interact with AR, the trifluoromethyl benzonitrile ring of Enz locates inside the androgen-binding cavity in the LBD, and the cyano group forms essential hydrogen bonds (H-bonds) with Arg752 and Gln711 (Guo, et al., *J. Med. Chem.* 2011, 54, 7693-7704). The conformationally restricted thiohydantoin ring directs the rest of the molecule to the opening side of the androgen-binding pocket. These structure-AR interaction relationships indicated that the fluorobenzene of Enz could tolerate structural modifications for the design of hybrid drugs with retained AR affinity. To improve drug-like properties, fluorobenzene was replaced with pyridine, supported by literature showing pyridine replacement enhances water solubility and oral bioavailability, and does not interfere with AR antagonism of the thiohydantoin-based antagonist (Yoshino, et al., *Bioorg. Med. Chem.* 2010, 18, 8150-8157). An alkyl linker carrying an ITC group was then introduced to afford arylalkyl ITC (FIG. 1). It was predicted that these extra structural elements could be accommodated in the space outside of the androgen binding pocket. To investigate if the length of the linker could impact anti-PCa activities, two Enz-ITC hybrids with four-carbon (compound 12a) and six-carbon chains (compound 12b), respectively (FIG. 1) were designed. Because the NAC conjugate is a carrier and a prodrug of ITC, the 12b was further converted to 13 (named 2-63 in the present disclosure, (FIG. 1). Compared to 12b, the water solubility of 13 (2-63) is greatly improved, and the NAC conjugate gradually releases free ITC 12b in aqueous solution. Because of the temporary blockade of ITC electrophilicity, the utilization of 13 could avoid acute electrophilic attack to normal cells and tissues.

Figure 2:
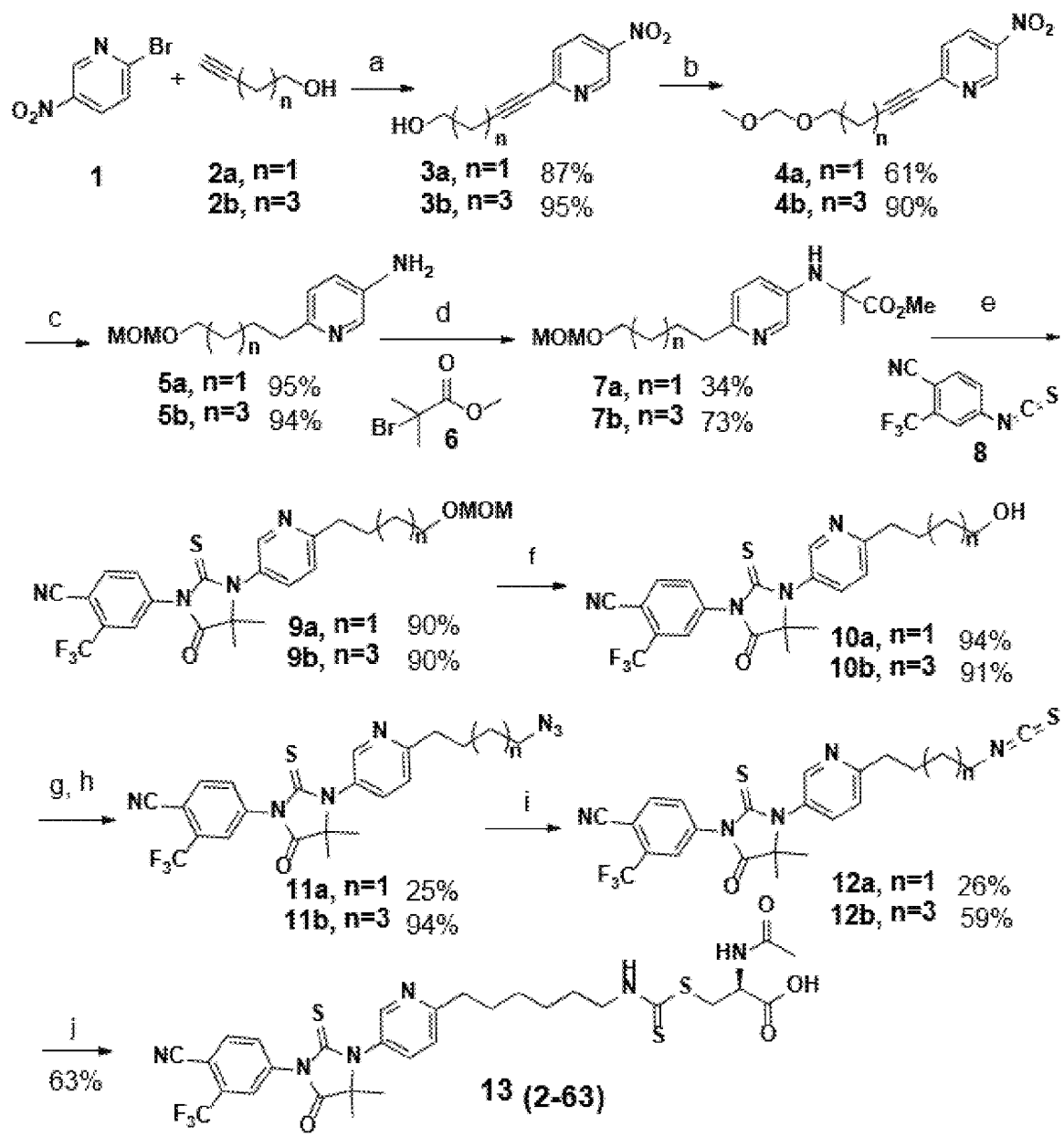
FIG. 2: Synthesis of ITC-containing AR inhibitors 12a, 12b and hybrid drug NAC conjugate 13 (2-63). Reagents and conditions: (a) CuI, Pd(PPh$_3$)$_2$Cl$_2$, TEA, CH$_3$CN, r.t., 2 h; (b) DIPEA, MOMBr, THF, r.t., 6 h; (c) H$_2$, Pd/C, rt, overnight. (d) NaOAc, EtOH, reflux, 10 d; (e) DMSO, 80° C., overnight; (f) HCl, MeOH, 3 h; (g) TEA, MsCl, DCM, r.t., 30 min; (h) NaN$_3$, DMF, rt, 6 h; (i) 1. PPh$_3$, THF, reflux, overnight; 2.CS$_2$, THF, reflux, 5 h; (j) NAC, NaHCO$_3$, 45° C., overnight.

Synthesis of ITC-ARi 12a, 12b, and the related NAC conjugate 2-63. To make the designed hybrid drugs, four- or six-carbon chains were first introduced to the pyridine ring through Sonogashira coupling (FIG. 2). The hydroxyl group of 3 was then protected with methoxymethyl acetal (MOM) to prevent the potential interferences in the following steps.

The nitro and alkyne moieties of 4 were simultaneously reduced via catalytic hydrogenation to afford aromatic amine 5, which was alkylated by 6 in the presence of sodium acetate in ethanol. Because of the low reactivity of the aromatic amine, the reaction was refluxed for 10 days to achieve reasonable yields. The alkylation product 7 reacts with aryl ITC 8 in DMSO at 80° C. to afford the thiohydantoin 9a and 9b with good yield (90%). The MOM protecting group was removed using hydrochloric acid, and the obtained free hydroxyl group was converted to azide 11a and 11b via a methanesulfonate intermediate. The transformation of azide 11 to ITC was conducted via a one-pot two-step procedure (Garcia-Moreno M I, et al., *Carbohydr. Res.* 2002, 337, 2329-2334): triphenylphosphine ($PPh_3$) reacted with the azides to generate phosphazide or iminophosphorane intermediates, which further reacted with carbon disulfide (in excess) to obtain ITC-ARi 12a and 12b, with the four- or six-carbon linker, respectively. Conjugation of 12b with NAC in the presence of sodium bicarbonate afforded the NAC conjugate 13 (2-63).

Figure 3:
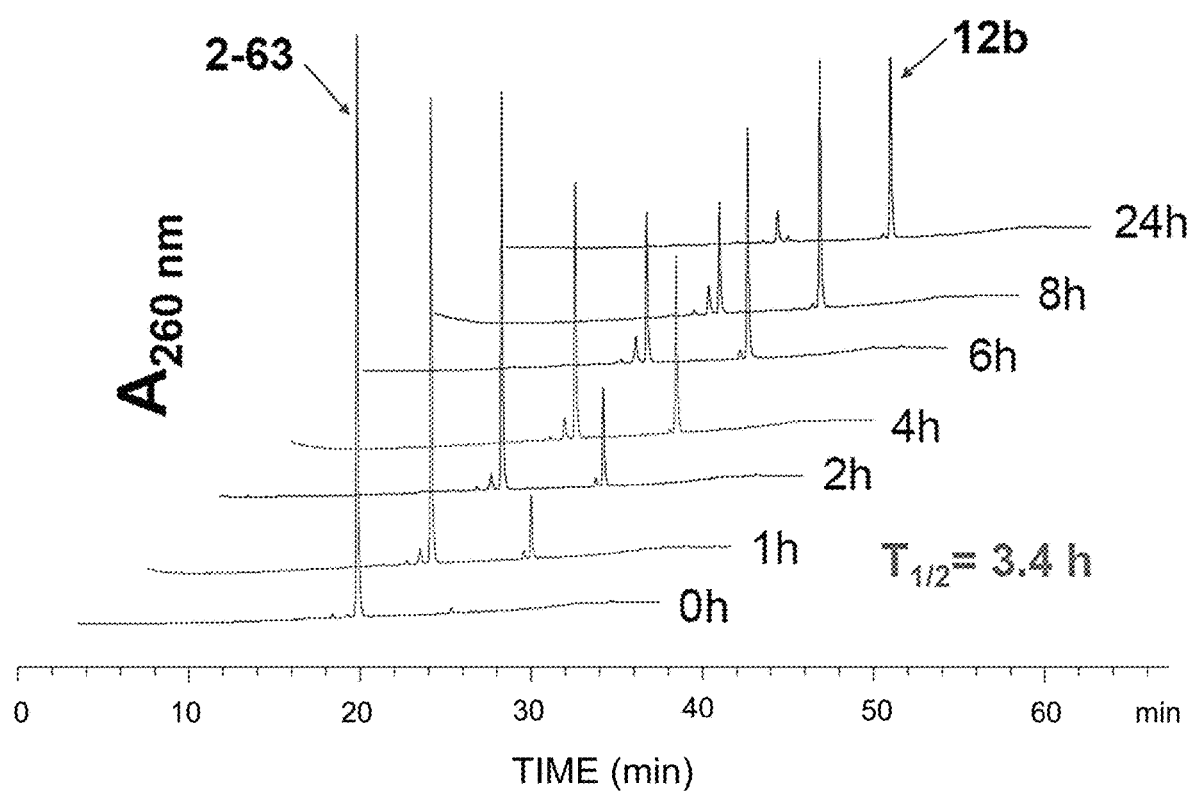
FIG. 3: NAC conjugate 2-63 releases (ITC)-containing AR inhibitors (ITC-Ari) hybrid 12b in aqueous solution. 2-63 (50 µM) was dissolved in Phosphate Buffered Saline (PBS) buffer (pH 7.4, 5% acetonitrile) and incubated at 37°

NAC conjugate 2-63 gradually releases free ITC 12b under physiological condition. The NAC conjugate of ITC could reversibly form free ITCs in aqueous solution (Zhang, Y., *Carcinogenesis* 2012, 33, 2-9). To test this possibility on the setting of ITC-ARi, 2-63 (50 µM) was dissolved in PBS at physiological pH (7.4), and its decomposition was monitored at 37° C. using HPLC. As shown in FIG. 3, free ITC 12b was gradually released, and the half-life of 2-63 is 3.4 h calculated based on the changing of peak area. As shown by the shorter retention time on the C18 reversed-phase HPLC column, conjugation with a polar NAC amino acid greatly improves polarity/water solubility of 2-63 over 12b. 2-63, therefore, can be viewed as a more water-soluble prodrug of 12b when it is used in cell culture or administrated in vivo. This NAC conjugation approach avoids acute/instant electrophilic insult and can constrain the concentration of electrophilic ITC within certain levels. Since non-cancerous cells usually have a larger GSH/antioxidant pool to neutralize electrophilic/oxidative attack (Trachootham, et al., *Cancer Cell* 2006, 10, 241-252), different tolerability to 2-63 could be seen between cancerous and noncancerous cells.

Biological Characterization. ITC-ARi hybrid drugs effectively reduce the viability of PCa cells. By using an MTT assay, it was first examined if the newly synthesized hybrid drugs affect the viability of CRPC-relevant PCa cells. PCa VCaP cells naturally express abundant wild type FL AR as well as AR splice variants (e.g., AR-V7). These cells were, therefore, used as one of the cell culture models in this work to investigate the drug-caused viability loss and AR downregulation. 12a ($IC_{50}$ 4.85 µM) and 12b ($IC_{50}$ 3.89 µM) effectively decreased the viability of VCaP cells grown in full media, and 12b with longer linker (six-carbon vs. four-carbon) showed higher potency (FIG. 4). The same trend was also seen in CRPC C4-2 and 22Rv1 cell lines: when treated with drugs at 5 µM, 12b was consistently more effective than 12a (FIG. 5), which prompted a focus on the 12b scaffold, converted into the NAC conjugate 2-63.

2-63 ($IC_{50}$ 6.09 µM) displayed comparable potency to the free ITCs (12a and 12b) and was more effective than the NAC conjugate of PEITC (PEITC-NAC, $IC_{50}$ 10.13 µM) (FIGS. 4 and 5), a dietary arylalkyl ITC with broadly reported anticancer activities (Wang, et al., *Carcinogenesis* 2006, 27, 2124-2132; Trachootham, et al., *Cancer Cell* 2006, 10, 241-252). Similar rank orders of potency (12b>2-63>PEITC-NAC) were also observed in 22Rv1 and C4-2 cells (FIG. 5). The moderate potency of 2-63 makes its inhibitory effects more specific to malignant cells, supported by the differential anti-proliferative effects of 12b and 2-63 in PCa LNCaP cells and the non-cancerous prostatic epithelial RWPE-1 cells. Measured using an MTT assay, 2-63 was more tolerated by RWPE-1 cells, and significant differences were observed between RWPE-1 and LNCaP cells from 2.5 to 10 µM. On the other hand, the viability of both cells were almost equally suppressed by free ITC 12b under the same experimental conditions (FIG. 6). Because of the better selectivity and water solubility of 2-63 over 12b, 2-63 was used for further in vitro characterization and mechanistic studies.

2-63 inhibits dihydrotestosterone (DHT)-stimulated AR transactivation and downregulates expression of FL AR and AR-V7. AR/AR-V signaling pathways are among the major driving forces of CRPC. Derived from the thiohydantoin AR antagonist and equipped with the AR-modulatory ITC functional group, 2-63 was designed to be inhibitory to AR transcriptional activity and to suppress the expression of AR in PCa cells.

MDA-kb2-cell-based ARE luciferase assays were performed to assess the influence of 2-63 and related compounds on AR transcriptional activity. MDA-kb2 expresses high levels of FL AR, which is generated from the MDA-MD-453 cell line by stably transfecting an androgen-responsive luciferase reporter plasmid driven by the mouse mammary tumor virus (MMTV) promoter (Wilson, et al., *Toxicol. Sci.* 2002, 66, 69-81). Upon androgen stimulation and addition of a luciferase substrate, fluorescence is produced, and the intensity is proportional to the extent of AR activation. An agent that either antagonistically competes with DHT for AR binding or reduces the expression of AR diminishes luciferase activity/fluorescence signal in this experimental system. As shown in FIG. 7, DHT (1 nM) increased luciferase activity in MDA kb2 cells by 8.6-fold. Enz, as a positive control, efficiently suppressed DHT stimulation at all tested concentrations (1-5 µM). ITC-ARi-related compounds with a 6-carbon linker (10b, 11b, 12b, and 2-63) decreased luciferase activity in a dose-dependent manner, demonstrating suppression of AR transcriptional activity. 10b (an alcohol) and 11 b (an azide) are synthetic precursors of the ITC hybrid 12b. Although they were not as potent as Enz at 1 µM (60% inhibition vs. 80% inhibition), the two compounds were Enz-comparable at higher concentrations (2.5 and 5 µM). This data, along with the previous docking results, suggest that the novel thiohydantoin chemical scaffold retains AR antagonist activity through direct AR interaction to compete with DHT. 12b (the ITC hybrid drug) and its NAC conjugate 2-63 were less effective at 1 µM than Enz, 10b, and 11 b, but antagonized DHT-induced AR activation similarly with these non-ITC-containing compounds at higher concentrations (2.5 and 5 µM). The electrophilicity of ITC might be responsible for this observation: the ITC-caused interactions with media or cellular proteins other than AR may reduce the available drug for "pure" AR interaction/inhibition, and this distraction is compensated at higher drug concentrations. 12b and 2-63 showed a similar extent of AR inhibition, supporting that the NAC conjugate is a surrogate of free ITC.

The anti-PCa potential of 2-63 was further characterized by assessing its inhibitory effects on DHT-stimulated C4-2 cell growth. C4-2 is an LNCaP-derived castration-resistant cell line. Although the growth is still responsive to DHT stimulation, C4-2 cells are less sensitive to Enz compared to LNCaP cells and are a frequently used model to evaluate AR antagonism in the CRPC setting (Lai, et al., *Am. J. Pathol.* 2013, 182, 460-473). C4-2 cells were cultured in charcoal-stripped, steroid-free medium and cells were stimulated with androgen. Under tested concentrations (2.5 and 5 µM), 2-63 more efficiently suppressed DHT (1 nM)-stimulated C4-2 cell growth than Enz, e.g., 2-63 and Enz caused 70% and 25% of viability reduction at 5 µM, respectively (FIG. 8). Considering their similar AR suppression in an ARE luciferase assay, the effectiveness of 2-63 might be related to the broader impact on cell growth other than inhibiting the AR pathway alone.

ITC-containing compounds, such as SFN (Gibbs, et al., Proc. Natl. Acad. Sci. U.S.A 2009, 106, 16663-16668) and PEITC (Wang, et al., Carcinogenesis 2006, 27, 2124-2132; Beklemisheva, et al., Prostate 2007, 67, 863-870), are able to downregulate AR expression through inducing AR proteasome degradation and suppressing transcription factors (TFs) that activate AR gene transcription. To investigate if 2-63 could decrease AR/AR-V expression, VCaP cells in full media were treated with 2-63 and 12b (5 and 15 µM) for 16 h. SFN (5 and 15 µM), Enz (10 µM), and HDAC inhibitor SAHA (1 µM) were also tested for comparison. Western blotting analysis showed that 2-63 dose-dependently decreased both FL AR and AR-V7, and was more effective than SFN at higher concentration (FIG. 9). Compared to 2-63, the free ITC 12b seemed to be more effective, especially at lower concentrations (5 µM), likely due to the direct availability of free ITC to relevant cellular targets. In contrast to 2-63 and 12b, the Enz did not change FL AR and upregulated AR-V7 in this experiment. SFN was reported to elicit AR degradation via intracellularly forming HDAC6-inhibiting NAC conjugate (Gibbs, et al., Proc. Natl. Acad. Sci. U.S.A. 2009, 106, 16663-16668). In order to test if there is a similar connection between HDAC inhibition and AR downregulation in 2-63 treatment, the drug-caused acetylation of the α-tubulin and histone H3, standard markers for HDAC6 and nuclear HDAC inhibition, respectively was characterized. Although SFN at 15 µM upregulated α-tubulin acetylation, 2-63 and 12b did not show significant effects on both α-tubulin and histone H3. SAHA (1 µM) induced notable global acetylation but did not decrease the expression of AR (FIG. 9). These results suggest that HDAC inhibition may not be a critical factor in the observed AR downregulation under this cultured condition. In addition to HDACs, protein levels of AR are also affected by heat shock proteins (e.g., Hsp90), which can be disrupted by ITCs via covalent interactions (Li, et al., J. Nutr. Biochem. 2012, 23, 1617-1626; Shibata, et al., J Biol. Chem. 2011, 286, 42150-42161). In the present disclosure, the ITC-related compounds (SFN, 2-63, 12b) did not change Hsp90 at the protein level; however, significantly induced Hsp70. Clear dose-dependent effects were seen in SFN and 2-63 treatments. The decrease of Hsp70 in 12b treatment at 15 µM (still higher than control) from that of 5 µM treatment may arguably be more relevant to general cytotoxicity (FIG. 9). Similar to Hsp70, another cellular stress marker HO-1 (i.e. heme oxygenase 1 was also dose-dependently upregulated by SFN and 2-63 (FIG. 9). The impact of 2-63 on AR and cellular stress markers was further confirmed in a 12 h time course study in VCaP cells (FIG. 10). The drug (10 µM) induced a time-dependent decline of FL AR and AR-V7. Hsp70 and HO-1 were notably increased after 6 h of treatment.

FL AR is a client protein of Hsp90, and AR-V7 might be chaperoned by Hsps other than Hsp90 (Moses, et al., Cancer Res. 2018, 78, 4022-4035). Because Hsp70 upregulation is an indicator of heat shock protein disruption (Kitson, et al., Nat. Chem. 2013, 5, 307-314) that causes client protein degradation, it was assessed whether 2-63 could change the protein stability of AR and AR-V7. VCaP cells were treated with cycloheximide (CHX, 25 µg/mL) to block new protein synthesis, and the following 2-63 treatment significantly reduced the stability of both FL AR and AR-V7 (FIG. 11). 2-63-induced AR/AR-V7 downregulation was partially rescued by the proteasome inhibitor MG-132 (data not shown). This supports the involvement of proteasome degradation in AR reduction. Besides the posttranslational mechanisms, AR downregulation could also be caused by suppressing transcription factors (TFs) that drive the transcription of the AR gene. Sp1 and c-Myc were selected as representatives that could be affected by 2-63. Multiple Sp1 binding sites are located near the transcriptional initiation region of the AR gene. PEITC was shown to reduce AR partially through Sp1 downregulation (Wang, et al., Carcinogenesis 2006, 27, 2124-2132; Beklemisheva, et al., Prostate 2007, 67, 863-870). c-Myc is another TF enhancing AR expression. A recent study shows it promotes AR-V expression by increasing the pre-mRNA splicer levels, hnRNPA1 (Nadiminty, et al., Mol. Cancer Ther. 2015, 14, 1884-1895). The exposure of VCaP cells to 2-63 (5.0, 10 µM) for 24 h dose-dependently reduced Sp1 and c-Myc at the protein level (FIG. 12), suggesting the hybrid drug 2-63 may additionally reduce AR through the downregulation of relevant TFs.

BSO pretreatment significantly improves anti-PCa activities of 2-63. Pharmacological activities of ITCs are highly relevant to their electrophilicity that promotes covalent binding to cellular proteins (Mi, et al., Carcinogenesis 2011, 32, 1405-1413). GSH, the most abundant endogenous free thiol, protects cellular nucleophiles from ITC treatment. To increase the potency of 2-63, the disclosure rationally combined the hybrid drug with BSO (i.e., L-buthionine sulfoximine), a potent and specific GSH biosynthesis inhibitor (Griffith, et al., J. Biol. Chem. 1979, 254, 7558-7560). This drug combination was tested in multiple PCa cell lines. BSO is expected to improve the accessibility of ITC hybrid drugs to their cellular targets via decreasing GSH-involved conjugation of 12b and thiol exchange with 2-63.

VCaP or 22Rv1 cells were pre-treated with BSO (2.5-10 µM) overnight (16 h), followed by co-treatment of 2-63 (1-10 µM) for 24 h. Cell viability was then assessed using an MTT assay. The "interaction index" (Falchi, et al., ACS Chem. Biol. 2017, 12, 2491-2497) was calculated to quantify the combinatorial effects. The interaction index is defined as (% viable cells treated with drug combination)/[(% viable cells treated with drug 1)×(% viable cells treated with drug 2)], a result ranging from 0.8 to 1.2 represents an additive effect, synergism is characterized by a result <0.8 and antagonism is depicted by a result >1.2. 2-63 plus BSO synergistically reduced viability of both PCa cell lines in 24 h co-treatment (FIGS. 13 and 14). Moreover, the two drugs at low µM concentrations (i.e., BSO at 5 µM, 2-63 at 1 µM in 22Rv1 and 2.5 µM in C4-2 cells), very efficiently suppressed colony formation of 22Rv1 and C4-2 cells in multiple-day culture (FIG. 15). In contrast to the dramatic combinatorial effects in PCa cells, BSO does not notably enhance the potency of 2-63 in noncancerous prostatic RWPE-1 cells, even when used at 100 µM. Eighty percent viability of RWPE-1 cells remained after being treated by BSO (100 µM) and 2-63 (5 µM) for 24 h (FIG. 16). In contrast, the viability of PCa cells were significantly decreased: 65% reduction for 22Rv1 (FIG. 17) and 53% for C4-2 cells (FIG. 18). VCaP cells were even more sensitive to the drug combination. When the 2-63 was reduced to 2.5 µM, 60% viability suppression resulted (FIG. 19). These results indicate that the drug combination-caused growth inhibition more specific to malignant cells. Compared to 2-63, the potentiation of BSO to 11b (azide analog of 2-63, 2.5 µM) and PEITC-NAC (2.5 µM) was more limited as shown in VCaP, 22Rv1 (FIG. 19) and C4-2 cells (FIG. 20), suggesting that: 1) the interactions of BSO and ITC is the major mediator for potency enhancement (2-63 vs. 11b); and 2) the synthetic ITC-ARi scaffold is a better "carrier" of ITC than PEITC (2-63 vs. PEITC-NAC). As examined using a Western blotting assay in VCaP cells, 2-63 (2.5 µM) plus BSO (100 µM) more effectively downregulated AR/AR-V7 and c-Myc and upregulated the cellular stress marker HO-1 as compared to the individual drugs alone, which were mostly ineffective at the assayed concentrations (FIG. 21). Enz (10 µM) did not affect the expression of examined cellular markers (except upregulating AR-V7), and BSO (100 µM) didn't change the ineffectiveness of Enz, which support the critical roles of ITC in the observed potency enhancement. Apparently, under a BSO-created GSH-deficient condition, relevant cellular targets (AR, Hsps, Keap1, etc.) are more accessible to 2-63 or 12b, causing efficient growth suppression of PCa cells and the expression changes of the examined cellular proteins.

2-63 and BSO combination induces ferroptosis in PCa cells. Despite inducing significant viability loss in PCa cells, the 2-63 plus BSO combination did not cause detectable PARP cleavage (data not shown), one of the classic features of apoptosis, implying that alternative cell death mechanisms play a role in the observed PCa cell suppression. Because both ITC and BSO change redox balance, and because the significant upregulation of HO-1 by 2-63 (FIG. 21) may increase free ferrous iron (Fe2+) inside cells, ferroptosis, a recently defined non-apoptotic cell death mechanism that occurs due to ROS and iron-caused oxidative lipid damage (Stockwell, et al., *Cell* 2017, 171, 273-285) was explored.

It was first investigated if iron chelators or antioxidants could rescue the viability of drug combination-treated cells. Following BSO (100 µM, 16 h) pretreatment, VCaP or 22Rv1 cells were co-treated with the iron chelator deferoxamine (DFO, 100 µM) and 2-63 (2.5 µM in VCaP and 5 µM for 22Rv1) for 24 h. DFO significantly protected cells from viability loss in both cell lines (FIG. 22). HO-1 catalyzes the decomposition of heme into carbon monoxide, biliverdin, and $Fe^{2+}$. Since $Fe^{2+}$ is required for the generation of ferroptosis-promoting lipid hydroperoxide, overexpression of HO-1 is a key mediator of ferroptosis through sustained elevation of the $Fe^{2+}$ pool (Chang, et al., *Cancer Lett.* 2018, 416, 124-137). Zinc(II) protoporphyrin IX (ZnPP), a specific inhibitor of HO-1, displayed notable cytoprotective effects in VCaP and 22Rv1 cells (FIG. 22), further supporting the involvement of iron in the growth inhibition. The viability of VCaP and 22Rv1 cells were also rescued by α-tocopherol (α-Toc, 100 µM) and a well-recognized ferroptosis suppressor ferrostatin-1 (Fer-1, 0.5 µM) (Zilka, et al., *ACS Cent. Sci.* 2017, 3, 232-243; Skouta, et al., *J. Am. Chem. Soc.* 2014, 136, 4551-4556) (FIG. 22). Both Fer-1 and the lipophilic antioxidant α-Toc can effectively scavenge radicals in phosphatidylcholine lipid bilayers and break the redox cycle that generates lipid hydroperoxide. The reverse of growth suppression by DFO, antioxidants (α-Toc, Fer-1), and ZnPP supports the induction of ferroptosis by the 2-63 and BSO combination. The potent growth inhibition and similar rescuing effects were consistently observed at a much lower BSO (10 µM) concentration in VCaP and 22Rv1 cells (FIGS. 23 and 24), demonstrating 2-63 plus BSO is a robust method allowing ferroptosis induction under broad BSO concentrations. Another line of evidence supporting the occurrence of ferroptosis is that the addition of ferric ammonium citrate (25 µM) exacerbated the lethal effect of BSO (100 µM) and 2-63 (1 µM) combination in VCaP cells (FIG. 25). BSO alone also sensitized VCaP cells to ferric iron. The inhibitory effect was similar to that of BSO plus 2-63 but was not as potent as that of the three-reagent combination. A similar trend was also observed in C4-2 cells. The added ferric iron significantly enhanced the suppressive effects of BSO (100 µM) plus 2-63 (0.6-5 µM) (FIG. 26). To investigate if the efficient AR/AR-V7 depletion by the 2-63 and BSO combination (FIG. 21) is due to ferroptosis induction, VCaP cells were co-treated with the ferroptosis-reversing agents DFO or Fer-1, and their impact on AR/AR-V7 expression as well as the cellular stress markers (Hsp70, HO-1) were assayed using Western blotting. Interestingly, despite the recovery of cell viability (FIG. 22), DFO (100 µM) and Fer-1 (1 µM) failed to rescue AR/AR-V7 and were unable to prevent the upregulation of Hsp70 and HO-1 (FIGS. 29 and 30). 22Rv1 cells express high levels of AR-V7 and are resistant to Enz treatment (Watson, et al., *Nat. Rev. Cancer* 2015, 15, 701-711). 2-63 plus BSO also effectively depletes AR-V7 in this cell line, and again, DFO neither recovers AR-V7 nor prevents the increased expression of Hsp70 and HO-1 (FIG. 27). These results suggest that ferroptosis induction and AR depletion are modulated by separate sets of pathways/cellular targets. HO-1/Hsp70 upregulation occurs upstream to the anti-ferroptotic effects induced by DFO and Fer-1.

Discussion and Conclusion. Curing CRPC remains an unmet medical need. Overexpression/mutation of FL AR (Korpal, et al., *Cancer Discov.* 2013, 3, 1030-1043), the emergence of truncated AR-Vs (Li, et al., *Cancer Res.* 2013, 73, 483-489) (such as AR-V7), and apoptosis evasion (McKenzie, et al., *J. Cell Biochem.* 2006, 97, 18-32) are among the resistance mechanisms enabling CRPC to escape from Enz and abiraterone treatments. In this work, ITC was coupled with a modified AR ligand to create the ITC-containing AR inhibitor hybrid drug, i.e., ITC-ARi, to effectively co-localize antagonistic AR binding and AR/AR-V downregulating properties in PCa cells. Exemplified using the compound 2-63, ITC-ARi provides a novel anti-PCa drug class that efficiently induces AR antagonism and ferroptotic death in PCa cells, particularly under GSH-deficient conditions.

ITC is an electrophile affecting multiple biological pathways, evidenced by the reported broad in vitro/in vivo anti-PCa effects of dietary ITCs, such as SFN (Traka, et al., *Drug Discov. Today* 2014, 19, 1488-1492; Gibbs, et al., *Proc. Natl. Acad. Sci. U.S.A* 2009, 106, 16663-16668) and PEITC (Wang, et al., *Carcinogenesis* 2006, 27, 2124-2132; Beklemisheva, et al., *Prostate* 2007, 67, 863-870; Trachootham, et al., *Cancer Cell* 2006, 10, 241-252). ITCs are differentiated from many other electrophiles (e.g., chloroacetamide, Michael acceptors, etc.) by their reversible covalent interactions with protein sulfhydryls (Ahn, et al., *Proc. Natl. Acad. Sci. U.S.A* 2010, 107, 9590-9595). Since the formation of reversible protein adducts reduces the toxic risks associated with permanent modifications (Lee, et al., *Angew Chem. Int. Ed. Engl.* 2012, 51, 8699-8700), this "reversibility" could contribute to an advantageous safety profile. In order to further avoid abrupt electrophilic insult and improve the water solubility of ITC-based hybrid drugs, free ITC 12b was converted to the NAC conjugate 2-63. In aqueous solution and at physiological pH, 2-63 gradually releases 12b (FIG. 3) and shows higher selectivity to PCa cells (FIG. 6), highlighting that the NAC conjugate is an effective "carrier" of the ITC hybrid drug that improves both its physicochemical properties and cancer selectivity. Additionally, 2-63 more potently inhibited PCa cell growth than PEITC-NAC (the NAC conjugate of dietary PEITC) (FIGS. 4 and 5), likely due to enhanced drug-protein interactions (Mi, et al., *Cancer Res.* 2007, 67, 6409-6416) and the direct inhibitory binding to AR, demonstrating that the hybrid drug structure is a superior arylalkyl ITC scaffold than the naturally occurring PEITC in promoting anti-PCa activities of the ITC functionality. The concept of using prodrugs of electrophiles as anticancer agents is also shown by the clinical development of APR-246 that is converted to the electrophilic methylene quinuclidinone (MQ) through hydrolysis. MQ is a potent Michael acceptor binding to cellular sulfhydryls, such as GSH, p53 mutants, and cellular thiol-dependent redox systems (Perdrix, et al., *Cancers* (Basel) 2017, 9, 172).

2-63-induced AR antagonism exists at various levels, including direct AR binding and the downregulation of AR/AR-V. The AR affinity of the 12b/2-63 scaffold is reflected by the AR antagonist activities of 10b (an alcohol)/11b (an azide) (1-5 µM) in luciferase assays with potencies similar to that of Enz at 2.5 and 5 µM (FIG. 7). Both compounds are close structural analogs of 12b and lack an ITC moiety, implying that the observed reduction of the luciferase signal was solely derived from antagonistic AR binding. AR affinity of 12b/2-63 may improve hybrid drug accumulation in AR+ PCa cells and drug distribution in PCa tumor tissue. This concept is supported by literature showing the interaction with AR decreased the efflux of AR ligand-photosensitizer conjugates and therefore resulted in elevated intracellular drug concentrations (Rapozzi, et al., *Bioconjug. Chem.* 2015, 26, 1662-1671). ITC-GSH and mercapturic acid pathway relevant conjugates (e.g., ITC-Cys-Gly, ITC-NAC conjugates) are expelled from cells through efflux transporters involving MRP-1 and Pgp-1 (Callaway, et al., *Cancer Lett.* 2004, 204, 23-31). AR affinity may therefore increase ITC-ARi retention by promoting interactions of the drug with cellular AR protein, which could be another contributor to the superior anti-PCa effects of 2-63 over PEITC-NAC (FIGS. 4 and 5; FIG. 19).

Different from Enz, 2-63 also decreased the expression of AR and AR-V7 in VCaP cells (FIGS. 9 and 10). As an ITC derivative, 2-63 could downregulate AR through both transcriptional and post-transcriptional mechanisms. FL AR is a client protein of Hsp90. Although not chaperoned by Hsp90, AR-Vs need other Hsps to maintain stability and function. C86, an electrophilic chalcone, interacts with Hsp40 to reduce the stability and expression of AR-Vs (Moses, et al., *Cancer Res.* 2018, 78, 4022-4035). It was envisioned that by interacting with nucleophilic amino acid residues on the Hsps, ITCs (including ITC-ARi) can disrupt the Hsp chaperones (i.e. "foldsome" (Cano, et al., *Mol. Cell Endocrinol.* 2013, 369, 52-62)) of the AR/AR-Vs, which further results in their proteasome degradation. The inhibition of Hsps releases HSF-1 (i.e., heat shock transcription factor-1) to initiate heat shock response. HSF-1 increases the expression of Hsp70 (Zhang, et al., *Chem. Biol.* 2011, 18, 1355-1361), and the upregulated Hsp70 is, therefore, a frequently used marker of Hsp disruption (Kitson, et al., *Nat. Chem.* 2013, 5, 307-314; Zhang, et al., *Chem. Biol.* 2011, 18, 1355-1361). Two evidences, the decreased AR/AR-V7 stability (FIG. 11) and the upregulated Hsp70 expression (FIGS. 9 and 10), support the hypothesis that 2-63 is able to decrease AR/AR-V7 proteins through post-translational mechanisms. Additionally, several TFs are able to modulate AR gene transcription and AR pre-mRNA splicing. 2-63 may also modulate relevant TFs to reduce AR/AR-V at the transcription level. Sp1 is a major TF promoting AR transcription. PEITC decreases Sp1 expression in PCa cells (Wang, et al., *Carcinogenesis* 2006, 27, 2124-2132) and in rat prostate tissue (Beklemisheva, et al., *Prostate* 2007, 67, 863-870), which led to reduced AR expression. Another TF, c-Myc, supports the expression of AR-Vs by transcriptionally upregulating hnRNPA1, a multifunctional RNA-binding protein functioning as an alternative AR pre-mRNA splicer (Nadiminty, et al., *Mol. Cancer Ther.* 2015, 14, 1884-1895). Downregulation of c-Myc using specific shRNA was shown to reduce the expression of hnRNAPA1 and AR-V7 (Nadiminty, et al., *Mol. Cancer Ther.* 2015, 14, 1884-1895). Both PEITC (Wang, et al., *Int. J. Oncol.* 2008, 33, 375-380) and SFN (Vyas, et al., *J. Cell Biochem.* 2016, 117, 2482-2495) have been shown to decrease c-Myc in PCa cells. Consistent with the reported Sp1 and c-Myc modulation by dietary ITCs, 2-63 dose-dependently reduced both TFs at the protein level in VCaP cells (FIG. 12). Overexpression of Sp1 (Sankpal, et al., *Med. Chem.* 2011, 7, 518-525) and c-MYC (Vyas, et al., *J. Cell Biochem.* 2016, 117, 2482-2495; Civenni, et al., *Cancer Res.* 2013, 73, 6816-6827) drives PCa progression and result in a poor prognosis. Downregulation of Sp1 and c-Myc by 2-63 may produce therapeutic effects broader than AR antagonism.

The electrophilic nature of ITC activates the adaptive Nrf2-dependent pathway, evidenced by 2-63-induced upregulation of HO-1 (FIGS. 9 and 10). Cysteine residues of Keap1 (i.e., Kelch-like ECH-associated protein 1) such as Cys151, Cys273, and Cys288, are essential sensors of electrophilic/oxidative stress and were shown to be alkylated by ITC SFN (Dinkova-Kostova, et al., *Proc. Natl. Acad. Sci. U.S.A.* 2002, 99, 11908-11913). Cysteine modification inactivates Keap1 and releases Nrf2 from the Keap1-Cul3 E3 ubiquitin ligase complex (Kobayashi, et al., *Mol. Cell Biol.* 2006, 26, 221-229). Further Nrf2 nucleus translocation initiates the transcription of antioxidant genes, including HO-1 and genes encoding GSH synthesis enzymes (e.g., γ-glutamyl cysteine ligase) and the Xc-system uptaking cysteine for GSH synthesis. Aimed to improve anti-PCa potency of 2-63 by counteracting this cytoprotective adaptation, the drug combination containing 2-63 and the GSH synthesis inhibitor BSO was developed as a new PCa treatment regimen. BSO greatly potentiates anti-PCa effects of 2-63, as demonstrated by synergistically enhancing viability reduction (FIG. 13), dramatically suppressing PCa colony formation (FIG. 15) and efficiently downregulating AR/AR-V by 2-63 at much lower concentrations (FIG. 21). Furthermore, as shown in multiple PCa cells, the 2-63 plus BSO-caused viability loss was effectively rescued by the iron chelator DFO, antioxidants (α-Toc and Fer-1), and HO-1 inhibitor ZnPP (FIG. 22), indicating the induction of ferroptosis. In comparison to their high effectiveness in multiple CRPC cell lines (FIGS. 13 and 15), the drug combination shows encouraging tolerability in noncancerous prostatic RWPE-1 cells (FIG. 16), demonstrating promising selectivity to malignant cells at the tested concentrations.

BSO is a potent inhibitor of γ-glutamylcysteine synthase, the rate-limiting enzyme of GSH synthesis. It was reasoned that BSO could boost the anti-PCa effects of 2-63 through numerous mechanisms (FIG. 28). First, GSH deficiency reduces the GSH conjugation of 12b or the GSH exchange with 2-63, therefore increasing the availability of the drug to cellular targets, such as heat shock proteins and Keap-1, leading to more efficient AR/AR-V depletion and HO-1 induction, respectively (FIG. 21). Second, GSH depletion inhibits enzymatic activities of glutathione peroxidase 4 (GPX4), the central regulator of ferroptosis (Yang, et al., *Cell* 2014, 156, 317-331). GPX4 is the only peroxidase known to effectively convert lipid hydroperoxide to unreactive lipid alcohol by using GSH as a reducing equivalent. Impaired GPX4 activity causes insufficient lipid damage repair and the accumulation of lipid hydroperoxide, which may eventually lead to ferroptosis. Third, GSH deficiency allows 2-63 to induce sustained elevation of HO-1 at a relatively low concentration (FIG. 21). Decomposition of heme by HO-1 enhances intracellular $Fe^{2+}$, which initiates and participates in lipid hydroperoxide formation (Minotti, et al., *Lipids* 1992, 27, 219-226) and promotes Fenton reaction-originated oxidative damage (Feng, et al., *PLoS Biol.* 2018, 16, e2006203). The involvement of HO-1 in ferroptosis induction is supported by the significant viability rescue by ZnPP (FIGS. 22, 23, and 24), a specific HO-1 inhibitor. The expanded Fe2+ pool and the attenuated GPX4 activity cooperatively cause ferroptosis in PCa cells. The disclosure reveals the pro-ferroptotic effect of Nrf2 activation under GSH-deficient conditions. It is also interesting to note that although DFO or Fer-1 rescued cell viability under 2-63 plus BSO treatment, these reagents do not prevent AR/AR-V7 depletion and the upregulation of Hsp70 and HO-1, as shown in VCaP (FIGS. 29 and 30) and 22Rv1 cells (FIG. 27). One possible explanation is that the iron chelation and radical trapping actions of DFO and Fer-1 do not neutralize electrophilicity of 2-63. The covalent interactions of 2-63 with Keap-1 and heat shock proteins result in the observed HO-1/Hsp70 upregulation and AR/AR-V downregulation, respectively.

Systemic GSH depletion is experimentally and therapeutically achievable. BSO has been combined with various agents in clinical trials (O'Dwyer, et al., *J. Clin. Oncol.* 1996, 14, 249-256) and in animal models (Lien, et al., *Nat. Cell Biol.* 2016, 18, 572-578; Harris, et al., *Cancer Cell* 2015, 27, 211-222) to develop new cancer therapies. In these efforts, BSO was either given to humans through IV infusion or delivered to experimental animals via drinking water. Engineered human cyst(e)inase was utilized recently to deplete GSH in mice and non-human primates and is well tolerated for prolonged times (Cramer, et al., *Nat. Med.* 2017, 23, 120-127). The inhibition of cellular cystine uptake by using system Xc-antiporter inhibitors, such as erastin derivatives (Zhang, et al., *Cell Chem. Biol.* 2019, 26, 623-633), is another alternative to decrease GSH concentration in tumors.

Inducing ferroptotic cancer cell death can provide a new treatment modality. Because of abnormal antioxidant and/or lipid metabolism, certain cancer indications or phenotypes are particularly sensitive to pro-ferroptotic agents. DLBCL cells cannot synthesize cysteine from methionine via trans-sulfuration and must rely on external cystine to provide this building block. Reducing cystine uptake by system Xc-inhibitors was shown to effectively cause ferroptosis in DLBCL cells (Zhang, et al., *Cell Chem. Biol.* 2019, 26, 623-633). Moreover, treatment-resistant cancer persister cells are frequently in a high mesenchymal state that heavily relies on GPX4 for survival, representing a vulnerability of this cell population to ferroptosis induction (Hangauer, et al., *Nature* 2017, 551, 247-250). These findings highlight the therapeutic potential of ferroptosis-inducing agents for CRPC treatment. 2-63 plus BSO and other relevant drug combinations provide attractive new options in this endeavor.

In summary, the disclosure provides the newly-designed ITC-containing hybrid AR inhibitor 2-63 incorporating ITC into an AR ligand scaffold. The sulfhydryl reactivity of ITC is transiently masked as a NAC conjugate, which gradually releases parental free ITC in aqueous solution. 2-63 suppresses AR at multiple levels: e.g., directly binding to AR, reducing the stability of AR/AR-V7, and decreasing transcription factors (e.g., c-Myc and Sp1) that are relevant to the expression AR gene. AR affinity of this hybrid drug could additionally promote drug accumulation in AR+ PCa cells. The AR downregulating properties address numerous treatment resistance mechanisms (e.g., overexpression, mutation, AR-Vs, etc.) associated with classical ARi. In vitro anti-PCa potency of 2-63 is significantly enhanced by GSH synthesis inhibitor BSO. 2-63 and BSO cooperatively cause AR/AR-V downregulation and induce ferroptosis in Enz-resistant PCa cells by increasing drug accessibility to cellular targets, expanding the availability of iron, and potentially affecting GPX4 activity. On the other hand, the drug combination is well tolerated by noncancerous prostatic RWPE-1 cells. 2-63 plus BSO effectively targets AR and ferroptotic cell death mechanisms in PCa cells, demonstrating that the combination of ITC-ARi and GSH-depleting agents provide a new concept leading to novel CRPC treatments.

Experimental Section. General Methods for Chemistry. All reagents and solvents were purchased from commercial suppliers and used without further purification. The reactions were monitored using thin-layer chromatography (TLC) on precoated silica gel UV254 plates (Sorbtech, Norcross, GA) and visualized under UV light or after staining by dipping into a solution of phosphomolybdic acid or potassium permanganate and then heated on a hot plate. All the final compounds were purified to >95% purity by performing flash column chromatography over a 200-300 mesh silica gel and further determined using high-performance liquid chromatography (HPLC). The chemical structures of the synthesized compounds were characterized by using nuclear magnetic resonance (NMR) spectroscopy ($^1$H and $^{13}$C) and high-resolution mass spectroscopy (HRMS). All NMR spectra were obtained using a Varian INOVA 600 MHz NMR spectrometer. Chemical shifts are expressed in ppm as a δ value, and singlet (s), doublet (d), triplet (t), quartet (q), multiplet (m), and broad singlet (br s) are used as abbreviations. HPLC analysis was conducted using a Phenomenex (Luna$^R$) C18 (3.5 μm), 3.0 mm× 100 mm column on an Agilent 1100 instrument. Two solvents were used: solvent A, water containing 0.1% formic acid (FA), and 10% (v/v) $CH_3OH$; solvent B, 0.1% FA in CH3CN. Flow rate was set at 0.5 mL/min.

4-(5-Nitropyridin-2-yl)but-3-yn-1-ol (3a). In argon atmosphere, to a mixture of 2-bromo-5-nitropyridine (10.0 g, 49 mmol) and 3-butyn-1-ol (4.55 g, 65 mmol) in acetonitrile (70 mL) were added copper iodine (190 mg, 1 mmol), bis(triphenylphosphine) palladium (II) chloride (175 mg, 0.25 mmol). Triethylamine (TEA) (34 mL, 250 mmol) was slowly added with stirring at 0° C. The mixture was stirred at room temperature overnight. Solvent was removed under reduced pressure. The residue was diluted with EtOAc and was washed with water and brine. The organic phase was separated and dried over anhydrous $Na_2SO_4$ and concentrated. The crude product was purified using flash column chromatography (Hexanes/EtOAc: 1:1) to afford 3a as a brown oil (8.34 g, 87%). 1H NMR (600 MHz, CDCl3) δ 9.33 (d, J=3.0 Hz, 1H), 8.42 (dd, J=8.4 and 2.4 Hz, 1H), 7.55 (d, J=8.4 Hz, 1H), 3.88 (m, 2H), 2.76 (t, J=6 Hz, 2H).

6-(5-Nitropyridin-2-yl)hex-5-yn-1-ol (3b). 3b was prepared similarly as described for 3a. 2-bromo-5-nitropyridine (13.2 g, 65 mmol) and 5-hexyn-1-ol (4.9 g, 50 mmol) were used for this reaction. The crude product was purified by using flash column chromatography (Hexanes/EtOAc: 2:1) to afford 3b brown oil (10.5 g, 95%). 1H NMR (600 MHz, CDCl$_3$): δ 9.34 (d, J=2.4 Hz, 1H), 8.40 (dd, J=8.4 and 3 Hz, 1H), 7.51 (d, J=8.4 Hz, 1H), 3.70 (t, J=12 Hz, 2H), 2.54 (t, J=12 Hz, 2H), 1.77-1.72 (m, 4H). $^{13}$C NMR (150 MHz, CDCl$_3$): δ 149.10, 145.27, 142.41, 131.26, 126.74, 97.12, 62.19, 31.79, 24.38, 19.36.

2-(4-(Methoxymethoxy)but-1-yn-1-yl)-5-nitropyridine (4a). In argon atmosphere, to a solution of 3a (8.34 g, 43.4 mmol) in THF (80 mL) were added N,N-diisopropylethylamine (DIPEA) (18 mL, 108.6 mmol). Bromo(methoxy)methane (7.2 mL, 90%, 78 mmol) was then slowly added at 0° C. The reaction was stirred at room temperature overnight. Precipitate was filtered, and the filtrate was evaporated under reduced pressure. The residue was diluted with EtOAc and was washed with water and brine. The organic phase was separated and dried over anhydrous Na$_2$SO$_4$ and concentrated. The crude product was purified using flash column chromatography (Hexanes/EtOAc: 6:1→4:1) to afford 4a as a yellow solid (6.3 g, 61%). 1H NMR (600 MHz, CDCl$_3$): δ 9.73 (s, 1H), 8.81 (s, 1H), 7.94 (s, 1H), 5.06 (s, 2H), 4.17 (d, J=5.4 Hz, 2H), 3.77 (s, 3H), 3.19 (d, J=5.4 Hz, 2H).

2-(6-(Methoxymethoxy)hex-1-yn-1-yl)-5-nitropyridine (4b). 4b was prepared similarly as described for 4a by using 3b (10.5 g, 47.7 mmol) as the starting material. The crude product was purified by using flash column chromatography (Hexanes/EtOAc: 4:1) to afford 4b as a brown oil (10.69 g, 85%). $^1$H NMR (600 MHz, CDCl$_3$): δ 9.34 (d, J=2.4 Hz, 1H), 8.40 (dd, J=8.4 and 2.4 Hz, 1H), 7.51 (d, J=8.4 Hz, 1H), 3.70 (t, J=12 Hz, 2H), 2.54 (t, J=12 Hz, 2H), 1.77-1.72 (m, 4H). $^{13}$C NMR (150 MHz, CDCl3): δ 149.10, 145.27, 142.41, 131.26, 126.74, 97.18, 80.04, 62.19, 31.79, 24.38, 19.36.

6-(4-(Methoxymethoxy)butyl)pyridin-3-amine (5a). Palladium on carbon (200 mg) was added to a solution of 4a (8.40 g, 35.6 mmol) in methanol (100 mL). The reaction was stirred at pressurized hydrogen atmosphere (60 psi) overnight. The mixture was filtered and the filtrate was evaporated under reduced pressure to afford brown oil that can be directly used in the following step (7.81 g, 95%). $^1$H NMR (600 MHz, CDCl3): δ 8.00 (s, 1H), 6.90 (m, 2H), 4.59 (s, 2H), 3.56 (br s, 2H), 3.52 (t, J=6.6 Hz, 2H), 3.32 (s, 3H), 2.68 (t, J=7.2 Hz, 2H), 1.70-1.76 (m, 2H), 1.59-1.64 (m, 2H). $^{13}$C NMR (150 MHz, CDCl$_3$): δ 152.04, 140.11, 136.83, 122.61, 122.49, 96.35, 67.62, 55.09, 37.01, 29.34, 26.69.

6-(6-(Methoxymethoxy)hexyl)pyridin-3-amine (5b). 5b was prepared similarly as described for 5a by using 4b (10.68 g, 40.4 mmol) as the starting material. The product was obtained as a brown oil (9.05 g, 94%). $^1$H NMR (600 MHz, CDCl$_3$): δ 8.00 (m, 1H), 6.90 (m, 2H), 4.59 (s, 2H), 3.54 (br s, 2H), 3.48 (t, J=6.6 Hz, 2H), 3.33 (s, 3H), 2.65 (t, J=15.6 Hz, 2H), 1.68-1.63 (m, 2H), 1.59-1.55 (m, 2H), 1.40-1.32 (m, 4H). $^{13}$C NMR (150 MHz, CDCl3): δ 152.46, 140.00, 136.77, 122.57, 122.54, 96.35, 67.79, 55.07, 37.26, 30.10. 29.64, 29.09, 26.07.

Methyl 2-((6-(4-(methoxymethoxy)butyl)pyridin-3-yl)amino)-2-methylpropanoate (7a). Sodium acetate (30.5 g, 372 mmol) was added to a solution of 5a (7.81 g, 37.2 mmol) and 6 (33.7 g, 186 mmol) in ethanol (500 mL). The reaction was refluxed for 10 days. The reaction was filtered and the filtrate was concentrated under reduced pressure. The residue was diluted with EtOAc and was washed with water and brine. The organic phase was separated and dried over anhydrous Na$_2$SO$_4$ and concentrated. Crude product was purified by using flash column chromatography (Hexanes/EtOAc: 1:2-EtOAc, 3.78 g, 34.3%). $^1$H NMR (600 MHz, CDCl$_3$): δ 7.94 (d, J=3 Hz, 1H), 6.91 (d, J=8.4 Hz, 1H), 6.81 (dd, J=8.4 and 3 Hz, 1H), 4.59 (s, 2H), 3.97 (br s, 1H), 3.70 (s, 3H), 3.52 (t, J=6.6 Hz, 2H), 3.33 (s, 3H), 2.68 (t, J=7.8 Hz, 2H), 1.70-1.78 (m, 2H), 1.59-1.66 (m, 2H), 1.53 (s, 6H). $^{13}$C NMR (150 MHz, CDCl3): δ 176.16, 152.20, 139.31, 138.32, 123.06, 122.34, 96.36, 67.62, 57.70, 55.01, 52.56, 36.98, 29.38, 26.58, 26.12 (20).

3-((4-(6-(Methoxymethoxy)hexyl)phenyl)amino)-3-methylbutan-2-one (7b). 7b was prepared similarly as described for 7a by using 5b (3.0 g, 12.6 mmol) and 6 (22.8 g, 126 mmol) as the starting materials in the presence of sodium acetate (15.0 g, 189 mmol). The reaction was refluxed for 13 days. The crude product was purified by using flash column chromatography (Hexanes/EtOAc, 1:2) to afford 7b as a yellow oil (3.1 g, 73%). $^1$H NMR (600 MHz, CDCl$_3$): δ 7.90 (d, J=3 Hz, 1H), 6.88 (d, J=8.4 Hz, 1H), 6.78 (dd, J=8.4 and 3 Hz, 1H), 4.56 (s, 2H), 4.00 (brs, 1H), 3.67 (s, 3H), 3.60 (t, J=6.6 Hz, 2H), 3.48 (t, J=6.6 Hz, 2H), 3.30 (s, 3H), 2.62 (t, J=8.1 Hz, 2H), 1.66-1.60 (m, 2H), 1.58-1.52 (m, 2H), 1.50 (s, 6H), 1.38-1.29 (m, 4H). $^{13}$C NMR (150 MHz, CDCl$_3$): δ 176.17, 152.53, 139.25, 138.21, 123.09, 122.27, 96.31, 67.76, 57.67, 55.03, 52.51, 37.18, 29.96. 29.61, 29.11, 26.09 (20), 26.04.

4-(3-(6-(4-(Methoxymethoxy)butyl)pyridin-3-yl)-4,4-dimethyl-5-oxo-2-thioxo imidazolidin-1-yl)-2-(trifluoromethyl)benzonitrile (9a). 8 (8.78 g, 38.5 mmol) was added to a solution of 7a (3.78 g, 12.8 mmol) in DMSO (25 mL). The reaction was stirred at 80° C. overnight. The mixture was diluted with EtOAc and washed with water and brine. The organic phase was dried over anhydrous Na$_2$SO$_4$ and concentrated. The crude product was purified by using flash column chromatography (Hexanes/EtOAc: 2:1→1:1) to afford 9a as a brown oil (5.8 g, 90%). $^1$H NMR (600 MHz, CDCl$_3$): δ 8.45 (d, J=2.4 Hz, 1H), 7.96 (d, J=8.4 Hz, 1H), 7.94 (s, 1H), 7.82 (d, J=7.8, 1H), 7.54 (dd, J=8.4 and 2.4 Hz, 1H), 7.33 (d, J=8.4 Hz, 1H), 4.60 (s, 2H), 3.56 (t, J=6.0 Hz, 2H), 3.34 (s, 3H), 2.90 (t, J=8.4 Hz, 2H), 1.84-1.90 (m, 2H), 1.66-1.72 (m, 2H), 1.58 (s, 6H). $^{13}$C NMR (150 MHz, CDCl3): δ 180.32, 174.67, 163.64, 149.58, 137.44, 136.95, 135.26, 133.56 (q, J=33.2 Hz), 132.16, 129.60, 127.04 (q, J=4.7 Hz), 123.42, 121.82 (q, J=273 Hz), 114.76, 110.24, 96.43, 67.43, 66.35, 55.16, 37.82, 29.44, 26.12, 23.71 (2C).

4-(3-(6-(6-(Methoxymethoxy)hexyl)pyridin-3-yl)-4,4-dimethyl-5-oxo-2-thioxoimidazolidin-1-yl)-2-(trifluoromethyl)benzonitrile (9b). 9b was prepared similarly as described for 9a by using 7b (3.0 g, 8.9 mmol) and 8 (6.0 g, 26.3 mmol) as starting materials. Flash column chromatography (Hexanes/EtOAc: 1:1→1:2) gave 9b as a yellow oil (4.2 g, 90%). $^1$H NMR (600 MHz, CDCl$_3$): δ 8.46 (d, J=2.4 Hz, 1H), 7.97 (d, J=8.4 Hz, 1H), 7.95 (d, J=1.8 Hz, 1H), 7.83 (dd, J=8.4 and 1.8 Hz, 1H), 7.54 (dd, J=8.4 and 2.4 Hz, 1H), 7.32 (d, J=8.4 Hz, 1H), 4.60 (s, 2H), 3.51 (t, J=6.3 Hz, 2H), 3.34 (s, 3H), 2.87 (t, J=8.1 Hz, 2H), 1.83-1.73 (m, 2H), 1.65-1.56 (m, 2H), 1.59 (s, 6H), 1.46-1.40 (m, 4H). $^{13}$C NMR (150 MHz, CDCl$_3$): δ 180.33, 174.69, 164.01, 149.52, 137.42, 136.93, 135.25, 133.61 (q, J=33.2 Hz), 132.14, 129.50, 127.04 (q, J=4.7 Hz), 123.38, 121.82 (q, J=273 Hz), 114.74, 110.30, 96.39, 67.71, 66.35, 55.10, 38.10, 29.60, 29.47, 29.22, 26.05, 23.73 (2C).

4-(3-(6-(4-Hydroxybutyl)pyridin-3-yl)-4,4-dimethyl-5-oxo-2-thioxoimidazolidin-1-yl)-2-(trifluoromethyl) benzonitrile (10a). To the solution of 9a (5.8 g, 11.4 mmol) in methanol, hydrogen chloride (4N, in 1,4-dioxane) (15 mL, 60 mmol) was added dropwise. The reaction was stirred at room temperature overnight. The mixture was neutralized by using saturated sodium bicarbonate, extracted with EtOAc and washed with brine, dried over anhydrous Na$_2$SO$_4$ and concentrated. The crude product was purified by using flash column chromatography (Hexanes/EtOAc: 1:2→1:4→EA) to afford 10a as a brown oil (4.9 g, 94%). $^1$H NMR (600 MHz, CDCl$_3$): δ 8.40 (d, J=2.4 Hz, 1H), 7.93 (d, J=8.4 Hz, 1H), 7.92 (s, 1H), 7.80 (d, J=8.4, 1H), 7.53 (dd, J=8.4 and 2.4 Hz, 1H), 7.31 (d, J=8.4 Hz, 1H), 3.63 (t, J=6.6 Hz, 2H), 2.99 (brs, 1H), 2.86 (t, J=7.8 Hz, 2H), 1.78-1.86 (m, 2H), 1.58-1.66 (m, 2H), 1.54 (s, 6H). $^{13}$C NMR (150 MHz, CDCl3): δ 180.34, 174.67, 163.58, 149.43, 137.65, 137.02, 135.31, 133.37 (q, J=33.2 Hz), 132.27, 129.70, 127.06 (q, J=4.7 Hz), 123.62, 121.85 (q, J=273 Hz), 114.81, 110.07, 66.39, 62.02, 37.45, 32.16, 25.66, 23.62 (20).

4-(3-(6-(6-Hydroxyhexyl)pyridin-3-yl)-4,4-dimethyl-5-oxo-2-thioxoimidazolidin-1-yl)-2-(trifluoromethyl) benzonitrile (10b). 10b was prepared similarly as described for 10a. 9b (1.68 g, 3.14 mmol) in methanol (15 mL) was treated with hydrogen chloride (4N, in 1,4-dioxane) (4 mL). The crude product was purified by using flash column chromatography (Hexanes/EtOAc: 1:1→1:2) to afford 10b as a yellow foam (1.4 g, 91%). $^1$H NMR (600 MHz, CDCl3): δ 8.42 (d, J=2.4 Hz, 1H), 7.95 (d, J=8.4 Hz, 1H), 7.93 (d, J=1.2 Hz, 1H), 7.81 (dd, J=8.4 and 1.2 Hz, 1H), 7.53 (dd, J=8.4 and 2.4 Hz, 1H), 7.31 (d, J=8.4 Hz, 1H), 3.58 (t, J=6.6 Hz, 2H), 2.84 (t, J=7.8 Hz, 2H), 2.16 (br s, 1H), 1.80-1.72 (m, 2H), 1.56 (s, 6H), 1.58-1.50 (m, 2H), 1.44-1.36 (m, 4H). $^{13}$C NMR (150 MHz, CDCl3) δ 180.35, 174.71, 163.92, 149.40, 137.62, 136.96, 135.29, 133.53 (q, J=33.2 Hz), 132.19, 129.60, 127.052 (q, J=4.7 Hz), 123.52, 121.81 (q, J=273 Hz), 114.75, 110.18, 66.38, 62.50, 37.88, 32.43, 29.44, 29.00, 25.42, 23.66 (20). HR-ESI-MS m/z Calcd for C$_{24}$H$_{25}$F$_3$N$_4$O$_2$S [M+H]$^+$ 491.1729, found 491.1724.

4-(3-(6-(4-Azidobutyl)pyridin-3-yl)-4,4-dimethyl-5-oxo-2-thioxoimidazolidin-1-yl)-2-(trifluoromethyl) benzonitrile (11a). In argon atmosphere, methanesulfonyl chloride (0.55 mL, 7.1 mmol) was added dropwise to a stirred solution of 10a (820 mg, 1.77 mmol) in dichloromethane (DCM) and TEA (1.23 mL, 8.87 mmol) at 0° C. The resulted mixture was stirred at 0° C. for 30 min and at room temperature for 1 h. The mixture was diluted with DCM and washed with water and brine, the organic phase was separated, dried over anhydrous Na$_2$SO$_4$ and concentrated under reduced pressure. The residue was re-dissolved in DMF (15 mL), followed by the addition of sodium azide (345 mg, 5.3 mmol). The mixture was stirred at room temperature overnight and was diluted with EtOAc, and washed with water and brine. The crude product was purified by using flash column chromatography (Hexanes/EtOAc, 1:2) to afford 11a as a colorless oil (194 mg, 25%). $^1$H NMR (600 MHz, CDCl$_3$): δ 8.48 (d, J=1.8 Hz, 1H), 7.98 (d, J=8.4 Hz, 1H), 7.95 (s, 1H), 7.83 (d, J=7.8 Hz, 1H), 7.57 (dd, J=8.4 and 2.4 Hz, 1H), 7.34 (d, J=8.4 Hz, 1H), 3.44 (t, J=7.2 Hz, 2H), 2.91 (t, J=7.8 Hz, 2H), 1.86-1.92 (m, 2H), 1.68-1.74 (m, 2H), 1.59 (s, 6H). $^{13}$C NMR (150 MHz, CDCl$_3$): δ 180.35, 174.65, 163.10, 149.67, 137.60, 136.89, 135.26, 133.65 (q, J=33.3 Hz), 132.12, 129.78, 127.03 (q, J=4.7 Hz), 123.47, 121.81 (q, J=273 Hz), 114.72, 110.34, 66.35, 51.19, 37.43, 28.52, 26.47, 23.75 (20). HR-ESI-MS m/z Calcd for C$_{22}$H$_2$OF$_3$N$_7$OS [M+H]$^+$ 488.1491, found 488.1497

4-(3-(6-(6-Azidohexyl)pyridin-3-yl)-4,4-dimethyl-5-oxo-2-thioxoimidazolidin-1-yl)-2-(trifluoromethyl) benzonitrile (11b). 11b was prepared similarly as described for 11a. Briefly, the methanesulfonate intermediate was prepared by reacting 10a (1.35 g, 2.75 mmol) with methanesulfonyl chloride (0.42 mL, 5.47 mmol) in the presence of TEA (1.15 mL, 8.25 mmol) in DCM (15 mL), and was further converted to azide by stirring with sodium azide (506 mg, 7.8 mmol) in DMF (12 mL) at room temperature for 6 h. Flash column chromatography gave 11b as a yellow oil (1.4 g, 94%). $^1$H NMR (600 MHz, CDCl$_3$): δ 8.45 (d, J=2.4 Hz, 1H), 7.95 (d, J=11.4 Hz, 1H), 7.95 (s, 1H), 7.82 (dd, J=8.4 and 1.8 Hz, 1H), 7.54 (dd, J=8.4 and 2.4 Hz, 1H), 7.31 (d, J=8.4 Hz, 1H), 3.24 (t, J=7.2 Hz, 2H), 2.85 (t, J=7.8 Hz, 2H), 1.81-1.73 (m, 2H), 1.62-1.55 (m, 2H), 1.57 (s, 6H), 1.45-1.38 (m, 4H). $^{13}$C NMR (150 MHz, CDCl$_3$): δ 180.33, 174.67, 163.77, 149.55, 137.46, 136.99, 135.26, 133.50 (q, J=33.3 Hz), 132.19, 129.57, 127.05 (q, J=4.7 Hz), 123.41, 121.84 (q, J=273 Hz), 114.77, 110.20, 66.36, 51.35, 37.97, 29.28, 28.87, 28.67, 26.49, 23.68 (2C). HR-ESI-MS m/z Calcd for C$_{24}$H$_{24}$F$_3$N$_7$OS [M+H]$^+$ 516.1785, found 516.1807.

4-(3-(6-(4-Isothiocyanatobutyl)pyridin-3-yl)-4,4-dimethyl-5-oxo-2-thioxoimidazolidin-1-yl)-2-(trifluoro methyl) benzonitrile (12a). To a solution of 11a (194 mg, 0.40 mmol) in THF (5 mL) was added triphenylphosphine (225 mg, 0.86 mmol). The reaction mixture was refluxed overnight, followed by the addition of carbon disulfide (3 mL) and another 12-hour reflux. Solvent was removed under reduced pressure and the crude product was purified by using flash column chromatography (Hexanes/EtOAc, 1:1) to afford 12a as a colorless oil (53 mg, 26%). $^1$H NMR (600 MHz, CDCl$_3$): δ 8.47 (d, J=1.8 Hz, 1H), 7.97 (d, J=8.4 Hz, 1H), 7.95 (s, 1H), 7.83 (d, J=8.4 Hz, 1H), 7.57 (dd, J=8.4 and 1.8 Hz, 1H), 7.34 (d, J=8.4 Hz, 1H), 3.57 (t, J=6.6 Hz, 2H), 2.90 (t, J=7.8 Hz, 2H), 1.86-1.98 (m, 2H), 1.72-1.86 (m, 2H), 1.59 (s, 6H). $^{13}$C NMR (150 MHz, CDCl$_3$): δ 180.35, 174.64, 163.67, 149.73, 137.66, 136.94, 135.28, 133.56 (q, J=33.2 Hz), 132.18, 129.88, 127.05 (q, J=4.5 Hz), 123.52, 121.83 (q, J=273 Hz), 114.77, 110.26, 66.38, 44.87, 37.03, 29.73, 29.52, 26.24, 23.74 (20).

4-(3-(6-(6-Isothiocyanatohexyl)pyridin-3-yl)-4,4-dimethyl-5-oxo-2-thioxoimidazolidin-1-yl)-2-(trifluoro methyl) benzonitrile (12b). 12b was prepared similarly as described for 12a. Briefly, 11 b (1.5 g, 2.9 mmol), and triphenylphosphine (1.5 g, 5.8 mmol) were dissolved in THF (10 mL) and refluxed overnight followed by the addition of carbon disulfide (9 mL) and another 5-hour reflux. Solvent was removed under reduced pressure. The crude product was purified by using flash column chromatography (Hexanes/EtOAc, 1:1) to afford 12b as a yellow foam (905 mg, 59%). $^1$H NMR (600 MHz, CDCl$_3$): δ 8.45 (d, J=2.4 Hz, 1H), 7.96 (d, J=9.0 Hz, 1H), 7.95 (s, 1H), 7.83 (dd, J=8.4 and 1.8 Hz, 1H), 7.55 (dd, J=8.4 and 2.4 Hz, 1H), 7.32 (d, J=8.4 Hz, 1H), 3.48 (t, J=6.6 Hz, 2H), 2.86 (t, J=7.8 Hz, 2H), 1.82-1.76 (m, 2H), 1.72-1.65 (m, 2H), 1.57 (s, 6H), 1.49-1.38 (m, 4H). $^{13}$C NMR (150 MHz, CDCl$_3$): δ 180.33, 174.67, 163.62, 149.57, 137.52, 136.99, 135.27, 133.49 (q, J=33.2 Hz), 132.22, 129.62, 127.06 (q, J=4.5 Hz), 123.47, 121.84 (q, J=273 Hz), 114.77, 110.20, 66.37, 44.97, 37.87, 29.74, 29.16, 28.49, 26.33, 23.70 (2C). HR-ESI-MS m/z Calcd for C$_{25}$H$_{24}$F$_3$N$_5$OS$_2$ [M+H]$^+$ 532.1453, found 532.1478.

N-acetyl-S-((6-(5-(3-(4-cyano-3-(trifluoromethyl)phenyl)-5,5-dimethyl-4-oxo-2-thioxoimidazolidin-1-yl) pyridine-2-yl)hexyl)carbamothioyl)-D-cysteine (13, 2-63). To a solution of 12b (300 mg, 0.56 mmol) in acetonitrile (3 mL) was added N-acetyl-cysteine (NAC) (60 mg, 0.37 mmol) and sodium bicarbonate (240 mg, 2.86 mmol). The reaction mixture was warmed up to 45° C. overnight with stirring. Solvent was removed under reduced pressure. The crude product was purified by using flash column chromatography (Hexanes/EtOAc, 2:1→1:1→DCM/MeOH/AcOH, 10:1: 1%). Purified product was re-dissolved in EtOAc and washed with distilled water to remove the remaining NAC. After concentration, 13 (2-63) was obtained as a white foam (162.2 mg, 63%). $^1$H NMR (600 MHz, CDCl3) δ 8.64 (s, 1H), 8.54 (d, J=1.8 Hz, 1H), 7.97 (d, J=8.4 Hz, 1H), 7.94 (d, J=1.2 Hz, 1H), 7.83 (dd, J=8.4 and 1.8 Hz, 1H), 7.67 (dd, J=8.4 and 2.4 Hz, 1H), 7.40 (d, J=8.4 Hz, 1H), 4.70 (q, J=5.4 Hz, 1H), 3.78 (dd, J=14.4 and 6.0 Hz, 2H), 3.70 (t, J=6.6 Hz, 2H), 2.86 (t, J=7.8, 2H), 1.99 (d, J=7.8 Hz, 3H), 1.82-1.71 (m, 2H), 1.71-1.63 (m, 2H), 1.59 (s, 6H), 1.50-1.36 (m, 4H). $^{13}C$ NMR (150 MHz, CDCl$_3$) δ 196.52, 180.46, 174.58, 172.53, 171.71, 163.15, 148.45, 139.13, 136.94, 135.36, 133.53 (q, J=33.2 Hz), 132.29, 130.35, 127.09 (q, J=4.5 Hz), 124.31, 121.83 (q, J=273 Hz), 114.77, 110.28, 66.50, 53.71, 47.69, 36.83, 35.68, 29.36, 28.54, 27.67, 26.21, 23.75 (2C), 22.96. HR-ESI-MS m/z Calcd for $C_{30}H_{33}F_3N_6O_4S_3$ [M+H]$^+$ 695.1756, found 695.1743.

Molecular modeling and docking. A homology model of AR was built by using Prime (Schrödinger, LLC, New York, NY), in which the antagonistic GR structure (PDB code: 1NHZ) was used as a template. The agonistic forms of AR (PDB code: 2AMB) were aligned with that of 1NHZ. Docking was performed using Glide (Schrödinger, LLC, New York, NY) in the extra precision mode with the induced fit docking protocol. The docking site was defined by the centroid of the template ligand with a box covering the entire ligand-binding site.

2-63 releases 12b in aqueous buffer. Samples for HPLC analysis were prepared by diluting the stock solution (50 mM in DMSO) of 2-63 in PBS buffer (10 mM, pH 7.4) containing 5% acetonitrile. The sample was immediately analyzed right after dilution. The aliquot of incubated samples (37° C.) was analyzed at indicated time points. A linear plot of the log (peak area) versus incubation time was generated to determine the half-life ($T_{1/2}$) of decomposition. HPLC analysis was performed using the Agilent 1100H PLC system coupled with the UV-vis detector set at 260 nm. The column, mobile phase, and flow rate are described in the general methods, and the gradient was as follows: t=0 min, 10% B; t=1 min, 10% B; t=30 min, 90% B; 30-35 min, 90% B.

Cell Cultures, antibodies, and reagents. VCaP, LNCaP, C4-2, 22Rv1, RWPE-1, and MDA-kb2 cells were obtained from the American Type Culture Collection (Rockville, MD). Cells were maintained in RPMI-1640 medium (LN-CaP, C4-2, 22Rv1 and VCaP) or L-15 medium (MDA-kb2) supplemented with 10% heat-inactivated fetal bovine serum (FBS) and 100 U/mL penicillin/streptomycin under 5% $CO_2$ at 37° C. RWPE-1 cells were maintained in Keratinocyte-SFM serum free medium supplemented with EGF (Epidermal Growth Factor) and BPE (Bovine Pituitary Extract) (Thermo Fisher, 17005042). The antibodies against acetyl histone H3 (06-599) and acetyl-histone H4 (06-598) were purchased from Millipore Sigma-Aldrich (Burlington, MA). Acetyl-α-Tubulin (5335), horseradish peroxidase-conjugated anti-rabbit (7074) or anti-mouse (7076) antibodies were from Cell Signaling Technology (Danvers, MA). AR (sc-816), Hsp70 (sc-59569), Hsp90 (sc-7947), glyceraldehyde 3-phosphate dehydrogenase (sc-25778), and c-Myc (sc-40) antibodies were from Santa Cruz Biotechnology (Dallas, TX). AR-V7 antibody (AG10008) was from Precision Antibody (Columbia, MD). Luciferase assay kit (E2520) was from Promega (Madison, WI). 5α-dihydrotestosterone (DHT) and BSO were from Sigma-Aldrich. PEITC-NAc was purchased from Santa Cruz Biotechnology. Drugs were dissolved in DMSO and freshly diluted in culture media before treatment. The final DMSO concentration was less than 0.1% (v/v).

MTT Assay. PCa cells ($6 \times 10^3$ cells/well) were seeded into 96-well plates overnight and then treated with indicated compounds at indicated concentrations and time durations. The MTT (3-(4, 5-Dimethylthiazol-2-yl)-2,5-diphenyltetrazolium bromide) assay was performed according to the standard protocol. Briefly, MTT (0.5 mg/mL) was incubated with cells at 37° C. for 3 hours. Supernatant was removed, followed by the addition of dimethyl DMSO (100 μl). After incubation for 30 minutes at 37° C., absorbance was read at 570 nm on a microplate reader.

Luciferase Assay. MDA-kb2 cells were incubated in Leibovitz's L-15 medium supplemented with 10% charcoal stripped FBS and 1% antibiotic for 24 h. Cells ($1 \times 10^4$ cells/well) were seeded into 96-well plates for 24 h and incubated with the indicated concentration of compounds with or without DHT (1 nM) for 24 h. For all procedures, cells were incubated at $CO_2$ free condition. Steady-Glo® (Promega Corp., Madison, WI) reagent was added to culture media with shaking for 10 min. Samples (100 μL) were transferred to an opaque 96-well white plate, and luminescence was measured using a luminometer.

Western Blotting. Cells treated with the indicated drug or drug combination were washed with ice-cold PBS, lysed in RIPA buffer containing 1% PMSF (phenylmethylsulphonyl fluoride, a serine protease inhibitor) for 30 min over ice and centrifuged (4° C., 14,000 rpm, 15 min). The protein concentration of supernatants was determined using the Pierce BCA Protein Assay Kit (Thermo Fisher, Cat #23225). Proteins in cell lysates (40 μg) were separated using electrophoresis on SDS-PAGE and transferred onto PVDF (polyvinylidenedifluoride) membranes. Membranes were blocked in 5% fat-free milk followed by incubation with primary antibodies overnight at 4° C., and the secondary horseradish peroxidase-conjugated anti-rabbit or anti-mouse antibodies. The blots were developed in the Enhanced Chemiluminescence mixture and detected by ImageQuant™ LAS 4000 imaging system (GE). Density of protein bonds were calculated and analyzed by using imageJ software downloaded from the National Institute of Health website.

Colony formation assay. Cells (22Rv1 or C4-2) were seeded in six-well plates (1,000/well) and cultured overnight. Cells were then treated with 2-63 (1 μM in 22Rv1; 2.5 μM in C4-2), BSO (5 μM) alone or in combination for 24 h. Cells were washed and cultured in a drug-free medium (22Rv1, 11 days; C4-2, 8 days). On the last day, the medium was removed, cells were washed with PBS and fixed with methanol. The colonies were stained with crystal violet solution for 3 h at room temperature and air-dried.

Statistical Analysis. Statistical analyses were performed using GraphPad Prism 8.0. Error bars represent mean±standard deviation (SD) or mean±standard error (SE) as indicated. The differences between data sets were compared using the student's t-test with a significance level set at P<0.05.

Abbreviations Used. ADT, androgen deprivation therapy; AR, androgen receptor; ARi, AR inhibitor; AR-V, AR splice variant; BSO, buthionine sulphoximine; CRPC, castration-resistant prostate cancer; DHT, dihydrotestosterone; DFO, deferoxamine; Enz, enzalutamide; Fer-1, ferrostatin-1; HDAC, histone deacetylase; HDACi, histone deacetylase inhibitor; Hsp, heat shock protein; HSF-1, heat shock transcription factor-1, ITC, isothiocyanate; LBD, ligand binding domain; NAC, N-acetyl cysteine; PCa, prostate cancer; PEITC, phenylethyl isothiocyanate; PEITC-NAC, NAC conjugate of PEITC; SFN, Sulforaphane; Zinc(II) protoporphyrin IX (ZnPP).

Example 2. Combination of Electrophilic AR Inhibitor 3-79 and BSO Induces Ferroptosis in VCaP Cells GSH deficiency enhances drug accessibility to cellular targets (AR, Keap-1, heat shock proteins, etc.), increases the potency of electrophilic AR inhibitor in HO-1 upregulation that expands the intracellular $Fe^{2+}$ pool, and removes the reducing equivalent of GPX4 enzyme. GPX4, Glutathione peroxidase 4; AR-V, AR splice variant; HO-1, heme oxygenase-1 (FIG. 28).

The design and synthesis of 3-79, an electrophilic analogue of enzalutamide (Enz). (FIG. 31) Reagents and conditions: a) $(Boc)_2O$, TEA, DMAP, DCM; b) ammonium formate, Pd/C (10%), isopropanol/$H_2O$; c) methyl 2-bromoisobutyrate, NaOAc, MeOH, reflux; d) ITC, DMSO, 80° C.; e) TFA, DCM; f) 2-(diethoxyphosphoryl)acetic acid, EDCI, DMAP, DCM; g) 2-(dimethylamino)acetaldehyde hydrochloride, DBU, THF, 50%.

Tert-butyl (2-fluoro-4-nitrophenyl)carbamate (2). 2-fluoro-4-nitroaniline (780 mg, 5 mmol) was dissolved in DCM (8 mL) to which Boc anhydride (1.14 g, 5.25 mmol), triethylamine (1 mL, 7.5 mmol), and DMAP (73 mg, 0.6 mmol) was added successively. The reaction mixture was stirred at room temperature overnight. When completed, the reaction mixture was diluted with DCM, washed with water and brine, and dried over anhydrous $Na_2SO_4$. Flash chromatography (Hex/EtOAc=20/1 to 6/1) afforded the product (yellow solid, 775 mg, yield 60%). $^1$H NMR (600 MHz, $CDCl_3$): δ 8.35 (t, J=8.4 Hz, 1H), 8.05 (d, J=8.4 Hz, 1H), 7.97 (dd, J=10.8 Hz, 2.4 Hz, 1H), 7.00 (br, 1H), 1.53 (s, 9H).

Tert-butyl (4-amino-2-fluorophenyl)carbamate (3). Ammonium formate (670 mg, 10.7 mmol) was dissolved in isopropanol/$H_2O$ (10 mL/1 mL) followed by the addition of 10% Pd/C (30 mg) and compound 2 (273 mg, 1.07 mmol). The reaction mixture was stirred at room temperature for 2 h before TLC showed completion of this reaction. Pd catalyst was filtered off through celite, and the filtrate was diluted with DCM, washed with water and brine, and dried over anhydrous $Na_2SO_4$. Evaporation of the solvent directly afforded the product (brown oil, 233 mg, yield 89%), which was used in the next step without further purification. $^1$H NMR (600 MHz, $CDCl_3$): δ7.69 (br, 1H), 6.44-6.33 (m, 3H), 3.61 (br, 2H), 1.49 (s, 9H).

Methyl 2-((4-((tert-butoxycarbonyl)amino)-3-fluorophenyl)amino)-2-methylpropanoate (4). Compound 3 (240 mg, 1.06 mmol) was dissolved in EtOH (20 mL) to which sodium acetate (440 mg, 5.3 mmol) and methyl α-bromoisobutyrate (0.42 mL, 3.18 mmol) was added. The reaction mixture was refluxed for 3 days, followed by removing EtOH under reduced pressure. The resultant residue was partitioned between ethyl acetate and water. The organic phase was collected and washed with water and brine and dried over anhydrous $Na_2SO_4$. Flash chromatography (Hex/EtOAc=4/1) afforded the product (red oil, 197 mg, yield 57%). $^1$H NMR (600 MHz, CDCl3): δ7.70 (br, 1H), 6.41-6.28 (m, 3H), 4.01 (br, 1H), 3.69 (s, 3H), 1.51 (s, 6H), 1.49 (s, 9H).

tert-Butyl (4-(3-(4-cyano-3-(trifluoromethyl)phenyl)-5,5-dimethyl-4-oxo-2-thioxoimidazolidin-1-yl)-2-fluorophenyl)carbamate (5). 4 (1.61 g, 4.9 mmol) and aryl ITC (3.6 g, 15.8 mmol) were dissolved in DMSO (15 mL) and stirred overnight at 80° C. The mixture was diluted with EtOAc and washed with water and brine. The organic phase was dried over anhydrous $Na_2SO_4$ and concentrated. The crude product was purified using flash column chromatography (Hexanes/EtOAc: 6:1) to afford 5 as a yellow solid (2.3 g, 90%).

4-(3-(4-amino-3-fluorophenyl)-4,4-dimethyl-5-oxo-2-thioxoimidazolidin-1-yl)-2-(trifluoromethyl) benzonitrile (6). 5 (4.1 g, 7.8 mmol) was dissolved in a mixture of DCM (15 mL) and TFA (5 mL), and the reaction mixture was stirred for 2 h at room temperature. Solvent was removed under reduced pressure, and the crude product was purified using flash column chromatography (Hexanes/EtOAc: 4:1) to afford 6 as a white solid (2.7 g, 81%).

Diethyl (2-((4-(3-(4-cyano-3-(trifluoromethyl)phenyl)-5,5-dimethyl-4-oxo-2-thioxoimidazolidin-1-yl)-2-fluorophenyl)amino)-2-oxoethyl)phosphonate (7). Amine 6 (216 mg, 0.51 mmol), 2-(diethoxyphosphoryl) acetic acid (110 mg, 0.56 mmol), EDCI (147 mg, 0.77 mmol) and DMAP (3 mg, 0.0255 mmol) were mixed in DCM (5 mL) and the mixture was stirred at room temperature under argon overnight. When completed, the reaction mixture was diluted with DCM and washed with water and brine and dried over anhydrous $Na_2SO_4$. Flash chromatography (DCM/MeOH=20/1) afforded the product (white solid, 255 mg, yield 83%). $^1$H NMR (600 MHz, CDCl3): δ9.20 (s, 1H), 8.47 (t, J=8.4 Hz, 1H), 7.95 (d, A of AB, JAB=8.4 Hz, 1H), 7.92 (s, 1H), 7.80 (d, B of AB, JAB=8.4 Hz, 1H), 7.08-7.06 (m, 2H), 4.21-4.17 (m, 4H), 3.07 (d, J=20.4 Hz, 2H), 1.56 (s, 6H), 1.37-1.34 (m, 6H). $^{13}$C NMR (150 MHz, $CDCl_3$): δ 180.00, 174.69, 162.66, 152.28 (d, J=247 Hz), 136.98, 135.25, 133.55 (q, J=33.1 Hz), 132.18, 130.43 (d, J=9.1 Hz), 127.86 (d, J=10.2 Hz), 127.08 (d, J=4.5 Hz), 125.96, 122.29, 121.82 (q, J=272 Hz), 116.70 (d, J=20.7 Hz), 114.76, 110.23, 66.46, 63.19, 63.14, 36.76, 35.89, 23.66, 16.33, 16.29.

(E)-N-(4-(3-(4-cyano-3-(trifluoromethyl)phenyl)-5,5-dimethyl-4-oxo-2-thioxoimidazolidin-1-yl)-2-fluorophenyl)-4-(dimethylamino)but-2-enamide (3-79). Compound 7 (93 mg, 0.16 mmol) was dissolved in anhydrous THF (3 mL) followed by addition of DBU (70 µl, 0.47 mmol) and 2-(dimethylamino) acetaldehyde hydrochloride (22 mg, 0.24 mmol) at 0° C. After 2 h, the reaction was completed. The mixture was diluted with EA, washed with sat. aq $NaHCO_3$, water and brine, and dried over anhydrous $Na_2SO_4$. Flash chromatography (DCM/MeOH=20/1) afforded the product (yellow oil, 41 mg, yield 50%)$^1$H NMR (600 MHz, $CDCl_3$): δ8.62 (t, J=9.0 Hz, 1H), 7.96 (d, A of AB, JAB=8.4 Hz, 1H), 7.93 (s, 1H), 7.81 (d, B of AB, JAB=8.4 Hz, 1H), 7.62 (d, J=2.4 Hz, 1H), 7.09-7.06 (m, 2H), 7.03-6.99 (m, 1H), 6.18 (d, J=1.8 Hz, 1H), 3.11 (d, J=6 Hz, 2H), 2.27 (s, 6H), 1.57 (s, 6H). $^{13}$C NMR (150 MHz, $CDCl_3$): δ180.01, 174.71, 163.58, 151.98 (d, J=245 Hz), 144.46, 137.00, 135.25, 133.55 (q, J=3.3 Hz), 132.18, 130.11 (d, J=9.0 Hz), 128.13 (d, J=9.7 Hz), 127.08 (d, J=2.4 Hz), 126.08, 124.73, 122.17, 121.83 (q, J=273 Hz), 116.52 (d, J=21.3 Hz), 114.77, 110.20, 66.48, 60.26, 45.57, 23.67.

3-79 and BSO effectively reduce the viability of VCaP cells. Very similar to the combination of 2-63 and BSO, the potency of 3-79 in viability suppression is also increased under GSH deficient conditions. The viability loss of VCaP cells is rescued by antioxidants and iron chelators. As shown in FIG. 32, 3-79 (10 µM) plus BSO (100 µM)-induced viability loss was rescued by DFO (100 µM), α-Tocopherol (α-Toc, 100 µM), and Ferrostatin-1 (Fer-1, 0.5 µM). Data (n=6-8) represent mean±SD obtained from MTT assay. Statistical significance was assessed by using two-tailed Student's t-tests. ***, $P<0.001$.

Analogs of 3-79 can be found in FIG. 33.

(vi) Closing Paragraphs. Unless otherwise indicated, the practice of the present disclosure can employ conventional techniques of immunology, molecular biology, microbiology, cell biology, and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. A material effect would cause a statistically significant reduction in the ability to obtain a claimed effect according to a relevant experimental method described in the current disclosure, for example, the induction of ferroptosis in apoptosis-resistant prostate cancer cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles, and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. An androgen receptor (AR) inhibitor of Formula II, III, IV, V, or a salt thereof:

Formula II

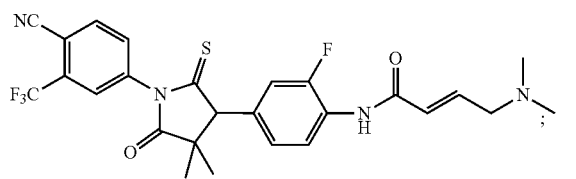

Formula III

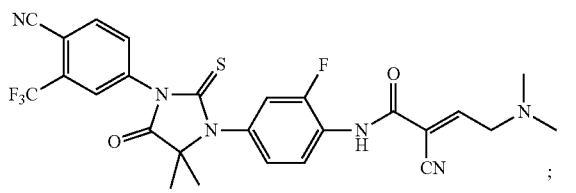

Formula IV

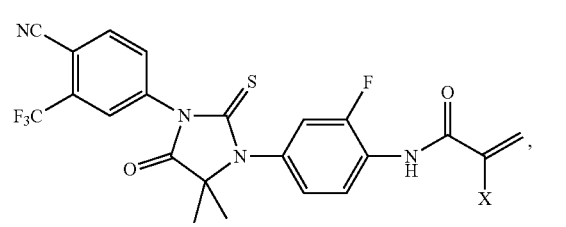

wherein X is H or CN; and

Formula V

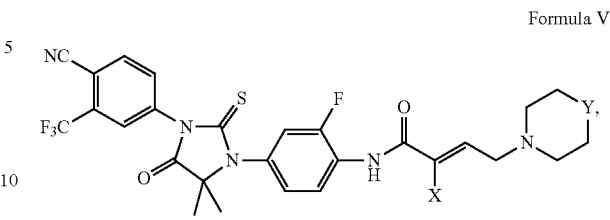

wherein X=H, or CN; and Y=CH$_2$, O, NH, or NCH$_3$.

2. A composition comprising the AR inhibitor or a salt thereof of claim 1 and a carrier.

3. A pharmaceutical composition comprising the AR inhibitor or a salt thereof of claim 1 and a pharmaceutically acceptable carrier.

4. A method of inducing cancer cell death in a subject in need thereof comprising administering the AR inhibitor of claim 1 to the subject, thereby inducing cancer cell death in the subject.

5. The method of claim 4, wherein the method further comprises administering a glutathione (GSH)-depleting agent to the subject.

6. The method of claim 5, wherein the GSH-depleting agent is buthionine sulphoximine (BSO).

7. The method of claim 5, wherein the GSH-depleting agent is imidazole ketone erastin.

8. The method of claim 5, wherein the subject has prostate cancer.

9. The method of claim 8, wherein the prostate cancer is castration-resistant prostate cancer.

10. The method of claim 8, wherein the prostate cancer is resistant to an apoptosis-inducing anti-cancer agent.

* * * * *

UNITED STATES PATENT AND TRADEMARK OFFICE
CERTIFICATE OF CORRECTION

PATENT NO. : 12,133,846 B2
APPLICATION NO. : 17/071896
DATED : November 5, 2024
INVENTOR(S) : Zhihui Qin et al.

Page 1 of 1

It is certified that error appears in the above-identified patent and that said Letters Patent is hereby corrected as shown below:

In the Claims

Claim 1, Column 39, Formula II, Lines 15-21, change "

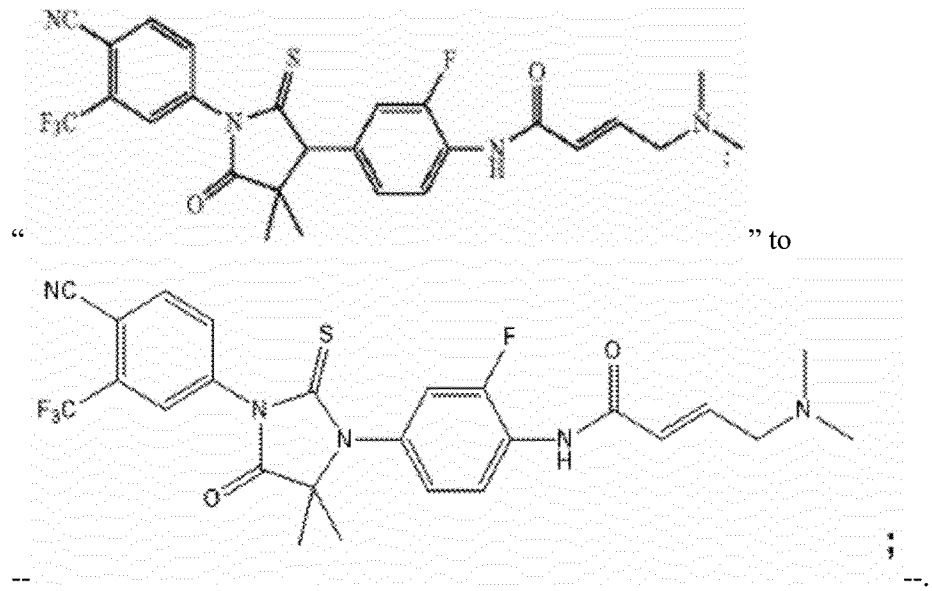

" to

Claim 1, Column 40, Line 1, change "wherein X is H or CN; and" to --wherein X is H or CN; or--.

Signed and Sealed this
Sixteenth Day of September, 2025

Coke Morgan Stewart
*Acting Director of the United States Patent and Trademark Office*